Figure 3:
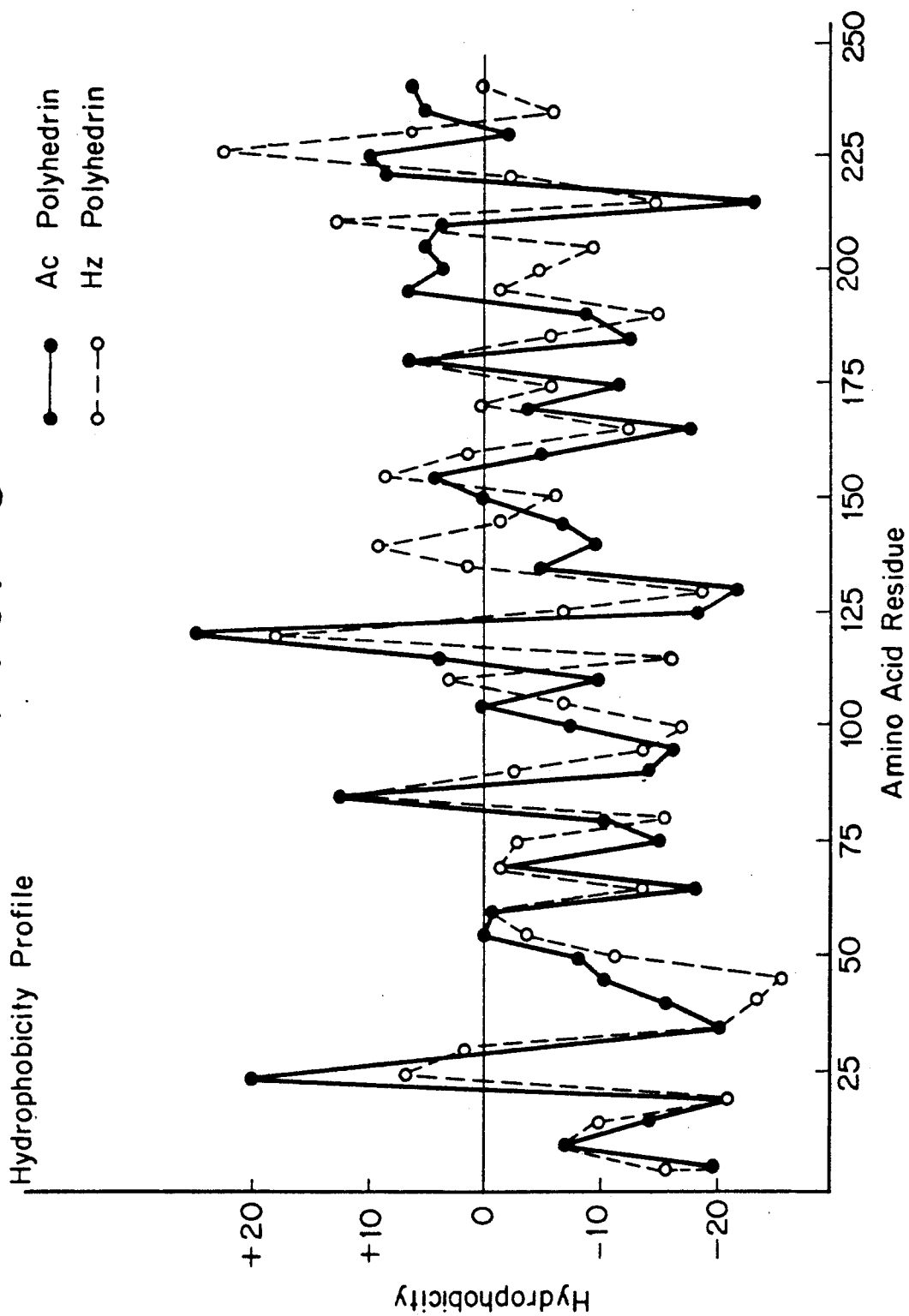

United States Patent [19]

Fraser et al.

[11] Patent Number: 5,041,379
[45] Date of Patent: Aug. 20, 1991

[54] HELIOTHIS EXPRESSION SYSTEMS

[75] Inventors: Malcolm J. Fraser; Elliot D. Rosen; Victoria A. Ploplis, all of South Bend, Ind.

[73] Assignee: American Biogenetic Science, Inc., Copiague, N.Y.

[21] Appl. No.: 168,109

[22] Filed: Mar. 14, 1988

Related U.S. Application Data

[63] Continuation-in-part of Ser. No. 26,499, Mar. 16, 1987, abandoned.

[51] Int. Cl.$^5$ .................... C12N 7/01; C12N 15/09; C12N 15/85
[52] U.S. Cl. .................... 435/235.1; 435/69.1; 435/70.1; 435/91; 435/172.3; 435/240.2; 435/320.1; 536/27; 935/3; 935/6; 935/9; 935/22; 935/33; 935/34; 935/47; 935/48; 935/59; 935/60; 935/61; 935/66; 935/70
[58] Field of Search .................... 435/68, 70, 91, 235, 435/317.1, 317.2, 320, 172.3, 320.1, 240.2; 536/27; 935/32, 34, 52, 70, 3, 6, 9, 22, 33, 47, 48, 59, 60, 61, 66

[56] References Cited

U.S. PATENT DOCUMENTS

| | | | |
|---|---|---|---|
| 4,722,849 | 2/1988 | Valenzuela et al. | 435/172.3 |
| 4,745,051 | 5/1988 | Smith et al. | 435/69.1 |
| 4,870,023 | 9/1989 | Fraser et al. | 435/320.1 |

FOREIGN PATENT DOCUMENTS

0155476 1/1984 European Pat. Off. .
0127839 12/1984 European Pat. Off. .

OTHER PUBLICATIONS

Kuroda et al., (1985), Embo J., 5:1359–1365.
Vlak et al., (1985), pp. 489–542, Viral Insecticides for Biolog. Control, Academic Press.
Harrap, 1972, Virology 50:124–132.
Engstrom, 1974, Biochem. Exp. Biol. 11:7.
Epstein et al., 1977, Biochem. J. 167:321–332.
Rohrmann et al., 1977, Biochemistry 16:1634.
Maruniak et al., 1978, J. Invert. Pathol. 32:196–201.
Tinsley, T. and Harrap, K., 1978, "Comprehensive Virology", vol. 12, pp. 1–101, H. Fraenkel-conrat and R. Wagner, Eds., Plenum Press, NY.
Scharnhorst, D. and Weaver, R., 1980, Virology 102:468–472.
McIntosh et al., 1981, J. Invert. Pathol. 37:258–264.
Tweeten et al., 1981, Microbiological Rev. 45:379–408.
Duncan et al., 1983, J. Gen. Virology 64:1531–1542.
Tija et al., 1979, Virology 99:399–409.
Rohrmann et al., 1981, J. Mol. Evol. 17:329–333.
Vlak et al., 1981, J. Virology 40:1531–1542.
Adang et al., 1982, J. Virology 44:782–793.
Smith, G. and Summers, M., 1982, Virology 123:393–406.
Vlak et al., 1982, Virology 123:222–228.
Erlandson et al., 1983, Virology, 126:398–402.
Smith et al., 1983, J. Virology, 45:215–225.
Smith et al., 1983, J. Virology, 46:584–593.
Knell & Summers, 1984, J. Gen. Virology, 65:445–450.
Heng et al., 1985, Scientia Sinica, pp. 1051–1059.
Leisy et al., 1986, Virology 153:280–288.

(List continued on next page.)

*Primary Examiner*—Richard A. Schwartz
*Assistant Examiner*—Richard C. Peet
*Attorney, Agent, or Firm*—Pennie & Edmonds

[57] ABSTRACT

The present invention relates to recombinant vector/host systems which can direct the expression of foreign genes under the control of the Heliothis polyhedrin promoter. Using the systems of the present invention, a heterologous gene of interest can be expressed as an unfused peptide or protein, a fusion protein, or as a recombinant occlusion body which comprises crystallized polyhedrin fusion proteins bearing the heterologous gene product on the surface of or within the occlusion body. The recombinant proteins or occlusion bodies of the present invention have uses in vaccine formulations and immunoassays, as biological insecticides, and as expression systems for the production of foreign peptides or proteins.

15 Claims, 25 Drawing Sheets

OTHER PUBLICATIONS

Miller, L. K., 1981, Genetic Engineering i Plant Sciences, Praeger Publishers, New York, pp. 203–224.
Smith et al., 1983, Mol. Cell Biol. 3:2156–2165.
Maeda et al., 1984, Proc. Japan Acad. 60:423–426.
Pennock et al., 1984, Mol. Cell. Biol. 4:399–406.
Carbonell et al., 1985, J. Virology 56:153–160.
Maeda et al., 1985, Nature 315:592–594.
Miyamoto et al., 1985, Mol. Cell. Biol. 5:2860–2865.
Summers, M. D. and Smith, G., 1985, Genetic Engineering of Baculoviruses, Genetically Altered Viruses and the Environment, Meeting, Cold Spring Harbor, NY, Apr. 18–May 1, 1985, pp. 319–331.
Matsura et al., 1986, J. Gen. Virol. 67:1515–1529.
Possee, 1986, Virus Research 5:43–59.
Estes et al., 1987, J. Virology 61:1488–1494.
Hu et al., 1987, J. Virology 61:3617–3620.
Inumaru et al., 1987, J. Gen. Virol. 68:1627–1635.
Jeang et al., 1987, J. Virology 61:1761–1764.
Matsuura et al., 1987, J. Gen. Virology 68:1233–1250.
Rice et al., 1987, J. Virology 61:1712–1716.
Luckow et al., 1988, Biotechnology 6:47–55.
Hohmann et al., 1983, Virology 125:432–444.
Quant et al., 1984, Applied and Environmental Microbiology, 48:732–736.
Huang et al., 1985, Virology 143:380–391.
Steeves et al., 1974, J. Virology 14:187–189.
Dalyrample et al., 1981, in "The Replication of Negative Strand Viruses", ed. Bishop, D. and Compans, R., Elseveir North Holland Publishers, N.Y., pp. 167–172.
Massey et al., 1981, Virology 115:20–32.
Gonzalez-Scarano et al, 1982, Virology 120:42–53.
Mathews et al., 1982, J. Immunol. 129:2763–2767.
Matsuno et al., 1983, Infection and Immunity, 39:155–158.
Warren, 1985, "Vaccines", 85, Lerner, R. et al., Eds., Cold Spring Harbor Laboratory, N.Y., pp. 373–376.
Granoff et al., 1986, J. Infect. Dis., 153:448–461.

```
                    -150
         TGCAAGAATATGAAGATTTCTGTCCTCGTGTTGAAAATTTGTAATAAAACTAAATAAACCTTTAATATAA
-80
ATATTAAACATACACTTTTATTTCTAAAATAAGTATTTTTTTCCTATTGTTCAAGATTGTGAAAAATCAAATATCCCATA met tyr thr arg tyr ser tyr ser pro thr leu glu lys thr tyr val tyr asp asn lys
ATG TAT ACT CGT TAC AGT TAC AGC CCT ACT TTG GGC AAA ACC TAT GTG TAC GAC AAC AAA
 1   AccI                                                        KsaI tyr phe lys asn leu glu ala val ile lys asn ala lys arg lys lys his leu glu glu
TAC TTT AAG AAT TTA GGT GCT GTT ATT AAA AAT GCC AAA CGC AAG AAG CAT TTA GAG GAG
61                                                                      MnlI
                                                                        HgiAI/SduI
his glu his glu gly arg asn leu asp ser leu asp lys tyr leu val ala glu asp pro
CAC GAA CAT GAA GAA CGC AAC TTG GAT TCG CTC GAC AAA TAC TTG GTG GCG GAA GAT CCT
 121     NlaIII MoeII           HinfI  TaqI phe leu gly pro gly lys asn gln lys leu thr leu phe lys glu ile arg ser val lys
TTT TTG GGA CCT GGC AAA AAT CAA AAA CTA ACT TTG TTT AAA GAG ATT CGC AGC GTT AAG
181                 pH15 pro asp thr met lys leu val val asn trp ser gly arg glu phe leu arg glu thr trp
CCC GAC ACA ATG AAG CTT GTA GTT AAC TGG AGC GGT CGC GAA TTT CTT CGC GAA ACT TGG
241              HindIII    HindII            NruI            NruI thr arg phe met glu asp ser phe pro ile val asn asp gln glu ile met asp val phe
ACT CGT TTC ATG GAA GAC AGT TTT CCC ATT GTA AAC GAC CAA GAA ATT ATG GAC GTG TTT
301 leu ser val asn met arg pro thr lys pro asn arg cys tyr arg phe leu ala gln his
CTG TCT GTT AAT ATG CGA CCA ACC AAA CCG AAC CGT TGT TAC CGA TTC TTA GCG CAA CAC
361 ala leu ala cys asp pro asp tyr ile pro his glu val ile arg ile val glu pro ser
GCT CTG GCT TGT GAT CCC GAC TAT ATT CCT CAC GAA GTC ATT CGT ATT GTA GAA CCT TCC
421 tyr val gly ser asn asn glu tyr arg ile ser leu ala lys lys tyr gly gly cys pro
TAT GTA GGC AGT AAC AAC GAG TAC AGA ATT AGT TTA GCC AAA AAA TAC GGC GGT TGC CCC
481 val met asn leu his ala glu tyr thr asn ser phe glu asp phe ile thr asn val ile
GTT ATG AAT TTG CAC GCT GAA TAC ACT AAT TCC TTT GAA GAT TTC ATT ACC AAC GTA ATT
541 trp glu asn asn tyr lys pro ile val tyr val gly thr asp ser ala glu glu glu glu
TGG GAG AAC TTC TAC AAA CCA ATT GTT TAC GTA GGC ACT GAT TCT GCC GAA GAA GAG GAA
601 ile leu leu glu val ser leu ile phe lys ile lys glu phe ala pro ala pro leu tyr
ATA CTC CTA GAG GTT TCT TTG ATA TTT AAG ATC AAA GAA TTT GCA CCT GCG CCG CTA TAC
661 thr gly pro ala tyr stop
ACT GGT CCT GCA TAT TAA ACTTGCGATTCAGT
721
```

FIG. 1

FIG. 1A
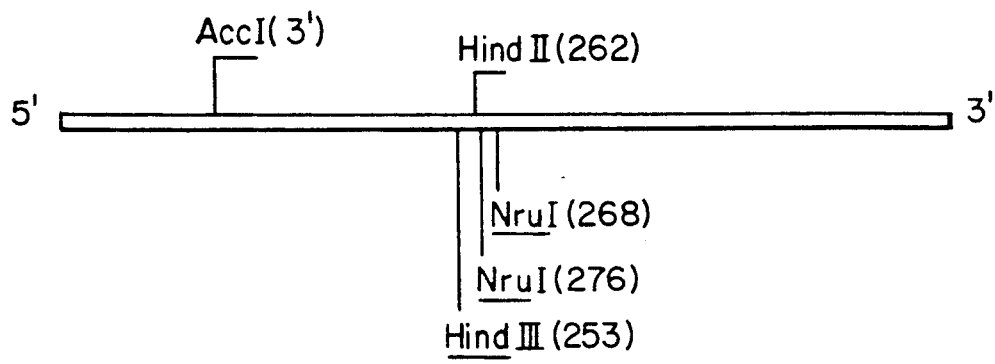
FIG. 1B
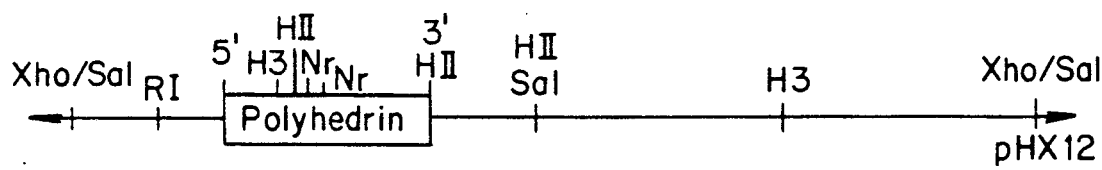
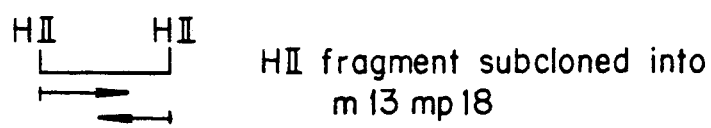
HII fragment subcloned into m13 mp18
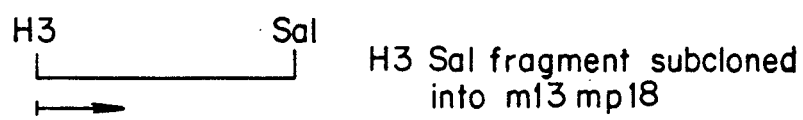
H3 Sal fragment subcloned into m13 mp18
RI–H3 fragment subcloned into m13 mp18
RI–NruI fragment subcloned into m13 mp18
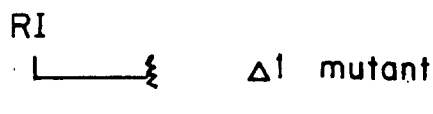
Δ1 mutant

```
              ATG      CCG GAT TAT TCA TAC CGT CCC ACC ATC GGG CGT ACC TAC GTG TAC GAC AAC AAG
A.c.          Met  --- Pro Asp Tyr Ser Tyr Arg Pro Thr Ile Gly Arg Thr Tyr Val Tyr Asp Asn Lys
H.z.    1          Tyr Thr Arg             Ser         Leu     Lys
B.m.                       Asn             Asn

TAC TAC AAA AAT TTA GGT GCC GTT ATC AAG AAC GCT AAG CGC AAG AAG CAC TTC GCC GAA
A.c.          Tyr Tyr Lys Asn Leu Gly Ala Val Ile Lys Asn Ala Lys Arg Lys Lys His Phe Ala Glu
H.z.   21         Phe                                                             Leu Glu
B.m.                              Gly Leu                                         Leu Ile
                                                                                  BamHI
              CAT GAG ATC GAA GAG GCT ACC CTC GAC CCC CTA GAC AAC TAC CTA GTG GCT GAG GAT CCT
A.c.          His Glu Ile Glu Glu Ala Thr Leu Asp Pro Leu Asp Asn Tyr Leu Val Ala Glu Asp Pro
H.z.   41         His             Arg Asn     Ser         Lys             Met
B.m.          Glu His Lys         Lys Gln Trp Leu

TTC CTG GGA CCC GGC AAG AAC CAA AAA CTC ACT CTC TTC AAG GAA ATC CGT AAT GTT AAA
A.c.          Phe Leu Gly Pro Gly Lys Asn Gln Lys Leu Thr Leu Phe Lys Glu Ile Arg Asn Val Lys
H.z.   61
B.m.                                                                              Val

CCC GAC ACG ATG AAG CTT GTC GTT GGA TGG AAA GGA AAA GAG TTC TAC AGG GAA ACT TGG
A.c.          Pro Asp Thr Met Lys Leu Val Val Gly Trp Lys Gly Lys Glu Phe Tyr Arg Glu Thr Trp
H.z.   81                             Asn     Asn Ser     Arg         Leu
B.m.                              Ile     Asn     Ser                 Leu

ACC CGC TTC ATG GAA GAC AGC TTC CCC ATT GTT AAC GAC CAA GAA --- GTG ATG GAT GTT
A.c.          Thr Arg Phe Met Glu Asp Ser Phe Pro Ile Val Asn Asp Gln Glu --- Val Met Asp Val
H.z.  101                                                             --- Ile
B.m.                      Val                                                     Val

TTC CTT GTT GTC AAC ATG CGT CCC ACT AGA CCC AAC CGT TGT TAC AAA TTC CTG GCC CAA
A.c.          Phe Leu Val Val Asn Met Arg Pro Thr Arg Pro Asn Arg Cys Tyr Lys Phe Leu Ala Gln
H.z.  120             Ser                     Lys                         Arg
B.m.          Tyr         Ala     Leu Lys

CAC GCT CTG CGT TGC GAC CCC GAC TAT GTA CCT CAT GAC GTG ATT AGG ATC GTC GAG CCT
A.c.          His Ala Leu Arg Cys Asp Pro Asp Tyr Val Pro His Asp Val Ile Arg Ile Val Glu Pro
H.z.  140             Ala                         Ile         Glu                     Met
B.m.                      --- Gln Asn

TCA TGG GTG GGC AGC AAC AAC GAG TAC CGC ATC AGC CTG GCT AAG AAG GGC GGC GGC TGC
A.c.          Ser Trp Val Gly Ser Asn Asn Glu Tyr Arg Ile Ser Leu Ala Lys Lys Gly Gly Gly Cys
H.z.  160         Tyr                                                         Tyr
B.m.              Tyr         Met

CCA ATA ATG AAC CTT CAC TCT GAG TAC ACC AAC TCG TTC GAA CAG TTC ATC GAT CGT GTC
A.c.          Pro Ile Met Asn Leu His Ser Glu Tyr Thr Asn Ser Phe Glu Gln Phe Ile Asp Arg Val
H.z.  180         Val                     Ala                         Asp         Thr Asn
B.m.                      Ile                                     Ser         Val Asn
                                                                  KpnI
              ATC TGG GAG AAC TTC TAC AAG CCC ATC GTT TAC ATC GGT ACC GAC TCT GCT GAA GAG GAG
A.c.          Ile Trp Glu Asn Phe Tyr Lys Pro Ile Val Tyr Ile Gly Thr Asp Ser Ala Glu Glu Glu
H.z.  200                                                 Val         Ala Ser
B.m.

GAA ATT CTC CTT GAA GTT TCC CTG GTG TTC AAA GTA AAG GAG TTT GCA CCA GAC GCA CCT
A.c.          Glu Ile Leu Leu Glu Val Ser Leu Val Phe Lys Val Lys Glu Phe Ala Pro Asp Ala Pro
H.z.  220                                         Ile     Ile                             ---
B.m.          Gln     Ile                                 Ile

CTG TTC ACT GGT CCG GCG TAT
A.c.          Leu Phe Thr Gly Pro Ala Tyr
H.z.  239         Tyr
B.m.
```

FIG. 2

```
                met pro asp tyr ser tyr arg pro thr ile
5'-AATTCGC      ATG CCG GAT TAT TCA TAC CGT CCC ACG ATC
3'-       GCG  TAC GGC CTA ATA AGT ATG GCA GGG TGC TAG
   Eco RI Sph I                                 Pvu I gly arg thr tyr val tyr asp asn lys tyr
            GGG CGT ACC TAC GTG TAC GAC AAC AAG TAC
            CCC GCA TGG ATG CAC ATG CTG TTG TTC ATG
                                                Sca I tyr lys asn leu gly ala val ile lys asn
            TAC AAA AAT TTA GGT GCC GTG ATC AAG AAC
            ATG TTT TTA AAT CCA CGG CAC TAG TTC TTG
                                        Bcl I ala lys arg lys lys his phe ala glu his
            GCT AAG CGC AAG AAG CAC TTC GCC GAA CAT
            CGA TTC GCG TTC TTC GTG AAG CGG CTT GTA glu ile glu glu ala thr leu asp pro leu
            GAG ATC GAA GAG GCT ACT CTA GAC CCC CTA
            CTC TAG CTT CTC CGA TGA GAT CTG GGG GAT
                                    Xba I asp asn tyr leu val ala glu asp
            GAC AAC TAC CTA GTG GCT GAG              -3'
            CTG TTG ATG GAT CAC CGA CTC CTA G        -5'
                                        Bam HI
```

*FIG. 4*

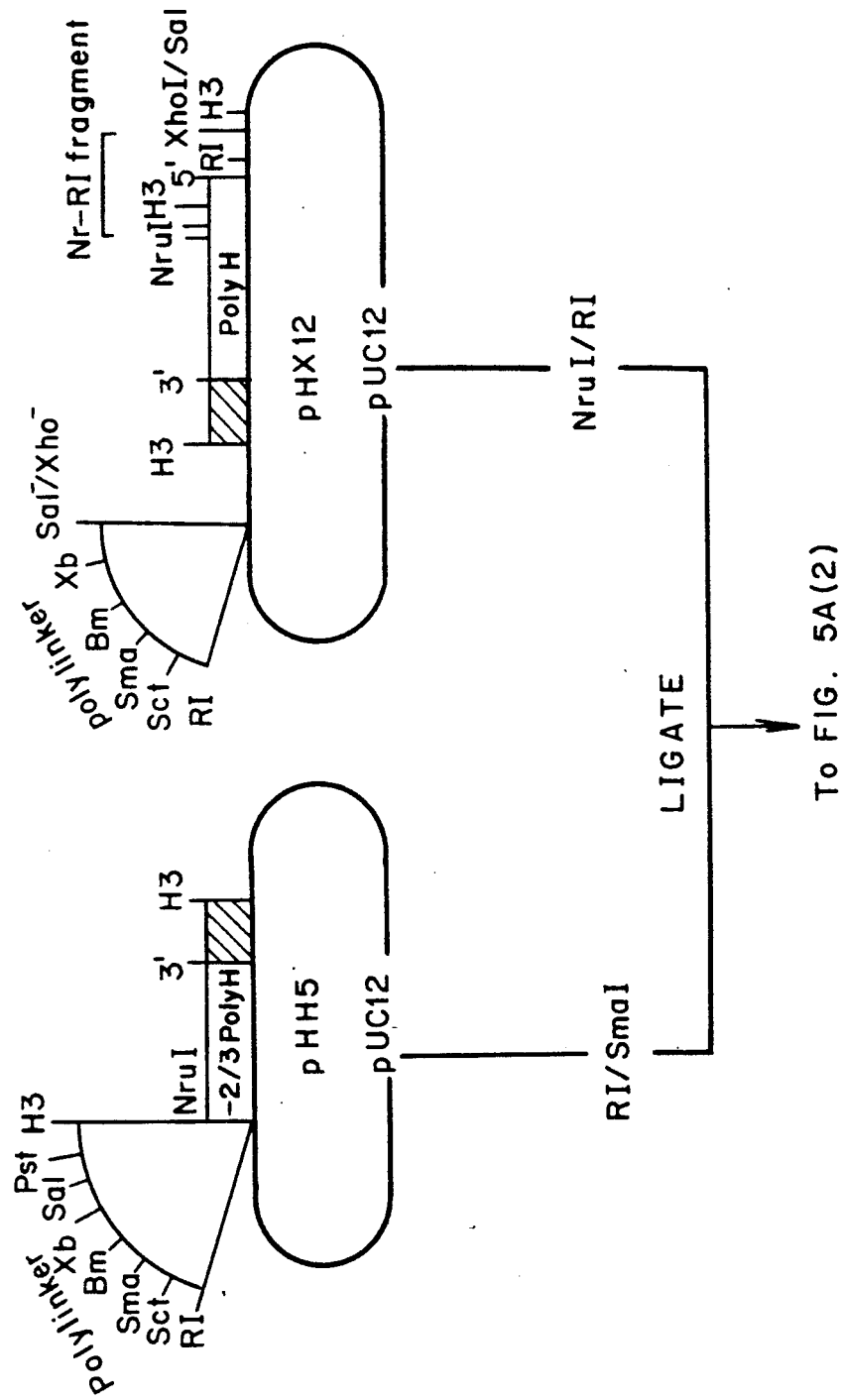
FIG. 5A(1)

FIG. 5A(2)
From FIG. 5A(1)
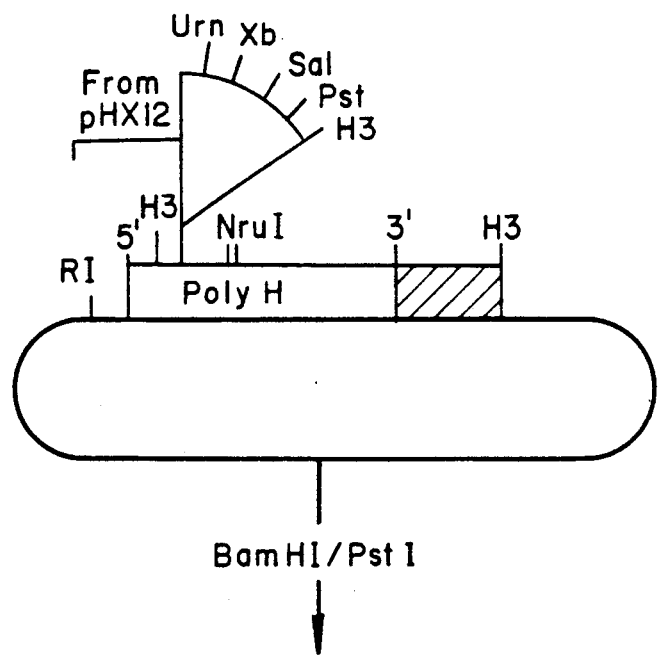
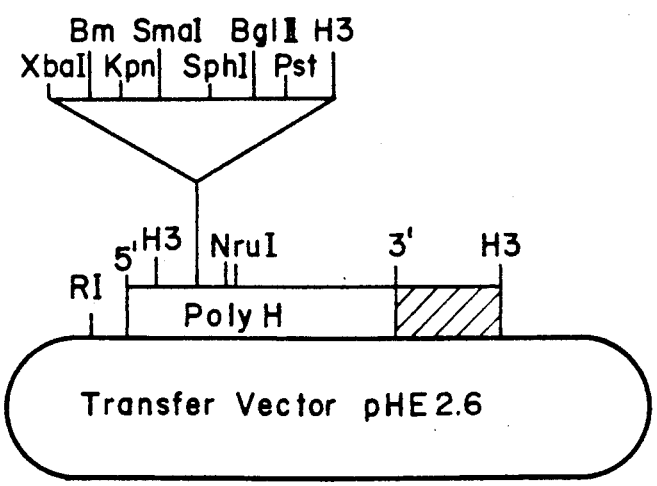

FIG. 8A

| Isolate | Region I | Region II | Region III | Region IV |
|---|---|---|---|---|
| 15 | ⊢ H ⊣ | ⊢ C ⊣ | ⊢ E    F ⊣ | ⊢ K L ⊣ |
|  | 8,31  15,05 | 32,22  42,60 | 69,37  77,67  85,97 | 97,0 00 2,17 |
| W,9,11,12 | ⊢ H ⊣ | ⊢ A'   D' ⊣ | ⊢ B' E'   F ⊣ | ⊢ C' ⊣ |
| 1,2 | ⊢ F'   G' ⊣ | ⊢ A'   D' ⊣ | ⊢ E    F ⊣ | ⊢ C' ⊣ |
| 4 | ⊢ H' ⊣ | ⊢ A'   D' ⊣ | ⊢ E    F ⊣ | ⊢ C' ⊣ |
| 5,7 | ⊢ C'   G' ⊣ | ⊢ A'   D' ⊣ | ⊢ E    F ⊣ | ⊢ C' ⊣ |
| 8,17,18 | ⊢ J'   G' ⊣ | ⊢ A'   D' ⊣ | ⊢ E    F ⊣ | ⊢ K L ⊣ |
| 13 | ⊢ H ⊣ | ⊢ A'   D' ⊣ | ⊢ B' E'   F ⊣ | ⊢ K L ⊣ |
| 14 | ⊢ B' ⊣ | ⊢ A'   D' ⊣ | ⊢ B' E'   F ⊣ | ⊢ C' ⊣ |
| 20,22 | ⊢ H ⊣ | ⊢ A'   D' ⊣ | ⊢ E    F ⊣ | ⊢ C' ⊣ |
| 23 | ⊢ H ⊣ | ⊢ C ⊣ | ⊢ B' E'   K' ⊣ | ⊢ C' ⊣ |
| 24 | ⊢ I'   G' ⊣ | ⊢ A'   D' ⊣ | ⊢ E    F ⊣ | ⊢ C' ⊣ |
| 25 | ⊢ J'   G ⊣ | ⊢ A'   D' ⊣ | ⊢ B' E'   F ⊣ | ⊢ K L ⊣ |
| 21 | ⊢ H ⊣ | ⊢ A'   D' ⊣ | ⊢ E    F ⊣ | ⊢ C' ⊣ |
| 21 | ⊢ M'   K' ⊣ |  |  |  |
| 15 |  | ⊢ D ⊣ |  |  |

FIG. 9

STRUCTURAL PROTEINS OF HzSNPV

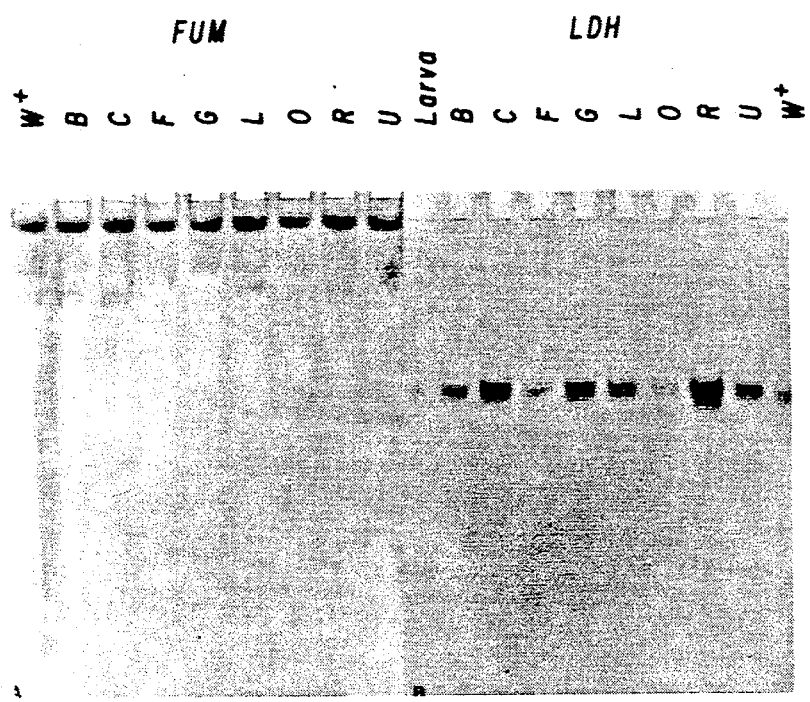
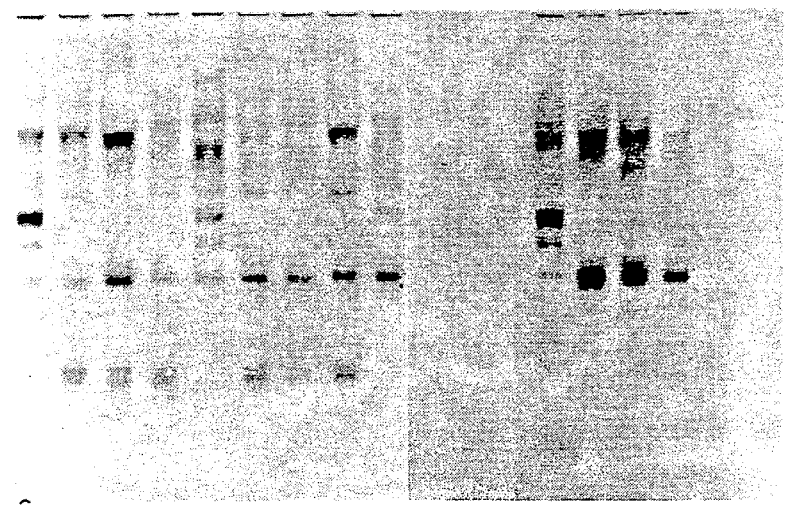
FIG. 11

FIG. 13
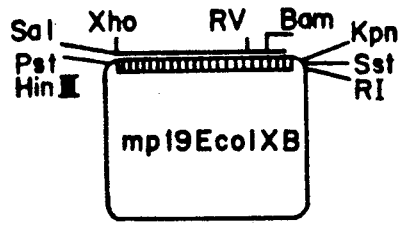
Transcription initiation
```
gatatcatggagataattaaaatgataaccatctcgcaaaggatccgaattcgtcgacggtacc
ctatagtacctctattaattttactattggtagagcgtttcctaggcttaagcagctgccatgg
```
Eco RU                                         Bam  Eco RI  Sal I  Kpn I
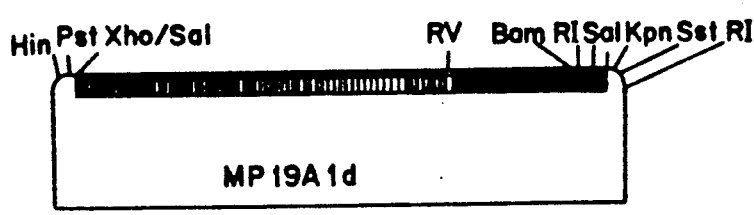
LIGATE
- mp19A1d Hind III/Kpn I
- pUC12 Hind II/Sst I
- pEcoRI-I Kpn I/BamHI
- Oligonucleotide: 5'-GATCAGCT
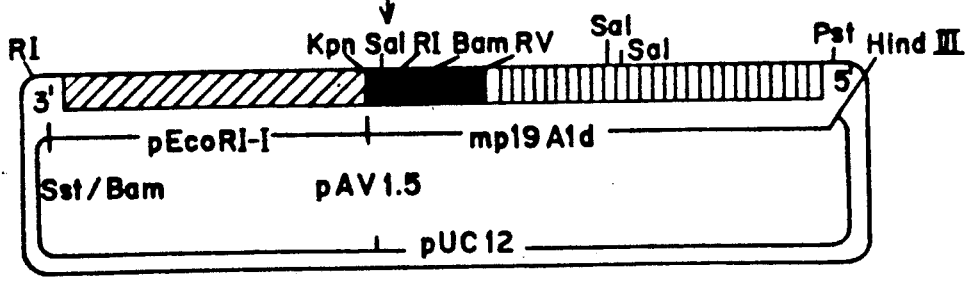

FIG. 15

```
                        Codon for Amino Acid 1 of Autographa Polyhedrin
                                    ↓    HpaⅡ
GTAATAAAAAAACCTATAAATAATGCCGGGATTATTCATACCGTCCC —Sequence from
                                                  mp19 EcoIXB
       Rol-1  ———— GGATATTTATTACGGCCTAATAAG—5'

ATTATCCGTACGATGTACCGGATTACGCGT
       Rol-2                                                    MluI
             5'— ATTTATTACGTAATAGGCATGCTACATGGCCTAATAAGG—
                          NsiI
                 Rol-3
```

Rol-1
————— Rol-2
————— Rol-3

Expression of beta-galactosidase by H. zea Recombinants (cell culture)

Expression of beta-galactosidase by H. zea Recombinants (cell culture)

M  C

Expression of beta-galactosidase by H. zea
Recombinants in Larvae (Coomasie stain)

L1   L2        M

Expression of beta-galactosidase by *H. zea* Recombinants in Larvae (Western blot)

HELIOTHIS EXPRESSION SYSTEMS

The present application is a continuation-in-part of copending application Ser. No. 026,499 filed Mar. 16, 1987, now abandoned.

1. INTRODUCTION

The present invention relates to vector/host cell systems which can direct the expression of heterologous genes controlled by the Heliothis polyhedrin promoter. Using the systems of the present invention, a heterologous gene of interest can be expressed as an unfused peptide or protein, a fusion protein or as a recombinant occlusion body. Recombinant occlusion bodies which contain the heterologous gene product may be particularly useful as vaccines or as insecticide formulations.

2. BACKGROUND OF THE INVENTION

2.1. INSECT VIRUSES AND OCCLUSION BODIES

Baculoviruses are a group of viruses which are pathogenic for insects and some crustaceans. The virions of these viruses contain rod-shaped nucleocapsids enclosed by a lipoprotein membrane. Two morphologically distinct forms of baculovirus are produced by infected cells: the nonoccluded virus and the occluded virus. The nonoccluded virus is synthesized early after infection; nucleocapsids are assembled in the nucleus and acquire an envelope by budding through the plasma membrane to become extracellular virus. In occluded baculoviruses, the virions are embedded in the nucleus in large protein crystals, termed polyhedra or occlusion bodies.

Baculoviruses are members of the family Baculoviridae and the genus Baculovirus. This genus is composed of three subgroups of viruses: the nuclear polyhedrosis viruses (NPV), the granulosis viruses, and the nonoccluded viruses.

NPV have occlusion bodies which are polyhedral to cuboidal in shape, and 1-15 um in diameter. The lipoprotein membranes contain either single nucleocapsids (SNPV) or multiple (up to 39) nucleocapsids (MNPV) per envelope. Up to 100 virions can be embedded in a single occlusion body (Vlak, J. M. and Rohrmann, G. F., 1985, The Nature of Polyhedrin. In Viral Insecticides for Biological Control. Academic Press, pp. 489-542) Examples of this group of viruses include *Autographa californica* NPV (AcNPV), *Heliothis zea* NPV (HzNPV), and *Bombyx mori* NPV (BmNPV). Comparison of DNA sequences of total viral genomes reveals a less than 2% homology between HzSNPV and AcMNPV, whereas a comparison among various MNPVs shows a greater degree of homology (Smith, G. E. and Summers, M. D., 1982, Virol. 123:393-406). HzSNPV is currently produced and sold in the United States for use as an insecticide under the trade name Elcar ™.

The granulosis viruses have round to ellipsoidal occlusion bodies which are 0.1-1 um in size. Each occlusion body contains one singly-enveloped nucleocapsid (Vlak, J. M. and G. F. Rohrmann, supra).

Baculoviruses contain double-stranded, circular DNA molecules, which range from $60-110 \times 10^6$ daltons. The prototype of the Baculoviridae family is AcNPV, which has a genome of approximately $82-88 \times 10^6$ daltons (Miller, L. K., 1981, A Virus Vector for Genetic Engineering in Invertebrates. In Genetic Engineering in the Plant Sciences. Praeger Publishers, New York, pp. 203-224). AcNPV replicates in the nucleus of infected insect cells. Two forms of virus are produced as a result of wild-type AcNPV infection, occluded and non-occluded virions.

The apparent role of the occlusion body in the virus life cycle is to provide stability outside the host insect by protecting the virus from inactivating environmental factors. Ingested occlusion bodies dissolve in the alkaline environment of the midgut, releasing virus particles for another round of infection. The occlusion body consists predominantly of a single, approximately 29,000 dalton molecular weight polypeptide, known as polyhedrin (Vlak, J. M. and Rohrmann, G. F., supra; Miller, L. K, supra). This protein forms the paracrystalline lattice around the virions, and is present as a multimer. Polyhedrin is produced in enormous amounts during the course of viral infection, late after viral replication. As there is no evidence of gene amplification (Tjia, S. T., et al., 1979, Virology 99: 399-409), it is probable that the polyhedrin promoter is an extremely efficient one.

Plaque-purified isolates of *Heliothis zea* SNPV have been characterized, and one such isolate has been cloned (Corsaro, B. G. and Fraser, M. J., 1985, Society for invertebrate pathology, XVIII Annual Meeting, August 4-8, 1985, Ontario, Canada, Abstract 75).

2.2. POLYHEDRIN

The occlusion body (OB) exists as a multimer of the approximately 30 kilodalton polyhedrin polypeptide which forms a paracrystalline lattice around the viral particle (Tinsley, T. W. and Harrap, K. A., 1978, Comprehensive Virology, Vol. 12, Fraenkel-Conrat, H. and R. Wagner (eds.), Plenum Press, New York, pp. 1-101). After alkali dissolution of OBs, a polyhedrin particle with a sedimentation coefficient of 11S-13S (200-374 kilodaltons) can be isolated (Bergold, G. H. and Schramm, G., 1942, Biol. Zentralblatt. 62:105; Bergold, G. H., 1947, Zeitschr. Naturforsch. 2b:122; Bergold, G. H., 1948, Zeitschr. Naturforsch. 3b:338; Harrap, K. A., 1972, Virology 50:124; Eppstein, D. A. and Thoma, J. A., 1977, Biochem. J. 167:321; Rohrmann, G. F., 1977, Biochem. 16:1631). X-ray diffraction studies determined that polyhedrin is crystallized in a body-centered cubic lattice (Engstrom, A., 1974, Biochem. Exp. Biol. 11:7). Electron microscopic analysis of polyhedrin crystals suggests the arrangement of subunits is consistent with six armed nodal units (Harrap, K. A., 1972, Virology 50:124). Crosslinking analysis of polyhedrin utilizing dimethyl suberimidate indicates a dodecameric structure. Therefore, each arm of the nodal unit is composed of two subunits (Scharnhorst, D. W. and Weaver, R. F., 1980, Virology 102:468). Alkali solubility of the crystal suggests that salt bridges are formed between the amino acid side chains. This indicates that the paracrystalline lattice is maintained by noncovalent, ionic intermolecular associations of the individual monomers. Disulfide bond formation may also influence the quaternary structure of the multimeric form.

Baculovirus occlusion body protein has been termed polyhedrin for NPVs and granulin for GVs. However, recent studies have shown that polyhedrins and granulins all belong to one group of related proteins (Rohrmann, G. F., et al., 1981, J. Mol. Evol. 17:329; Smith, G. E. and Summers, M. D., 1981, J. Virol. 39:125). Tryptic peptide analyses have shown that polyhedrins from MNPVs, SNPVs, and GVs have many common fragments (Summers, M. D. and Smith, G. E., 1975, Intervirology 6:168-180; Maruniak, J. E. and Summers, M. D.,1978, J. Invertebr. Pathol. 32:196). Such similarities in sequence can be seen in N-terminal amino acid sequences of polyhedrins from various NPVs and a GV (Vlak, J. M. and Rohrmann, G. F., 1985, The Nature of Polyhedrin. In Viral Insecticides for Biological Control. Academic Press, pp. 489-542.). Some polyhedrins have been found to be more closely related to granulins than to other polyhedrins (Rohrmann, G. F., et al., supra). Thus, hereinafter, the term polyhedrin will be used to refer to the entire group of related proteins.

Comparison of the amino acid sequences of six lepidopteran NPV polyhedrins (Vlak, J. M. and Rohrmann, G. F., supra pp.506-508) reveals that 80-90% of amino acids are conserved within these proteins. There are several regions which can be distinguished on the basis of sequence conservation. For example, amino acids 15-26 and 58-86 are highly conserved. The region between amino acids 38-55 is hydrophilic and highly variable. Other variable sites include the N-terminal region, amino acids 120-127, 145-148, 165, 195, and 216 (Vlak, J. M. and Rohrmann, G. F., supra).

2.3. RECOMBINANT DNA TECHNIQUES AND BACULOVIRUS

The use of recombinant DNA technology for the production of proteins involves the molecular cloning and expression in an appropriate vector of the genetic information encoding the desired proteins. Baculoviruses are useful as recombinant DNA vector systems since they are double-stranded DNA replicating units, into which can be inserted a large amount of foreign DNA (20 megadaltons or more), and which provide at least one strong promoter (polyhedrin) which controls a gene with nonessential function for propagation in cell culture, which is available for replacement or insertion into by foreign NDA (Miller, L. K., 1981, A Virus Vector for Genetic Engineering in Invertebrates, In Genetic Engineering in the Plant Sciences. Praeger Publishers, New York, pp. 203-224; Vlak, J. M. and Rohrmann, G. F., 1985, The Nature of Polyhedrin, In Viral Insecticides for Biological Control, Academic Press, pp. 489-542). A method for the production of recombinant proteins using a baculovirus system has been described (Pennock et al., 1984, Mol. Cell. Biol. 4:399; Smith et al., 1983, J. Virol. 46:584). Baculovirus vectors are constructed, which express foreign DNA which has been inserted into the viral genome. Upon introduction into an appropriate host, the foreign protein is produced.

The expression of foreign DNA in recombinant baculoviruses requires the ligation of baculovirus sequences to a DNA sequence encoding a foreign protein so that the protein-coding sequences are under the control of a promoter. Plasmid vectors, also called insertion vectors, have been constructed to insert chimeric genes into AcNPV. One Example of such an insertion vector is composed of: (a) an AcNPV promoter with the transcriptional initiation site; (b) several unique restriction endonuclease recognition sites located downstream from the transcriptional start site, which can be used for the insertion of foreign DNA fragments; (c) AcNPV DNA sequences (such as the polyhedrin gene), which flank the promoter and cloning sites, and which direct insertion of the chimeric gene into the homologous nonessential region of the virus genome; and (d) a bacterial origin of replication and antibiotic resistance marker for replication and selection in $E.\ coli$. Examples of such vectors are described by Miyamota et al. (1985, Mol. Cell. Biol. 5:2860).

Recombinant baculoviruses have been produced by cotransfection of cells with recombinant bacterial plasmids containing the foreign gene, together with baculovirus DNA. The foreign gene is inserted into or replaces the nonessential polyhedrin gene of the viral genome through homologous recombination within the infected cell. The resulting recombinant plaques can be screened visually for lack of occlusion bodies resulting from the loss of the functional polyhedrin gene. The infected cells can also be screened using immunological techniques, DNA plaque hybridization, or genetic selection for recombinant viruses which subsequently can be isolated. These baculovirus recombinants retain their essential functions and infectivity.

Foreign gene expression can be detected by enzymatic or immunological assays (for example, immunoprecipitation, radioimmunoassay, or immunoblotting). High expression levels can be obtained by using strong promoters or by cloning multiple copies of a single gene.

Several foreign proteins have been successfully expressed in Autographa systems. Human interleukin 2 (Smith et al., 1985, Proc. Natl. Acad. Sci. U.S.A. 82: 8404-8408), human c-myc (Miyamoto et al., 1985, Mol. Cell. Biol. 5:2860-2865), bacterial beta-galactosidase (Pennock et al., 1984, Mol. Cell. Biol. 4:399-406), influenza virus haemagglutinin (Kuroda et al., 1986, EMBO 5: 1359-1365), and human beta-interferon (Smith et al., 1983, Mol. Cell. Biol. 3:2156-2165) have all been expressed in insect cells under the control of the polyhedrin promoter in recombinant AcNPV expression vectors. Human alpha-interferon has been expressed in silkworms by ligation to the polyhedrin promoter of BmNPV (Maeda et at., 1985, Nature (London) 315: 592-594). Smith and Summers (European Patent Application Publication No. 0 127 839, 12-12-84) propose a method for producing recombinant baculovirus expression vectors, and report the use of recombinant AcNPV vectors to express human beta-interferon and human interleukin 2, under the control of the polyhedrin promoter.

2.4. VACCINES FOR VIRAL INFECTIONS

A number of methods are currently in use for the prevention and treatment of viral infections. These include vaccines which elicit an active immune response, treatment with chemotherapeutic agents and interferon treatment.

Traditional ways of preparing vaccines include the use of inactivated or attenuated viruses. Inactivation of the virus renders it harmless as a biological agent but does not destroy its immunogenicity. Injection of these "killed" virus particles into a host will then elicit an immune response capable of neutralizing a future infection with a live virus. However, a major concern in the use of killed vaccines (using inactivated virus) is failure to inactivate all the virus particles. Even when this is accomplished, since killed viruses do not multiply in their host, the immunity achieved is often short lived and additional immunizations are usually required. Finally, the inactivation process may alter the viral proteins rendering them less effective as immunogens.

Attenuation refers to the production of virus strains which have essentially lost their disease producing ability. One way to accomplish this is to subject the virus to unusual growth conditions and/or frequent passage in cell culture. Viral mutants are then selected which have lost virulence but yet are capable of eliciting an immune response. The attenuated viruses generally make good immunogens as they actually replicate in the host cell and elicit long lasting immunity. However, several problems are encountered with the use of live vaccines, the most worrisome being insufficient attenuation.

An alternative to the above methods is the use of subunit vaccines. This involves immunization only with those proteins which contain the relevant immunological material. For many enveloped viruses, the virally encoded glycoprotein contains those epitopes which are capable of eliciting neutralizing antibodies; these include the glycoproteins of La Crosse Virus (Gonzalez-Scarano, F., Shope R. E., Calisher, C. E., and Nathanson, N., 1982, Virology 120:42), Neonatal Calf Diarrhea Virus (Matsuno, S. and Inouye, S., 1983, Infection and Immunity 39:155), Venezuelen Equine Encephalomyelitis Virus (Mathews, J. H. and Roehrig, J. T., 1982, J. Imm. 129:2763), Punta Toro Virus (Dalrymple, J. M., Peters, C. J., Smith, J. F., and Gentry, M. K., 1981, In Replication of Negative Strant Viruses, D. H. L. Bishop and R. W. Compans, eds,. p. 167. Elsevier, New York), Murine Leukemia Virus (Steeves, R. A., Strand, M., and August, J. ., 1974, J. Virol. 14:187), and Mouse Mammary Tumor Virus (Massey, R. J. and Schochetman, G., 1981, Virology 115:20). One advantage of subunit vaccines is that the irrelevent viral material is excluded.

Vaccines are often administered in conjunction with various adjuvants. The adjuvants aid in attaining a more durable and higher level of immunity using smaller amounts of antigen in fewer doses than if the immunogen were administered alone. The mechanism of adjuvant action is complex and not completely understood. However, it may involve the stimulation of phagocytosis and other activities of the reticuloendothelial system as well as a delayed release and degradation of the antigen. Examples of adjuvants include Freund's adjuvant (complete or incomplete), Adjuvant 65 (containing peanut oil, mannide monooleate and aluminum monostearate), the pluronic polyol L-121, Avridine, and mineral gels such as aluminum hydroxide, aluminum phosphate, or alum. Freund's adjuvant is no longer used in vaccine formulations for humans because it contains nonmetabolizable mineral oil and is a potential carcinogen.

2.5. VACCINES FOR PARASITIC AND BACTERIAL INFECTIONS

The development of vaccines for the prevention of parasitic or bacterial diseases is the focus of much research effort. Vaccines are presently available for diphtheria, pertussis, and tetanus (Warren, K. S., 1985, In Vaccinnes85, Lerner, R. A., R. M. Chanock, and F. Brown (eds.), Cold Spring Harbor Laboratory, New York, pp. 373-376). In addition, a vaccine consisting of the polysaccaride capsule of Hemophilus influenzae was recently licensed, although it is ineffective in preventing disease in certain subgroups of the population (Granoff, D. M. and Munson, R. S., Jr., 1986, J. Infect. Dis. 153:448-461). No vaccines currently exist for any of the many protozoan infections such as malaria or helminth infections such as schistosomiasis and ascariasis. The protective effects of antisera directed against epitopes of Escherichia coli toxins, cholera toxins, gonococcal pili, and malaria surface antigens (Vaccines85, 1985, Lerner, R. A., R. M. Chanock, and F. Brown (eds.), Cold Spring Harbor Laboratory, New York; Modern Approaches to Vaccines, 1984, Chanock, R. M., and R. A. Lerner (eds.), Cold Spring Harbor Laboratory, New York) are among the many systems presently under investigation.

3. SUMMARY OF THE INVENTION

The present invention relates to recombinant vector/host systems which can direct the expression of foreign genes under the control of the Heliothis polyhedrin promoter. The host systems of the present invention include, but are not limited to, cultured cells, larvae, or microorganisms. The present invention provides for the expression of the heterologous gene of interest, under the control of the Heliothis polyhedrin promoter, as an unfused peptide or protein, a fusion protein, or as a recombinant occlusion body which comprises crystalized polyhedrin fusion proteins which contain the heterologous gene product on the surface of or within the occlusion body. Where the heterologous gene product comprises an epitope of a pathogenic microorganism, the recombinant protein or occlusion body of the present invention can be particularly useful in vaccine formulations. In another embodiment of the invention, the foreign sequence can encode a molecule with insecticidal activity. The vector/host systems of the present invention can be used as expression systems for the production of the foreign peptide or protein expressed under the control of the Heliothis promoter. The recombinant proteins of the invention or fragments thereof which comprise antigenic determinants also have uses in immunoassays.

3.1 DEFINITIONS

The following terms and abbreviations have the meanings indicated:
Ac = Autographa californica
Hz = Heliothis zea
ECV = extracellular virus
poly H = polyhedrin
Isozymes:
 EST = esterase
 FUM = fumarate hydratase
 LDH = lactate dehydrogenase
 MDH = malate dehydrogenase
Buffers:
 TE = 10 mM Tris-HCl, 1mM EDTA, pH 7.6
 TBE = 81.2 mM Tris, 20 mM boric acid, 1.5 mM EDTA, pH 8.9
 TC = 9.7 mM Tris, 2.13 mM citric acid, pH 7.1
OB = Occlusion Body, a paracrystalline protein matrix which occludes baculovirus virions. The paracrystalline protein matrix forms a refractile body which is polyhedral, cuboidal or spherical in shape.
The term OB will also be used hereinafter to refer to lattices formed in vitro by the recrystallization of soluble polyhedrin.
NPV = Nuclear Polyhedrosis Viruses, a subgroup of the baculovirus genus in which the nucleocapsids are enveloped by a lipoprotein membrane singly (SNPV) or in multiples (MNPV) per common envelope. Up to 100 of these virion packages are embedded in an occlusion body, polyhedral to cuboidal in shape and 1-15 um in diameter.
GV = Granulosis Virus, a subgroup of the baculovirus genus in which one singly-enveloped nucleocapsid is embedded per occlusion body, round to ellipsoidal in shape and 0.1-1 um in size.

NOBV=Non-occluded baculoviruses.

MCS=Multiple cloning site. A region of DNA containing a series of unique restriction endonuclease cleavage sites.

SDS-PAGE=sodium dodecylsulfate polyacrylamide gel electrophoresis.

Cassette Transfer Vector=A transfer vector comprising the Heliothis polyhedrin promoter and a restriction enzyme recognition site into which a heterologous gene sequence can be inserted under the control of the polyhedrin promoter, in which the Heliothis polyhedrin promoter and the restriction site are flanked by sequences that are homologous to parent vector sequences. Heterologous gene sequences can be inserted into the cassette transfer vectors which can then be used to construct recombinant expression vectors via homologous recombination in vivo with a parent vector.

Transfer Vector=A transfer vector comprising the Heliothis polyhedrin promoter and a heterologous gene sequence positioned under the control of the polyhedrin promoter, in which the polyhedrin promoter and the heterologous gene sequences are flanked by sequences that are homologous to parent vector sequences. The transfer vector containing the heterologous gene sequence can be used to construct recombinant expression vectors via homologous recombination in vivo with a parent vector.

Cassette Expression Vector=An expression vector comprising the Heliothis polyhedrin promoter and a restriction enzyme recognition site into which a heterologous gene sequence can be inserted under the control of the polyhedrin promoter so that the gene is expressed in a suitable host.

Expression Vector=An expression vector comprising the Heliothis polyhedrin promoter and a heterologous gene sequence positioned under the control of the polyhedrin promoter so that the heterologous gene is expressed in a suitable host.

4. DESCRIPTION OF THE FIGURES

FIG. 1. Nucleotide sequence of the gene of *Heliothis zea*. The nucleotide sequence was determined using the dideoxy chain termination method of Sanger et al. (1977, Proc. Natl. Acad. Sci. U.S.A. 74:5463). The deduced amino acid sequence is presented below the nucleotide sequence.

FIG 1A. Restriction map of the Heliothis polyhedrin gene. A restriction endonuclease digestion map of the Heliothis polyhedrin gene for the restriction endonucleases HindIII, NruI, HincII, and AccI is presented. The map was derived from the nucleotide sequence shown in FIG. 1. Numbers in parentheses represent the number of the nucleotide in FIG. 1.

FIG. 1B. Nucleotide sequencing strategy of the Heliothis polyhedrin gene. The sequencing strategy used in the dideoxy chain termination method (Sanger, F., et al., 1977, Proc. Natl. Acad. Sci. U.S.A. 74:5463–5467) of sequencing of the Heliothis polyhedrin gene is depicted. The arrows indicate the direction of sequencing on each fragment. The following abbreviations are used in the figure; Xho (XhoI), Sal (SalI), RI (EcoRI), H3 (HindIII), HII (HindII), and Nr (NruI).

FIG. 2. Homology of amino acid sequences of polyhedrin genes of *Autographa californica* MNPV (Ac), *Heliothis zea* SNPV (Hz) and Bombyx mori NPV (Bm). The DNA and deduced amino acid sequence of the polyhedrin gene of Ac is presented (Hooft van Iddekinge, B. J. L., et al., 1983, Viology 131:561). The differences between the deduced amino acid sequence of the Ac polyhedrin and that of Bm (Kozlov, E. A., et al., 1981, Biiorg. Khim 7:1008) and Hz (see FIG. 1supra), are indicated. Where an amino acid is present in one sequence and absent from another, the missing amino acid is indicated by the following symbol: ----.

FIG. 3. Hydrophobicity profile of Hz and Ac polyhedrin. The hydrophobicity of each amino acid residue as measured by Hopp and Woods (1981, Proc. Natl. Acad. Sci. U.S.A. 78:3824) was plotted against the amino acid residue number of the polyhedrin gene. The amino terminus and amino acid residues 35-50, were identified as hydrophilic regions of the Heliothis polyhedrin molecule.

FIG. 4. Polyhedrin polylinker sequence. A synthetic polylinker gene sequence and its encoded amino acids are depicted. This gene segment encodes the *Autographa californica* polyhedrin gene extending from the amino terminus to the BamHI site corresponding to amino acid 58. Restriction endonuclease digestion sites are indicated below the DNA sequence. The PvuI, ScaI, BclI, and XbaI sites correspond to amino acids 9, 19, 27, and 46, respectively.

FIG. 5A. Is a diagrammatic representation of the construction of cassette vector pHE2.6, which can be used to insert foreign genes within the polyhedrin gene and to produce Hz viruses via in vivo recombination. These Hz recombinants, when placed in an appropriate host system, will express the foreign gene under the control of the polyhedrin promoter. The following abbreviations are used in the figure: polyH (Heliothis polyhedrin gene sequence), RI (EcoRI), Sst (SstI), Sma (SmaI), Bm (BamHI), Xb (XbaI), Sal (SalI), Pst (PstI), H3 (HindIII), Nr (NruI), and Xho (XhoI).

FIG. 5B. Is a diagrammatic representation of the construction of transfer vector pHE2.61ac, which contains a functional *E. coli* beta-galactosidase gene. pHE2.61ac can be used to produce recombinant Heliothis viruses via in vivo recombination, which express the beta-galactosidase gene under the control of the Heliothis polyhedrin promoter. The following abbreviations are used in the figure: Xba (XbaI), Bam (BamHI), Kpn (KpnI), Sma (SmaI), Oligo (oligonucleotide), and MCS (multiple cloning site).

FIG. 5C. Is a diagrammatic representation of the construction of transfer vectors which contain deletions in the amino-terminal coding region of the Heliothis polyhedrin gene. These transfer vectors can be used to insert foreign genes within the polyhedrin gene and to produce Hz viruses via in vivo recombination. The following abbreviations are used in the figure: xba (XbaI), bam (BamHI), kpn (KpnI), sma (SmaI), sph (SphI), bgl (BglI), and pst (PstI).

FIG. 6. Restriction endonuclease analysis of the HzSNPV Elcar TM isolate and plaque-purified strains. Viral DNAs were purified from sucrose gradient-purified occluded virions, digested with HindIII, and fractionated on a 0.75% agarose gel, as described infra. Numerous differences were apparent between the wild-type Elcar TM isolate (W+) and plaque purified strains (1–25)- We chose HzS-15 as the standard for our analyses, and characterized all other strains relative to that digestion pattern. Most of the strains were lacking the 13.2 kb HindIII-C, the 3.83 kb HindIII-K, and the 2.76 kb HindIII-L fragments of HzS-15. Most strains had additional HindIII fragments at 10.24, 6.6, and 3.26 kb that hybridized to the HindIII-C, K, and L fragments of HzS-15.

Figure 7:
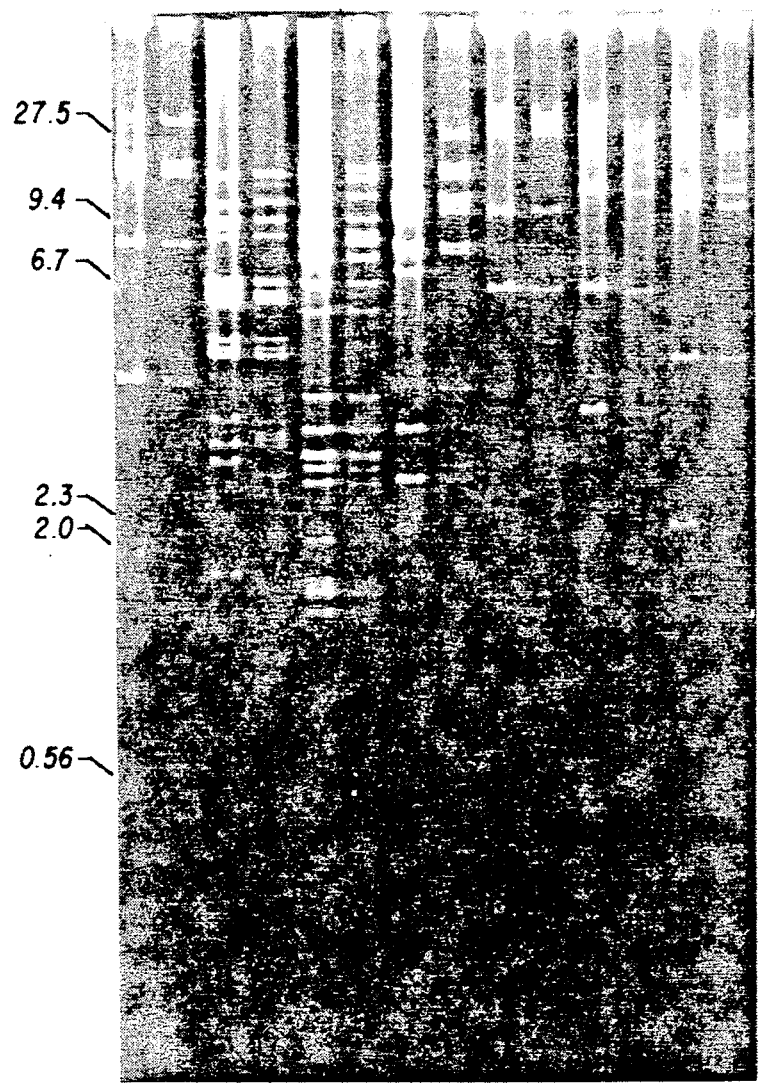

FIG. 7. Genotypic comparison of the Elcar TM isolate and the HzS-15 strain. The wild-type Elcar TM isolate (w+) and the plaque-purified HzS-15 strain were digested with enzymes BamHI, EcoRI, EcoRV, HindIII, KpnI, PstI, and SstI, and fractionated on a 0.75% agarose gel. The fragment patterns for BamHI, KpnI, and PstI are identical while those of EcoRI, EcoRV, HindIII, and SstI are distinct.

Figure 8:
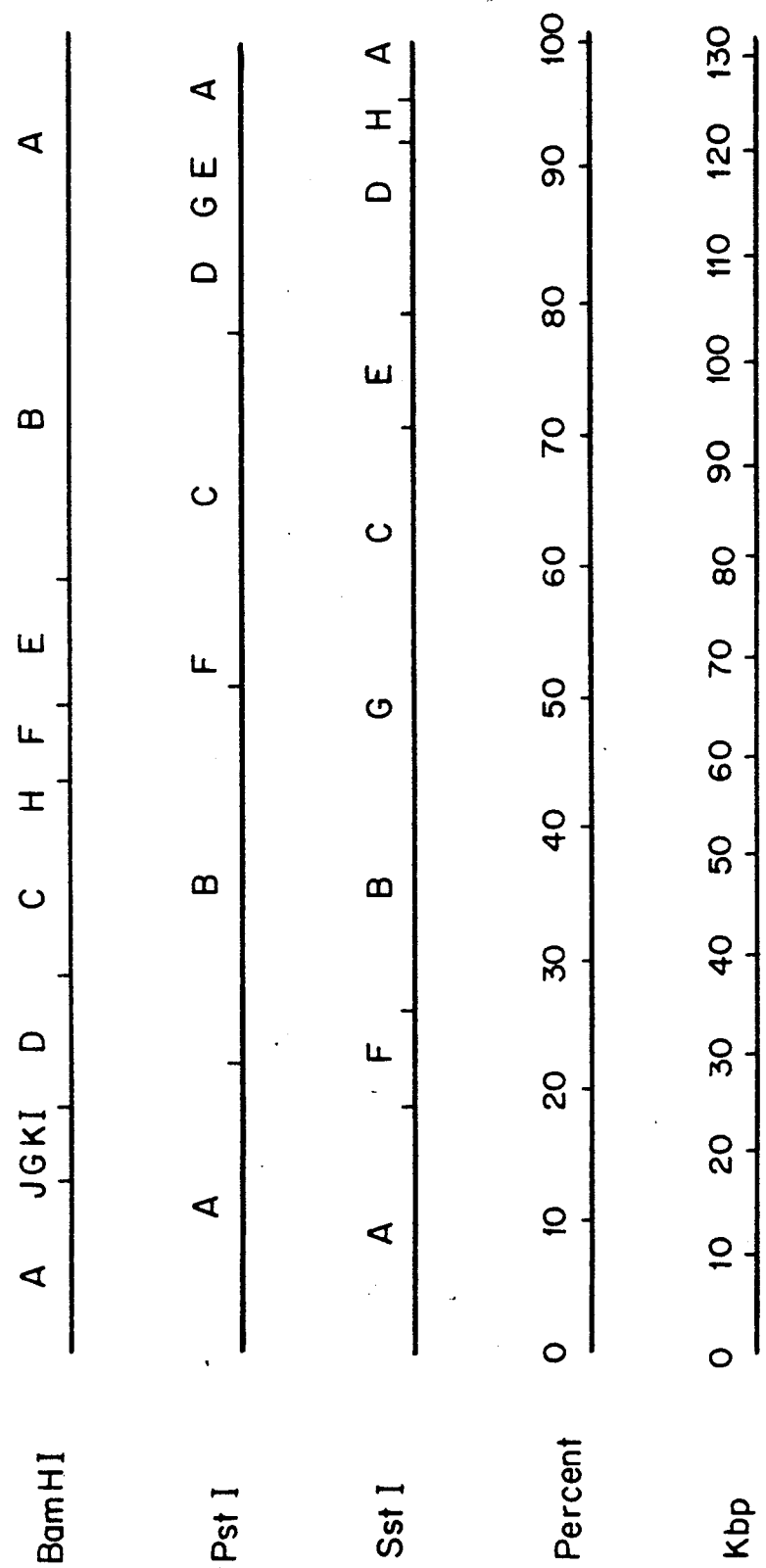

FIG. 8. Physical map of the HzSNPV viral genome. The linear genomic map was constructed from hybridization analyses of the plaque-purified strain, HzS-15, using cloned BamHI, HindIII, and PstI fragments as probes for genomic restriction enzyme digestions. Our map deviates from the previous map of Knell and Summers (1984, J. Gen. Virol. 65:445–450), particularly in the placement of HindIII-B and J, and BamHI-G, I, J, and K fragments.

FIG. 8A. Analysis of the four variable regions of the HzSNPV genome. Regions of genomic variability among the HzSNPV plaque-purified strains were determined through hybridization analysis with cloned HzS-15 fragments. Regions II, III, and IV encompassed conservative alterations in each of the viral isolates. The HzS-23 genotype contained a small insertion of undetermined origin in HindIII-F of Region III. Most of the plaque-purified genotypes with changes in Region I had small insertions or deletions in HindIII-H, while one genotype (exhibited by HzS strains 1 and 2) had no significant alterations in fragment size. HzS-21 contained a small insertion in HindIII-D in addition to alterations in Regions II and IV.

Figure 9:
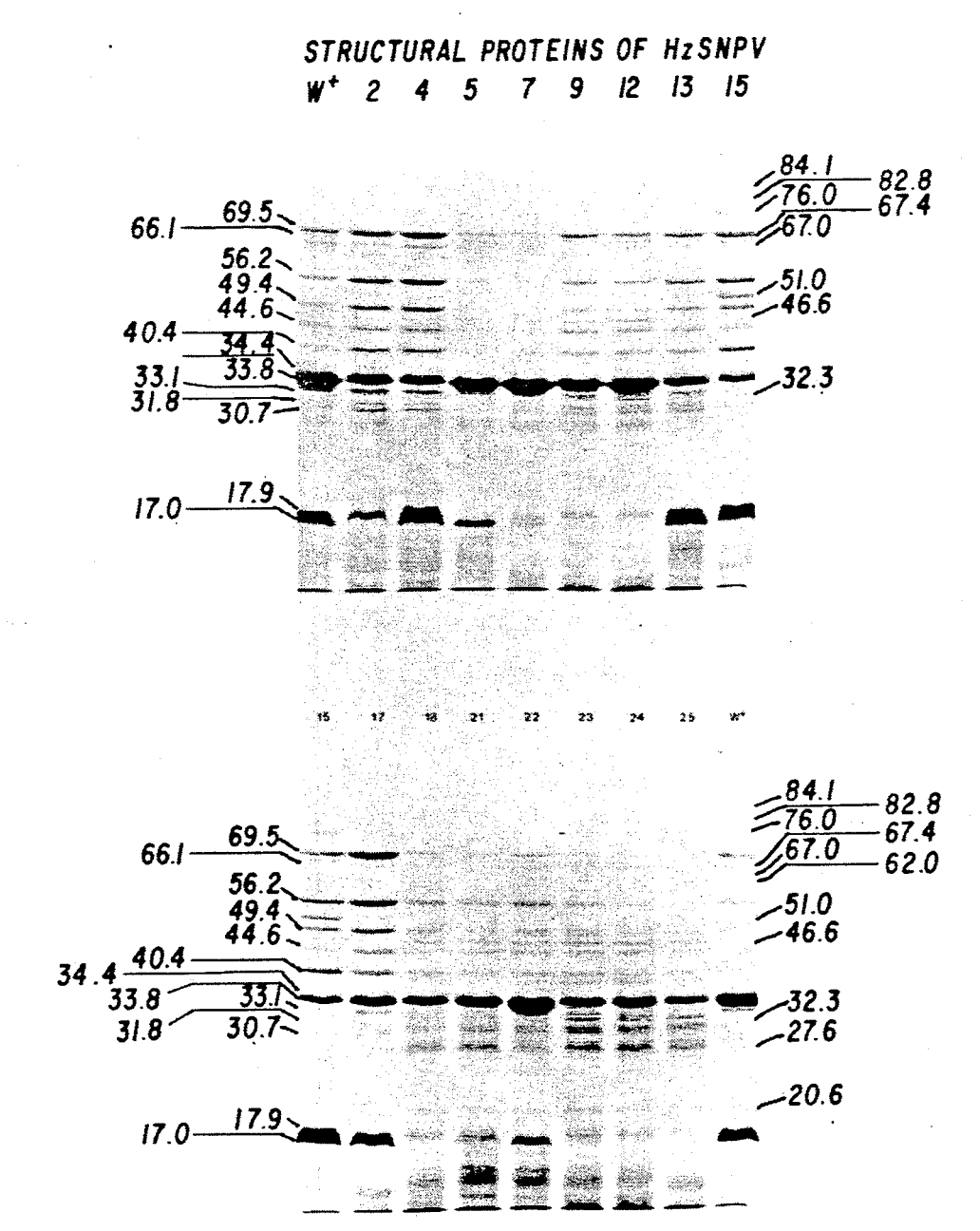

FIG. 9. Occluded virion structural proteins of HzSNPV Elcar TM isolate and plaque-purified strains. Gradient purified virions were electrophoresed at 30 milliamperes for 4.5 hours on a $10 \times 10$ cm, 12% SDS-polyacrylamide gel. The position and size of major wild-type proteins are labeled on the left, while unique proteins found in several of the plaque-purified strains are labeled on the right.

Figure 10:
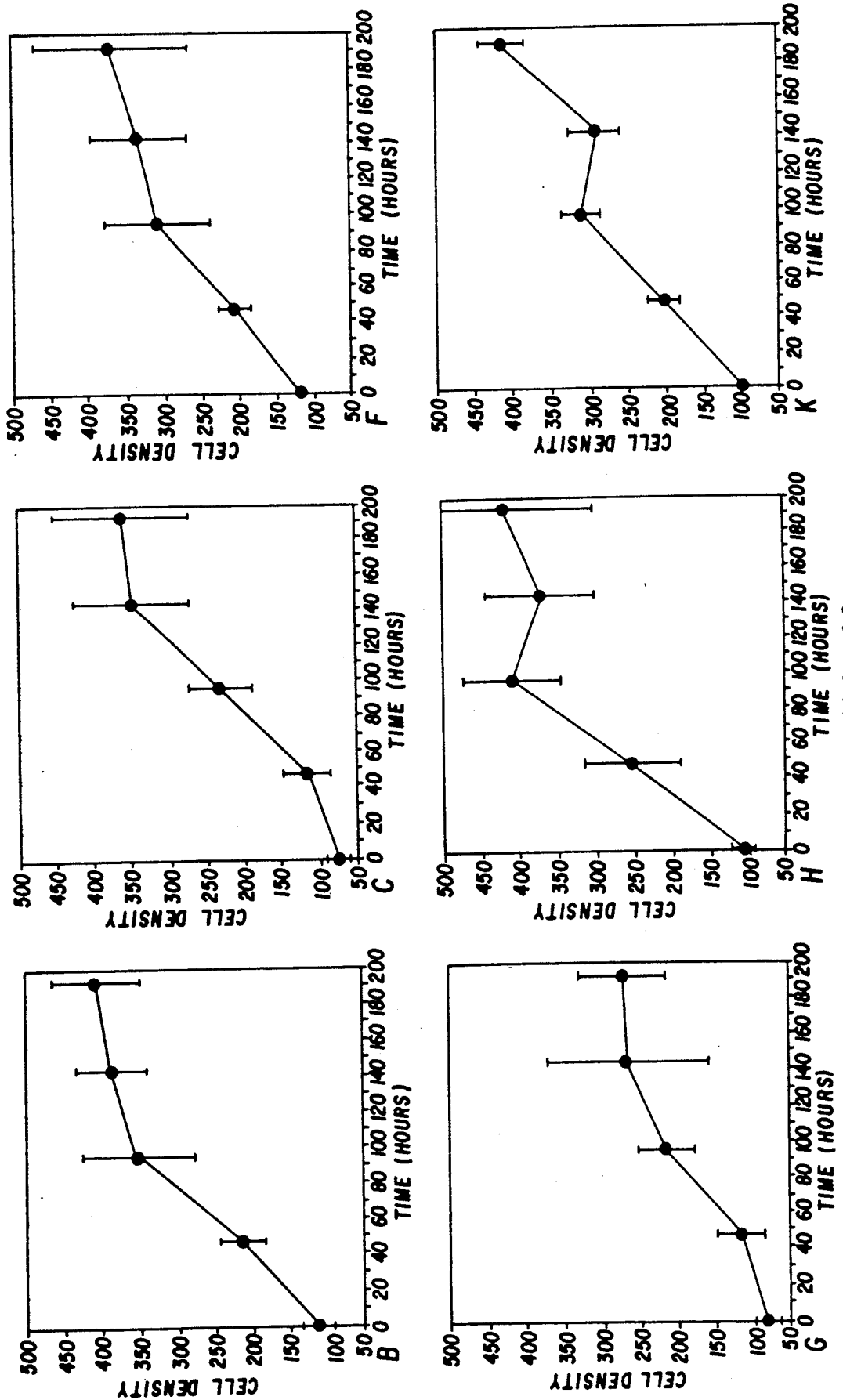
Figure 10:
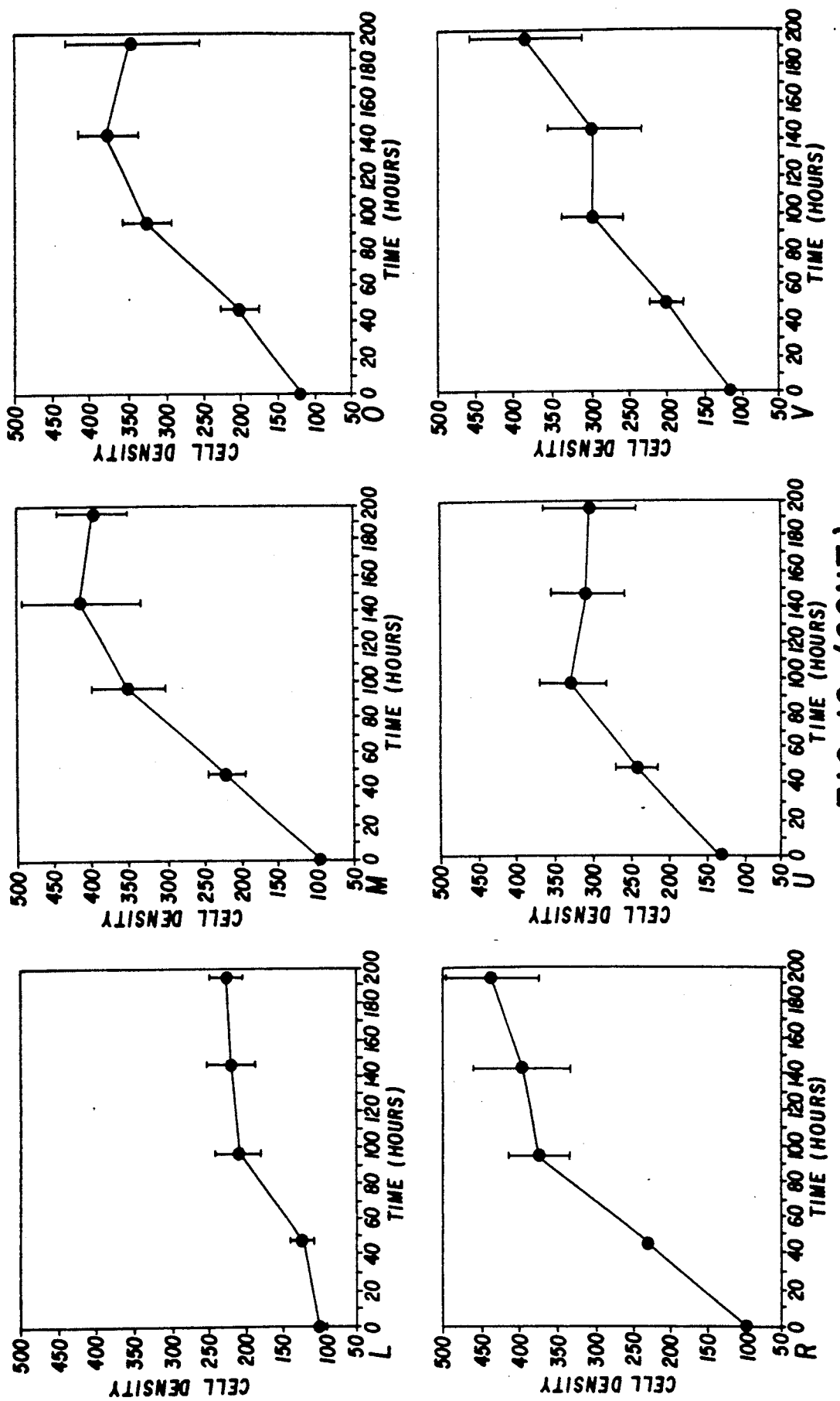

FIG. 10. Cell growth curves for clonally isolated cell strains derived from IPLB-HZ1075. Three defined regions of a tissue culture flask (25 cm$^2$) were counted at 48 hour intervals for a total of 8 days. Points on the graphs represent the average of the three counted areas with the error bars indicating 1 standard deviation. Letters in the lower left corner of each graph correspond to the nomenclature of the specific cell strain.

FIG. 11. Comparison of isozyme banding patterns between all IPLB-HZ1075 derived cell strains and Heliothis zea larvae with isozymes FUM, LDH, and EST. Cell and larval extracts were electrophoresed in a 5% polyacrylamide gel (95% acrylamide, 5% bis-acrylamide) in either TBE or TC buffer, and stained for the appropriate enzyme. Staining for FUM and for LDH confirms that the cell strains were derived from the parental IPLB-HZ1075 (W+) cell line and that they are ultimately derived from Heliothis zea larvae. The differences in the EST gels suggest that all of the strains are not identical. Staining procedures for the isozymes are described infra. A) FUM = Fumarate Hydratase B) LDH = Lactate Dehydrogenase C) EST = Esterase.

Figure 12A:
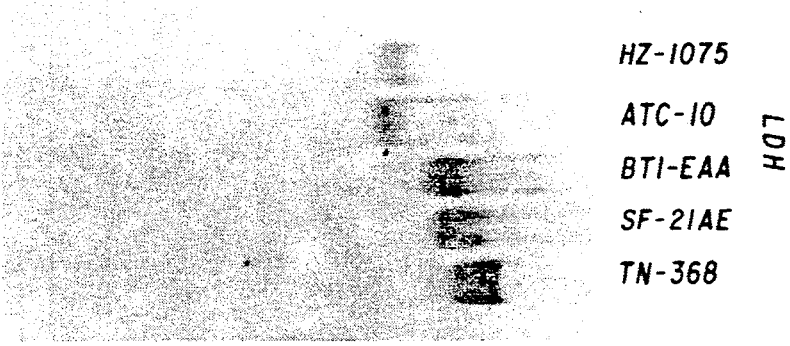
Figure 12B:

FIG. 12. Comparison of isozyme banding patterns for several insect cell lines. Cell lines prepared as described were electrophoresed in a 5% polyacrylamide gel (95% acrylamide, 5% Bis-acrylamide) in TC buffer. LDH separates IPLB-HZ1075 from all other cell lines; however, ATC-10 and IPLB-HZ1075 differ by an Rf value of only 0.03. MDH clearly separates IPLB-HZ1075 from ATC-10 and also BTI-EAA from IPLB-SF-21AE which co-migrated when stained with LDH. Staining procedures are described infra.

Figure 16:
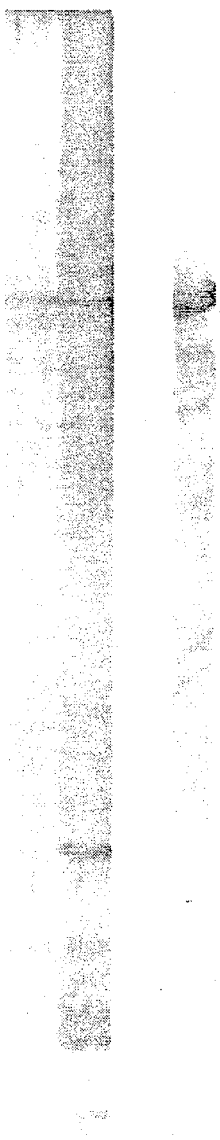

FIG. 13. Is a diagrammatic representation of the construction of cassette vector pAV1.5 which can be used to insert foreign genes within the Autographa polyhedrin sequence which can then be transferred to the Autographa virus genome via in vivo recombination. pAV1.5 can also be used for further genetic manipulations, such as insertion of the Heliothis polyhedrin gene, as shown in FIG. 16. The following abbreviations are used in the figure: RI (EcoRI), Sst (SstI), Bam (BamHI), Kpn (KpnI), Sal (SalI), RV (EcoRV), Pst (PstI), H3 (HindIII), and Xho (XhoI).

Figure 14:
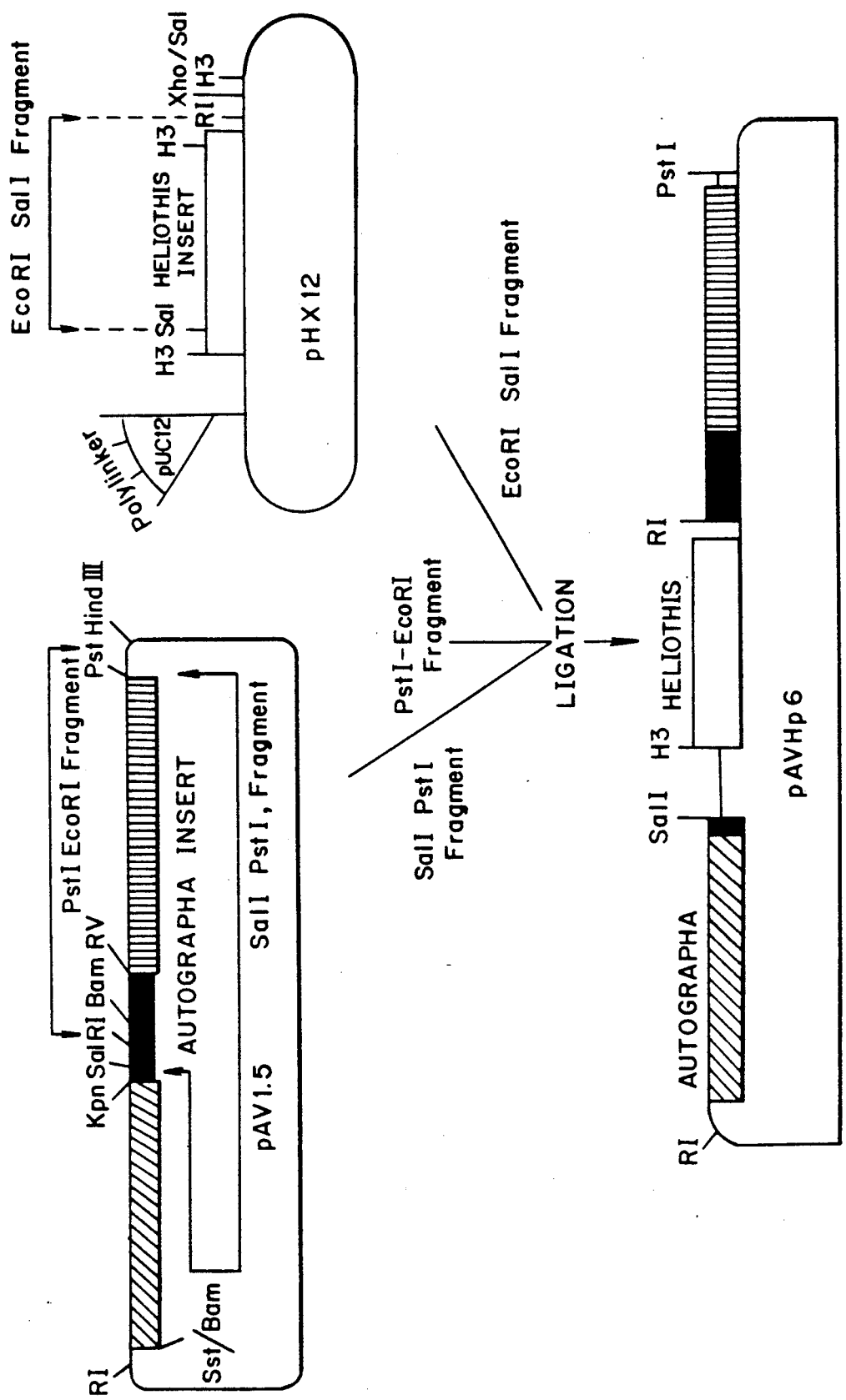

FIG. 14. Is a diagrammatic representation of the construction of cassette vector pAVHp6, which can be used to insert foreign genes within the Heliothis and/or the Autographa polyhedrin genes, and which can be used to transfer such foreign genes into Autographa virus by in vivo recombination. The following abbreviations are used in the figure: Sst (SstI), Bam (BamHI), RI (EcoRI), Kpn (KpnI), Sal (SalI), RV (EcoRV), Pst (PstI), H3 (HindIII), and Xho (XhoI).

FIG. 15. Is a diagrammatic representation of the construction of a transfer vector containing a foreign DNA sequence encoding amino acids 98–106 of the influenza hemagglutinin inserted at a specific HpaII site within the Autographa polyhedrin gene.

FIG. 16. Photomicrographs of a Western blot of a 7.5% polyacrylamide gel of cell proteins from cells of a 24-well plate, infected with a recombinant Heliothis virus expressing B-galactosidase. Lane 1 was loaded with a lysate of $1 6 \times 10^4$ cells infected with HzS15Bgal-D4 (from cells of well 1). Lane 2 was loaded with $3.2 \times 10^4$ cells infected with HzS15Bgal-D4 (from cells of well 2). Lane M (control marker) contained 10 ug of B-galactosidase (110,000 molecular weight) from Bio-Rad.

Figure 17:

FIG. 17. Photomicrographs of a Western blot of a 9% polyacrylamide gel of cell proteins from cells of a 24-well plate, infected with a recombinant Heliothis virus expressing B-galactosidase. Lane C was loaded with a lysate of $0.5 \times 10^4$ cells infected with HzS15Bgal-D4 (from cells of well 5), and Lane M (control marker) was loaded with 10 ug of B-galactosidase (110,00 molecular weight) from Bio-Rad.

Figure 18:

FIG. 18. Coomassie blue-stained 9% polyacrylamide gel of proteins from H. zea neonate larvae (1–3 mg total weight) infected with recombinant Heliothis virus HzS15Bgal-D3. Lane L1 was loaded with 6.2 ug of extract from an infected neonate, containing 518.4 Units B-galactosidase activity per mg protein. Lane L2 was loaded with 6.0 ug of extract from a second infected neonate, containing 540.0 Units B-galactosidase activity per mg protein. Lane M (control marker) contained 10 ug of B-galactosidase (110,000 molecular weight) from Bio-Rad. The only visible bands in Lane L are those that migrate where the recombinant B-galactosidase protein is expected.

Figure 19:

FIG. 19. Photomicrograph of a Western blot of a 9% polyacrylamide gel of proteins from a H. zea neonate larva (2 mg total weight) infected with the recombinant Heliothis virus HzS15Bgal-D3. Lane L was loaded with 5.4 ug of extract from an infected neonate, containing 1563.8 Units B-galactosidase activity per mg protein.

Lane M (control marker) contained 10 ug of B-galactosidase (110,000 molecular weight) from Bio-Rad. Based on the relative staining of the marker and the larval extract protein, we can conclude that the recombinant B-galactosidase protein constituted greater than 0.1% of the larval wet weight.

5. DETAILED DESCRIPTION OF THE INVENTION

The present invention relates to recombinant vector/host systems which can direct the expression of heterologous genes controlled by the Heliothis polyhedrin promoter in different host systems including, but not limited to cultured cells, larvae or microorganisms. Using the systems of the present invention, the heterologous gene may be manipulated so that the gene product will be expressed as an unfused peptide or protein, a fusion protein or as a recombinant occlusion body which comprises cystallized polyhedrin fusion proteins which bear the heterologous gene product on the surface of or within the occlusion body. The expression products have a number of uses, and the present invention offers particular advantages in the production of vaccine formulations.

For purposes of clarity in discussion, the subsections below describe the expression vector/host systems of the invention in terms of the following components: (a) manipulations of the Heliothis polyhedrin gene so that the heterologous gene is placed under the control of the Heliothis polyhedrin promoter so that the gene products are expressed as unfused peptides or proteins, fusion proteins or as recombinant occlusion bodies; (b) Heliothis virus expression vectors and Heliothis parent viruses that can be used to make Heliothis virus expression vectors; (c) Heliothis cell lines which can be used in the construction of recombinant Heliothis viruses, the propagation of recombinant Heliothis viruses and/or for the expression of the heterologous gene product; and (d) Heliothis larvae which can be used for propagating the recombinant Heliothis viruses and/or for mass production of the heterologous gene product.

Other systems which provide for the expression of the heterologous gene under the control of the Heliothis polyhedrin promoter in non-Heliothis insect hosts and in microorganisms such as bacteria are described as well.

Methods for the isolation and purification of the heterologous gene product are described as are different vaccine formulations in accordance with the invention.

5.1. MANIPULATING THE HELIOTHIS POLYHEDRIN GENE AND PROMOTER TO EXPRESS DIFFERENT GENE PRODUCTS

The DNA sequence of the *Heliothis zea* polyhedrin gene was determined using the dideoxy method of Sanger (1977, Proc. Natl. Acad. Sci. U.S.A. 74: 5463) and is presented in FIG. 1, which also indicates the deduced amino acid sequence. In accordance with the invention, a number of manipulations are possible in order to place a heterologous gene under the control of the Heliothis polyhedrin promoter. Different kinds of gene products will be expressed depending upon the manner in which the polyhedrin gene is manipulated. Such manipulations include, but are not limited to the following:

(a) All or substantially all of the Heliothis polyhedrin gene sequence can be replaced with the heterologous gene of interest, so that the heterologous gene is placed under the control of the polyhedrin promoter. The heterologous gene product will be expressed at high levels by such recombinant Heliothis virus/host systems of the present invention.

(b) Portions of the Heliothis polyhedrin gene sequence can be replaced by all or portions of the heterologous gene of interest. If the heterologous gene is in the same translational reading frame as the polyhedrin gene, uninterrupted by sequences which encode translational stop signals, then a fusion protein will be expressed by the recombinant Heliothis virus/host systems of the present invention. Convenient restriction sites which may be used for this purpose include but are not limited to HindIII and NruI as shown in FIG. 1.

(c) The Heliothis polyhedrin gene can be engineered so that specific portions of the polyhedrin gene sequence which encode regions of the polyhedrin protein that are not required for crystallization are replaced in whole or part by all or portions of the heterologous gene of interest. Regions that are nonessential for crystallization should be variable when compared to other polyhedrin sequences. If the inserted heterologous sequence is in the same translational reading frame as the polyhedrin gene, uninterrupted by sequences which encode translational stop signals, then a fusion protein will be expressed which is capable of crystallizing and forming occlusion bodies (herein referred to as recombinant OBs). The recombinant OBs formed by these polyhedrin fusion proteins will comprise OB crystals that present the heterologous gene product on the surface of or within the OB crystal. The production of the recombinant polyhedrin crystals can thus facilitate the isolation of its component heterologous gene product, in substantially pure form.

The recombinant OBs may be particularly useful for the production of vaccines. In a preferred embodiment of this aspect of the invention, the heterologous sequence can be inserted into or replace portions of the polyhedrin gene which encode hydrophilic regions of the polyhedrin protein, which are likely to be surface domains. These compositions may be especially advantageous when the heterologous protein to be used in a vaccine formulation is a hapten (i.e., a molecule that is antigenic but not immunogenic) which ordinarily must be coupled to a carrier molecule that confers immunogenicity. The production of recombinant OBs carrying the heterologous hapten on their surface using the expression vector/host systems of the present invention would render the molecule immunogenic and eliminate chemical coupling reactions. Sequences of the polyhedrin gene which encode hydrophobic regions of the polyhedrin protein may also be inserted into or replaced by heterologous sequences so that a recombinant OB is produced that is useful in a vaccine formulation.

As explained in more detail, infra, the recombinant OBs may be solubilized and recrystallized so that (a) the enveloped recombinant Heliothis virions can be removed from the solubilized recombinant OBs which can then be recrystallized without the recombinant Heliothis virus; and/or (b) a mixture of recombinant OBs, each of which bears a different heterologous protein, can be solubilized and recrystallized. The resulting OBs would bear each of the heterologous proteins and would be particularly useful as a multivalent vaccine.

In order to identify the portions of the polyhedrin gene sequence that are likely to encode surface domains which can be replaced by the heterologous gene sequence in accordance with this embodiment of the invention, we identified hydrophobic and hydrophilic regions of the Heliothis polyhedrin amino acid sequence and the corresponding regions of the gene sequence which encode the hydrophilic and hydrophobic regions (see FIG. 3 and FIG. 1). Since the hydrophilic regions of the amino acid sequence are likely to be external domains of the crystal, and furthermore, are likely to be external domains of the polyhedrin monomer upon crystal dissolution, such regions may be especially useful in an embodiment of the invention employing recombinant OBs in a vaccine formulation, since they would readily provide for presentation of the foreign epitope to the host immune system. Portions of the polyhedrin gene which encode hydrophilic regions are prime candidates for insertion into or replacement by a heterologous gene sequence in this particular embodiment of the invention, since the foreign epitope inserted therein is thus likely to be immunogenic. Thus, the portions of the Heliothis polyhedrin gene sequence which encode regions of the polyhedrin protein which are both hydrophilic and highly variable are good candidates for replacement by heterologous gene sequences, so that the resulting fusion polyhedrin proteins will crystallize and form recombinant OBs containing immunogenic foreign epitopes.

Sequences of the polyhedrin gene which encode hydrophobic regions of the polyhedrin protein may also be inserted into or replaced by heterologous gene sequences, and provide for a recombinant OB that is useful in a vaccine formulation. In a particular embodiment, gene sequences which encode an amphipathic peptide (i.e. a peptide having one face which is hydrophobic, one face which is hydrophilic) (see Section 5.4.1., infra) may be inserted into a region of the polyhedrin gene which encodes a hydrophobic portion of the polyhedrin protein.

In a particular embodiment of the invention, we have identified the amino terminus (roughly amino acids 1 through 4) and amino acid residue numbers 38-50 (see FIG. 3) as hydrophilic regions of the polyhedrin protein which are probably on the surface of the protein and are thus also likely to be on the surface of the OB. The heterologous gene sequence can be inserted into the polyhedrin gene sequence so that the heterologous gene either interrupts or replaces all or a portion of nucleotide residue numbers 1 to 12, and/or 142 to 180, which encode these regions of the amino acid sequence (see FIG. 1). It should be noted that these residue numbers are approximate and that any restriction site or sites which occur within or in proximity to these regions may be used to specifically cleave the polyhedrin gene sequence in order to insert the heterologous gene sequence. Some restriction sites which may be useful include, but are not limited to the restriction sites indicated in FIG. 1. It is preferred to use restriction sites that are unique, so that where no suitable sites exist, new sites may be obtained, for example, by in vitro mutagenesis (Hutchinson, C., et al., 1978, J. Biol. Chem. 253:6551).

5.2. HELIOTHIS VIRUS EXPRESSION VECTORS

At least two types of recombinant expression vectors are involved in the present invention. One embodiment comprises a recombinant Heliothis virus which contains the heterologous gene sequence or gene fragment so that it is under the control of the polyhedrin promoter. Depending upon the location of the heterologous gene within the polyhedrin gene sequence, the heterologous gene product is expressed as either an unfused peptide or protein, a fusion protein or a recombinant occlusion body.

A second embodiment comprises a recombinant Heliothis virus which contains a cloning/restriction site or multiple cloning/restriction sites within the polyhedrin gene sequence; hereinafter this recombinant vector will be referred to as a Heliothis "cassette-expression" virus. The cloning sites are located within the polyhedrin gene sequence so that any heterologous gene of interest or fragment thereof can be inserted into the polyhedrin gene sequence under the control of the polyhedrin promoter. Depending upon the exact location of the cloning sites within the polyhedrin gene sequence, the gene products will be expressed as an unfused peptide or protein, a fusion protein or as a recombinant occlusion body.

Either type of recombinant Heliothis viruses can be constructed from parent Heliothis viruses which possess particularly advantageous properties with respect to the host systems used in accordance with the present invention. For example, Heliothis viruses which demonstrate high infectivity and high virus titers in the host system are preferred. When using Heliothis larvae host systems, Heliothis viruses which do not cause melanization are preferred. Each of these aspects is discussed in more detail infra.

5.2.1. CONSTRUCTION OF RECOMBINANT HELIOTHIS VIRUSES

To construct a recombinant Heliothis virus containing the heterologous gene or a portion thereof, under the control of the polyhedrin promoter as described above, the relevant sequence of the heterologous gene can be inserted into an appropriate location within the polyhedrin gene sequence. Similarly, to construct the recombinant Heliothis virus containing a cloning site or sites, an oligonucleotide sequence which encodes one or more restriction sites that are unique or rare in the polyhedrin gene sequence and/or to the Heliothis genome itself can be inserted in an appropriate location within the polyhedrin gene sequence (hereinafter this oligonucleotide linker will be referred to as a polylinker). The recombinant Heliothis viruses containing either the heterologous sequence or the polylinker can be constructed from parent Heliothis viruses using any technique which provides for recombination of DNA whether in vitro or in vivo. For example, in one embodiment for the construction of recombinant Heliothis viruses of the present invention, in vivo recombination can be utilized to insert the heterologous gene sequence and/or the polylinker into specific sites within the polyhedrin gene. To this end, a transfer vector can be constructed which contains the heterologous gene inserted within the polyhedrin gene sequence and flanked by Heliothis sequences (see, for example, FIG. 5B). Parental Heliothis virus DNA plus transfer vector DNA can be cotransfected into cells susceptible to infection, where in vivo recombination will take place producing the recombinant Heliothis viruses of the invention. Alternatively, a cassette transfer vector can be constructed which comprises a polylinker sequence inserted within the polyhedrin gene sequence and flanked by Heliothis sequences (see, for example, FIG. 5A). Upon transfection of purified viral DNA into susceptible cells with the cassette transfer vector, in vivo recombination will produce a Heliothis cassette-expression virus. The viral DNA can then be isolated for in vitro recombination purposes, in which insertion into or replacement of DNA in the genome of the cassette-expression virus, by a heterologous gene sequence, is facilitated by virtue of the polylinker sequence within the viral genome. Alternatively, in vitro recombination can be accomplished by isolating Heliothis virus DNA which is then cleaved with restriction enzymes specific for appropriate locations within the polyhedrin gene sequence. The heterologous gene or the polylinker is then ligated within the polyhedrin gene at the site of cleavage.

As explained in Section 5.1., different gene products will be expressed depending upon the site of insertion of the heterologous gene sequence and/or the polylinker. However, if a unique restriction site is not present at the desired location, the existing restriction sites can be converted. In order to convert an existing site to a unique restriction site, the polyhedrin sequence can be cleaved with the appropriate restriction enzyme, modified (if necessary) to create blunt ends and ligated in the presence of an appropriate oligonucleotide which encodes the unique restriction site. Additionally, polyhedrin or heterologous gene sequences can be mutated in vitro or in vivo in order to form new restriction endonuclease sites or destroy preexisting ones, to facilitate in vitro ligation procedures. Any technique known in the art can be used, including, but not limited to, in vitro site-directed mutagenesis (Hutchinson, C., et al., 1978, J. Biol. Chem. 253:6551), use of TAB ® linkers (Pharmacia), etc. Portions of the polyhedrin gene sequence can also be replaced, rather than interrupted, by the heterologous sequence. After cleavage of the polyhedrin sequence with an appropriate restriction enzyme or enzymes, the cleaved ends can be "chewed back" using a nuclease such as nuclease BAL-31, exonuclease III, lambda exonuclease, mung bean nuclease, or T4 DNA polymerase exonuclease activity, to name but a few, in order to remove portions of the polyhedrin sequence. Alternatively, cleavage with two or more restriction enzymes to remove the fragment defined by these sites can be accomplished. Subsequent conversion to blunt ends (if necessary) and ligation in the presence of the heterologous gene sequence or the polylinker will result in the elimination of the appropriate regions of the polyhedrin gene and their replacement by the heterologous gene or the polylinker.

The particular strategy for constructing gene fusions will depend on the specific polyhedrin sequence to be replaced, or inserted into, as well as the heterologous gene to be inserted. The discussion infra relates but one strategy by which manipulation of restriction sites of the polyhedrin gene for in vitro recombination purposes may be accomplished, and is intended for descriptive purposes only. Many other recombination strategies are within the scope of the invention.

In one particular embodiment of the invention, a strategy can be employed to insert foreign DNA within the polyhedrin gene at a particular restriction site, which may or may not be a unique restriction site. In this embodiment, single-stranded DNA of the polyhedrin gene of a recombinant vector is manipulated to produce site-specific cleavage at a specific restriction site. (For an example using this strategy, see Section 10.1., infra.) Single-stranded DNA from the polyhedrin gene is isolated. This can be accomplished by many standard techniques such as heat-denaturation of the double-stranded form followed by fractionation, or preferably, by isolating the single-stranded DNA of a vector such as a bacteriophage derivative (e.g., an M13 phage, a phagemid) which contains the polyhedrin DNA inserted within its genome. Specific cleavage at a particular restriction site within the DNA is accomplished by annealing a complementary synthetic oligonucleotide (oligo-1) to the single-stranded DNA, before restriction digestion. This annealing creates the requisite double-stranded region for recognition and cleavage by the restriction endonuclease. After cleavage, the single-stranded linear DNA can then be isolated by known techniques (e.g. heat denaturation and column chromatography). An oligonucleotide with a sequence encoding a foreign epitope can also be synthesized (termed hereinafter oligo 2). Another oligonucleotide can then be synthesized (termed hereinafter oligo 3) which is complementary to oligo 2 and which, in addition, has 5' and 3' termini which extend beyond oligo 2 which are complementary to the single-stranded termini of the polyhedrin DNA. Oligo 2 and oligo 3 can then be annealed together, followed by ligation of the duplex to the single-stranded polyhedrin DNA. Transformation of a suitable vector host such as *E. coli* will produce a recombinant transfer vector which contains the DNA encoding a foreign peptide inserted at a specific restriction site within the polyhedrin gene.

Replacement of nucleotide sequences within the polyhedrin gene may be particularly useful for producing recombinant occlusion bodies in accordance with the invention as described in Section 5.1., supra.

5.2.2. PARENT HELIOTHIS VIRUSES

Any Heliothis virus may be used as the parent for construction of the recombinant Heliothis viruses of the present invention. In a preferred embodiment, a plaque-purified isolate with a homogeneous genotype should be used as the parent Heliothis virus. Moreover, a strain should be selected which has desirable qualities when used in the particular host of the expression vector/host system used in accordance with the present invention.

When working with HzSNPV in larvae host systems, viruses which do not cause melanization are preferred. It is advantageous to time the infection carefully to avoid melanization of either virion containing hemolymph or occlusion bodies. Melanization is a normal response to viral infection which comprises the production of melanin, a pigment which is incorporated into the insect's cuticle, and appears to involve the polymerization of indol ring compounds derived by oxidation of tyrosine (Wigglesworth, V. B., 1974, in The Principles of Insect Physiology, Chapman and Hall, London, p. 610). The tyrosinase which is involved in the melanization process appears to be abundant in the hemolymph of the insect, and can react fairly nonspecifically with available proteins. Thus, the tyrosinase activity in an insect carrying the recombinant viruses of the invention may nonspecifically metabolize the heterologous protein, interfering with and decreasing the yield and purity of the heterologous product. Melanization of occlusion bodies can cause subsequent chemical alteration of virion proteins and nucleic acids. Melanization can also severely reduce infectious extracellular virus titers in collected hemolymph, as well as poison cultured cells following inoculation. Thus, non-melanizing or slow-melanizing host strains are preferred in order to avoid these problems.

Restriction digestion patterns of eight different geographic isolates of HzSNPV suggest each is a separate population of viruses having a slightly different predominant genotype, but none represents a totally unique virus species (Gettig and McCarthy, 1982, Virology 117: 245-252). Seven of the eight geographical isolates examined have similar major occluded virus structural protein profiles in SDS-polyacrylamide gel electrophoresis (SDS-PAGE) (Monroe and McCarthy, 1984, J. Invert. Path. 43: 32-40). Even though the eight Heliothis SNPV isolates are genetically and biochemically similar, several isolates exhibit significant differences in virulence towards H. zea larvae (Gettig and McCarthy, 1982, Virology 117: 245-252).

We have thus far analyzed plaque-purified strains derived from the Elcar TM isolate of HzSNPV (originally isolated by Dr. J. J. Hamm, U.S.D.A., Tifton, GA.). We characterized the genotypic and phenotypic heterogeneity of the Elcar TM isolate by comparing restriction enzyme digestions of viral genomes, SDS-PAGE profiles of occluded virus structural proteins, and differences in larval pathology among the plaque-purified strains.

After purifying and analyzing 20 strains from the Elcar TM isolate we found no single predominant genotype. Each strain could be distinguished using one or more restriction enzymes, and none was identical to the molar restriction pattern of the wild-type isolate. The inability to identify a predominant genotype indicated that this virus is highly variable.

We have identified four regions of variability among the plaque-purified strains based on the HindIII restriction patterns (FIGS. 8, 8A). Alterations in three of these regions (II, III, and IV) are conservative between the plaque-purified strains. A small insertion in HindIII-F of region III in strain HzS-23 is the single exception. Variations in Region I tend to be more significant, with four small deletions and one insertion evident among the genotypes altered in this region. All Region I deletions are located in the BamHI-H fragment. The only strain having an additional alteration outside Regions I-IV is HzS-21 with an insertion in HindIII-D.

Since melanization is a constant problem when studying the biochemistry of HzSNPV, the non-melanizing strains described herein are preferred for use in larval host systems. In particular, strains 5, 7, 8, 9, 15, 21, 22, 24 and 25 described infra (See Section 7, in particular, Table III) cause slow melanization. In the preferred embodiment, strain HzS-15, (also described in Section 7 infra) which causes extremely slow melanization should be used as the parent strain for constructing recombinant Heliothis virus expression vectors for use in larval host systems.

The genotype of the HzS-15 strain (see FIGS. 7, 8 and 8A) differs from the wild-type population genotype in three of the variable regions (II, III, and IV). The divergence between these genotypes is evident in digestions with the enzymes EcoRI, EcoRV, HindIII, and SstI (FIG. 7). The divergence of HzS-15 relative to the wild-type population is caused by changes in the relative position of several restriction sites rather than in overall genome size or organization.

The regions of variability in HzSNPV population genotypes are not restricted to the Elcar TM strain. Reexamination of the published analysis of geographic variation in HzSNPV reveals that these regions of variability exist in other Heliothis species SNPVs (Gettig, R. G. and McCarthy, W. J., 1982, Virology 117:245-252). In addition, many HindIII fragments that are conserved among our plaque-purified isolates are also conserved among the previously analyzed geographic variants. This is especially true of HindIII fragments A, B, D, D', M, and N, all of which appear in 7 out of 8 geographic variants and in 13 out of 20 of our plaque-purified isolates. Whether or not the high degree of variability found in the Heliothis spp. SNPVs (Gettig and McCarthy, 1982, Virology 117: 245-252) confers advantages to the virus population under different geographic conditions remains to be determined.

The restriction enzyme map of HzS-15 (FIG. 8) differs substantially from the previously published map of Knell and Summers (1984, J. Gen. Virol. 65:445-450). For example, the previous map placed BamHI fragments K and I within HindIII fragment B. Our hybridization analysis placed these BamHI fragments in HindIII-C. In addition, PstI fragments D and E hybridized with HindIII-B and J, while the previous map separates these fragments. Our map is constructed based on hybridization results of cloned HzS-15 fragments with genomic digests, and hybridization analyses between the various plaque-purified strains. Errors in the previous map could be attributed to the high heterogeneity of the virus population which probably yielded false positives in their hybridization analysis.

Working with the HzS-15 plaque-purified strain, we obtained a slightly different estimation of the overall genome size. Our estimate of genome size, based upon double digestions and analysis of individual cloned fragments, is approximately 137 kb, rather than the 119 kb previously reported (Knell and Summers, 1984, supra). However, these values are not significantly different and probably reflect expected variations in estimates of DNA fragment size.

The variability between plaque-purified strains is not limited to the genotype, but is also reflected in the structural proteins of the virions (see FIG. 9). We observed differences between strains in several of the occluded virus proteins. In fact, there were more differences between strains of the single Elcar TM isolate than were previously observed between several different geographical isolates of HzSNPV (Monroe and McCarthy, 1984, J. Invert. Path. 43:32-40).

The exact reason for the differences in rate of melanization may be related to the relative ability of individual strains to lyse cells, or in some tissue tropism. Evidence that cell lysis may be responsible for the differences in larval melanization response comes from freeze-thaw experiments with larvae infected with the non-melanizing strain, HzS-15. Unmelanized HzS-15 infected larvae will melanize following several freeze/thaw cycles. Preliminary cell culture data also supports this hypothesis, but further work is required to confirm that cell lysis is the predominant factor.

5.2.3. SELECTION OF RECOMBINANT HELIOTHIS VIRUSES

Selection of recombinant Heliothis viruses of the present invention can be accomplished in a number of ways, depending on how the polyhedrin structural gene was altered as a result of constructing the recombinant virus. For example, the recombinants listed below could be identified and selected on the basis of their inability to produce occlusion bodies (OB−):

(a) Recombinant constructs in which the heterologous gene sequence or the polylinker interrupts the polyhedrin gene sequence so that the polyhedrin gene sequence is no longer in the correct translational reading frame, (i.e., is out-of-phase) or so that the sequences are interrupted by translational stop signals, will not express polyhedrin protein and, thus, will not form occlusion bodies.

(b) Recombinant constructs in which the heterologous gene sequence interrupts the polyhedrin sequence so that each is in the same translational reading frame uninterrupted by translational stop signals, will direct the expression of the heterologous gene product as a fusion protein; however, if the heterologous gene is located in a region of the polyhedrin gene sequence which is essential for crystallization of the polyhedrin gene product, no occlusion bodies will be formed.

Where recombinant Heliothis viruses are OB−, it may be desirable to rescue or restore the ability to form occlusion bodies to the recombinant virus. This may be especially useful if the recombinant virus is to be used in a larva host system where occlusion bodies offer advantages for horizontal transmission of infection. In order to restore the ability to form occlusion bodies, the recombinant virus can be further modified so that a second non-essential region is replaced by the polyhedrin structural gene and its promoter. Such non-essential regions include but are not limited to the p10 gene (Smith et al., 1983, J. Virol. 45:215-225) and the FP locus (Fraser et al., 1985, Virology 145:356-361; Fraser ®t al., 1983, J. Virol. 47:287-300). Such replacement could be effected by recombination in vivo or in vitro as previously explained. Recombination in vivo can be accomplished by using a transfer vector that contains the polyhedrin structural gene and promoter and flanking sequences of the Heliothis viral DNA. Cotransfection of the transfer vector with the OB-recombinant Heliothis virus into susceptible cells will, via in vivo recombination, result in a restoration of the ability of the recombinant virus to express polyhedrin and produce occlusion bodies. Alternatively, restriction enzymes could be used to insert the polyhedrin gene and its promoter in a non-essential region of the recombinant Heliothis virus genome. In these embodiments, the rescued recombinants can be identified as occlusion body positive (OB+) against an OB− background.

A number of approaches are possible with respect to identifying the Heliothis viruses that produce recombinant occlusion bodies:

(a) As previously explained, these recombinant viruses may be constructed via recombination in vivo or in vitro by replacing or interrupting regions of the polyhedrin gene sequence that are non-essential for crystallization, with the heterologous gene sequence so that the sequences are not interrupted by translational stop signals. Since the gene products of these recombinants will be expressed as recombinant occlusion bodies, it may be preferred to use an OB− parent Heliothis virus strain, in order to select OB+ virus plaques against an OB− background. Viruses generating OBs can be detected in plaque assays among the large number of parental viruses which fail to make OBs, since OB+ viruses form more refractile plaques than OB− viruses.

(b) The cloning/expression recombinant viruses may be constructed via recombination in vivo or in vitro by replacing or interrupting regions of the polyhedrin gene sequence that are non-essential for crystallization with a polylinker encoding one or more unique restriction/cloning sites. The resulting recombinant Heliothis virus is akin to a "cassette" into which any heterologous gene can be inserted using appropriate restriction enzymes.

In this embodiment, it is beneficial to insert a polylinker sequence within the polyhedrin gene so that the interrupted polyhedrin sequence is no longer in the correct translational reading frame, in which case the recombinant Heliothis virus containing the cloning sites will be OB−. The subsequent ligation of a heterologous gene into the cloning site located within the region of the polyhedrin gene sequence that is non-essential for crystallization, so that both sequences are in the correct translational reading frame uninterrupted by translational stop signals, will result in a construct that directs the production of a fusion polyhedrin protein that will crystallize and form recombinant occlusion bodies. Viruses which produce the recombinant occlusion bodies can be selected as OB+ plaques against an OB− background.

In selecting for recombinant viruses that produce recombinant occlusion bodies, a control selection experiment which may be done is to cotransfect with wild-type viral DNA (OB+) in order to detect, among the wild-type progeny, recombinants failing to make OBs. Although the identification and characterization of the recombinant generated in this type of cotransfection represents a negative result, it will provide valuable information regarding what modifications of the polyhedrin gene interfere with lattice formation and are therefore unsuitable for the practice of this particular embodiment of the present invention.

Selection of any of the recombinant viruses of the invention can also be done on the basis of physical, immunological, or functional properties of the inserted heterologous gene product. For example, an enzyme-linked immunosorbent assay (ELISA) can be used to detect expression of a foreign antigenic determinant. If a heterologous gene has been incorporated that encodes an enzyme, selection may be done on the basis of enzymatic activity. Staining techniques based on chemical reactivity of the foreign peptide may be used. Many other techniques known in the art can be used, depending on the foreign sequence expressed, and are within the scope of the invention.

While attempting to select recombinant viruses, whether the selection is against an OB− or OB+ background, it is possible to employ other markers which aid in selection. For example, a second gene, encoding a selectable marker, can also be inserted into regions of the polyhedrin gene. Prior to transfer to the virus genome, the selectable marker may exist as a totally distinct DNA fragment or, preferably, may be contained in adjacent DNA sequences of the transfer vector containing the recombinant polyhedrin gene. The selectable marker should be cotransfected with the recombinant polyhedrin gene into the baculovirus where in vivo recombination will occur. Recombinants which also express the selectable marker can then be selected. Many cloned genes known in the art can be used as the selectable marker, including, but not limited to, genes encoding enzymes such as beta-galactosidase, which have standard procedures for selection.

Another method for selection is to screen for presence of the heterologous DNA sequence inserted into the polyhedrin gene. This can be accomplished by techniques known in the art, such as nucleic acid hybridization to replica plaques (Benton, W. D. and Davis, R. W., 1977, Science 196:180), and variations thereof.

Another technique known in the art which may be used for selection is loss of a marker gene activity through inactivation or replacement of the marker gene. In this embodiment, parental baculoviruses can be constructed which contain a selectable marker flanked by sequences homologous to those surrounding the recombinant polyhedrin. For example, a parental baculovirus can be constructed containing a beta-galactosidase gene downstream of the polyhedrin promoter. In vivo recombination between the recombinant polyhedrin gene and the constructed parental strain will result in insertion of the recombinant polyhedrin gene by virtue of its homologies with the parental flanking sequences surrounding the beta-galactosidase gene. The recombination which results in insertion of the recombinant polyhedrin gene and inactivation or replacement of the beta-galactosidase gene may be selected for by the lack of beta-galactosidase activity by known methods (Messing, J., et al., 1977, Proc. Natl. Acad. Sci. U.S.A. 74:3642).

5.3. VECTOR/HOST SYSTEMS FOR USE IN EXPRESSION OF THE HETEROLOGOUS GENE

The recombinant Heliothis viruses described supra can be used to direct the expression of the heterologous gene product in a number of host systems including but not limited to cell lines and larvae in which the Heliothis virus can be propagated. Some useful cell lines and larval systems which can be used in accordance with this embodiment of the invention are described in the subsections below.

0 5.3.1 HELIOTHIS CELL LINES

The in vitro propagation of most SNPVs has been difficult to achieve. The IPLB-HZ1075 cell line, which was originally established by Goodwin (Goodwin, R. H., et al., 1982, In Vitro Cell. Dev. Bio. 18:843–850) from larval ovaries and fat body of the cotton bollworm, *Heliothis zea*, can support the growth of HzSNPV. However, numerous reports have demonstrated that 100% infection is difficult to routinely achieve with this system (Granados, R. R., et al., 1981, Intervirology 16:71–79; Yamada, K., et al., 1982, J. Invert. Path. 39:185–191). It is more common to obtain only 50 to 70% infection as measured by the presence of intranuclear OBs; thus, the usefulness of this system for analysis of HzSNPV replication processes is severely limited. In an effort to increase the productivity of HzSNPV in vitro, some investigators have established new cell lines from *Heliothis zea* (Goodwin et al., supra; McIntosh, A. H., et al., 1985, Intervirology 23:150–156). McIntosh and Ignoffo (1981, J. Invert. Pathol. 37:258–264) have demonstrated replication of HzNPV, with production of OBs, in cell lines derived from *Heliothis zea* or *Heliothis virescens.*

During routine subculturing of the HZ1075 cell line (Goodwin et al., 1982, In Vitro Cell. Dev. Bio. 18: 843–850), we frequently observed clonal outgrowth of cells having similar morphologies. This cell line is heterogeneous, and we considered the possibility that perhaps all cells of the population were not equally susceptible to infection with HzSNPV. We reasoned that isolation and characterization of subclones might,provide a cell strain which would be more susceptible and produce more occlusion bodies upon infection with HzSNPV.

In the specific embodiments of the examples herein, we describe the isolation and characterization of clonal cell strains derived from the IPLB-HZ1075 insect cell line which can be used in the practice of the present invention. These strains exhibited different growth characteristics, morphologies, and viral productivity upon infection with HzSNPV, which are defined herein. We also utilized isozyme markers to characterize the cell strains and demonstrate that they are all derived from *Heliothis zea.*

The IPLB-HZ1075 cell line consists of a heterogeneous population of cells, and this heterogeneity seems to account in part for the inability to obtain 100% infection upon inoculation with HzSNPV. To obtain a more homogeneous response to infection through cloning of individual cell strains, we cloned and characterized twelve strains from IPLB-HZ1075.

All of the cloned cell lines were similar to the parental cell line in that none of them were capable of 100% infection upon inoculation with the HzSNPV isolate HzS-15 under our culture conditions. Each cell strain exhibited slightly different growth kinetics (see FIG. 10), predominant cell morphology, and ability to replicate virus (see Table VII infra).

While predominant cell morphologies were different for most of the cell lines, only two (UND-B and UND-G) exhibited a fairly homogeneous cell morphology. The others were composed of several different morphologies even though they originated from clonal populations. All of the cell strains were fibroblastic, similar to the parental cell line (Goodwin, R. H., et al., 1982, In Vitro 18:843–850).

Population doubling times for the cell strains varied widely between 37.33 and 65.48 hours, and the parental cell line had a doubling time near the maximum (63.15 hours). Routine subculturing of the parental cell line does not appear to select for cells with similar growth kinetics. Perhaps the mixed cell population regulates the growth of individual cell strains in some way, possibly by suppressing the growth of faster growing strains.

There was also wide variability in the percentage of cells infected, and either OB or ECV production. The several parameters we measured to estimate production of OBs in infected cultures could not be linked to either percentage of infected cells or relative cell growth rates. The relative ECV titers from infected cultures were also unrelated to any of the other measured parameters.

Two of the cloned cell strains, UND-H and -K, had statistically higher values than the parent IPLB-HZ1075 cell line for some individual parameters of OB productivity. Strain UND-H produced more OBs per infected cell, while UND-K produced more OBs per culture. These observations are in contrast with earlier studies on the *Trichoplusia ni* cell line TN-368 (Faulkner, P., et al., 1976, in Invertebrate Tissue Culture Applications in Medicine, Biology, and Agriculture, Kurstak, E. and Maramorosch, K., eds., Academic Press, New York, pp. 347–360; Volkman, L. E. and Summers, M. D., 1976, in Invertebrate Tissue Culture Applications in Medicine, Biology, and Agriculture, Kurstak, E. and Maramorosch, K., eds., Academic Press, New York, pp. 289–296). Cloned cell strains of TN-368 were distinguishable from the parental cell line with respect to cell doubling time (Faulkner, P., et al., 1976, supra) and ability to plaque *Autographa californica* MNPV (AcMNPV) (Volkman, L. E. and Summers, M. D., 1976, supra) but none of the TN-368 cloned cell strains replicated AcMNPV better than the uncloned parental cell line.

The values for overall average number of OBs per culture represent an estimate based on two independent variables, OBs per cell and the percentage of infected cells. We feel that the average number of OBs per culture is a better representation of OB productivity. For example, strain UND-K was not significantly different from HZ1075 for both OBs per cell and the percentage of infected cells but was significantly different in average OB per culture. This correlates well with independent observations of UND-K productivity relative to the HZ1075 cell line.

Confirmation that all cell strains were derived from the IPLB-HZ1075 cell line came from comparisons of isozyme staining profiles (see FIG. 11). We also compared isozyme profiles of several invertebrate cell lines (see FIG. 12) and found that all could be separated unambiguously using the enzymes MDH and LDH in tandem. This is in contrast to earlier reports that were unable to separate IPLB-SF21AE and IPLB-HZ1075 using a large number of enzymes and two different gel systems (Brown, S. E. and Knudson, D. L., 1980, In Vitro 16:829–832; Tabachnik, W. J. and Knudson, D. L., 1980, In Vitro 16: 389–392).

In a preferred embodiment, the IPLB-HZ1075 UND-K cell line may be used in the expression vector/host systems of the present invention because of its ability to grow Heliothis virus quickly and at high titers which plaque, thus enabling identification.

In another preferred embodiment, the growth medium of any IPLB-HZ1075 cell line used as a host in accordance with the invention should contain 1% bovine serum albumin and 2 g/liter L-glutamine in order to improve infectivity to about 100%. When using cultured cells as hosts in the expression/host systems of the present invention, it is preferred to infect the cell cultures with ECVs rather than OBs. The infectious cell culture supernatant can be stabilized by the addition of liquid agarose to a final concentration of 0.1%. Alternatively, virions can be isolated from the OBs according to procedures known in the art such as the technique described by Smith and Summers, 1978, Virology 84: 390–402, and the modified procedure described herein in Section 7.1.4. infra.

5.3.2. OTHER CELL LINES

Any cell line in which the recombinant baculovirus of the invention can propagate and express a heterologous gene under the control of the Heliothis promoter can be used. For example, such cell lines include but are not limited to *Heliothis zea* cell lines as described in Section 5.3.1. supra; *Spodoptera frugiperda* IPLB-SF21AE cells; *Estigmene acrea* BTI-EAA cells; *Trichoplusia ni* TN-368 cells; *Trichoplusia ni* BTI-TN4BI, BTI-TN5F2, BTI-TN5F2P, and BTITN5F2A cells (Granados, R. R., et al., 1986, Virology 152:472–476); *Mamestra brassicae* Mb 0503 and Mb 1203 cells (Miltenburger, H. G., et al., 1976, Z. Angew. Entomol. 82(3):306–323); *Heliothis zea* BCIRL-HZ-AM1,2 or 3 cells (McIntosh, A. H. and Ignoffo, C. M., 1981, J. Invert. Pathol. 37:258–264); *Heliothis virescens* BCIRL-HV-AMI cells (id.); and their derivative cell lines.

For an informative discussion of the in vitro replication of baculoviruses, see Volkman, L. E. and Knudson, D. L., 1986, "In Vitro Replication of Baculoviruses, in The Biology of Baculoviruses, Vol. I, Biological Properties and Molecular Biology, Granados, R. R. and B. A. Federici, eds., CRC Press, Florida, which is incorporated by reference herein.

5.3.3. EXPRESSION IN OTHER BACULOVIRUSES

In another embodiment of the invention, heterologous genes expressed under the control of the Heliothis promoter can be contained within any baculovirus genome, including but not limited to NPVs and granulosis viruses (GVs). Studies have shown that polyhedrins of GVs (granulins) and polyhedrins of NPVs form a group of related proteins (Rohrmann, G. F., et al., 1981, J. Mol. Evol. 17:329; Smith, G. E. and Summers, M. D., 1981, J. Virol. 39:125). Thus, the heterologous gene and the Heliothis promoter can be engineered by recombinant DNA techniques (such as described in Section 5.2.1., supra) into granulosis viruses or other NPVs, presumably without adversely affecting essential virus functions. NPVs which may be used in accordance with the present invention include but are not limited to AcMNPV, HzSNPV, *Heliothis virescens* NPV, *S. littoralis* NPV, *Rachoplusia ou* MNPV, *Galleria mellonella* MNPV, *Lymantria dispar* MNPV, *Bombyx mori* SNPV, *Orygia pseudotsugata* SNPV and MNPV, *Orygia leucostigma* NPV, *Choristoneura fumiferana* MNPV, *Pseudohazis eglanterina* SNPV, *N. sertifer* SNPV, *T. paludosa* SNPV, *Trichoplusia ni* MNPV, and *Spodoptera frugiperda* MNPV (Vlak, J. M. and Rohrmann, G. F., supra). GVs which may be used in accordance with the present invention include but are not limited to *P. brassicae* GV, *Estigmene acrea* GV, *Plodia interpunctella* GV, *T. ni* GV, *Choristoneura murinana* GV, *Cirphis unipuncta* GV, *Choristoneura vindis* GV, *Pseudaletia unipuncta* GV, *L. pomonella* GV, *Cydia pomonella* GV, *Mamestra oleracea* GV, *Pygera anastomosis* GV, *S. frugiperda* GV, *Zeiraphera diniana* GV, and *Choristoneura fumiferana* GV (Vlak, J. M. and Rohrmann, G. F., supra; Tweeten, K. A., et al., 1981, Microbiol. Rev. 45:379–408).

In a preferred embodiment, a plaque-purified isolate with a homogeneous genotype should be used as the parent baculovirus. Moreover, a recombinant baculovirus can be constructed from parent viruses which possess particularly advantageous properties with respect to the host systems used in accordance with the present invention, e.g., high infectivity, high titers, and slow melanization.

Appropriate cassette vectors, transfer vectors, and/or cassette-expression vectors can be constructed to facilitate the desired recombinations. The expression of the heterologous gene under control of the Heliothis promoter in other baculoviruses also allows for manipulation of the vector strain in order to achieve maximum efficiency of virus infection and propagation in the particular host used. For example, AcNPV infects *Spodoptera frugiperda* cells more efficiently than does HzNPV; thus, the Heliothis polyhedrin promoter and heterologous gene can be expressed in AcNPV in order to increase the levels of expression obtained in *S. frugiperda* cells.

5.3.4. LARVA HOSTS

Baculoviruses expressing the recombinant polyhedrin genes of the present invention can be propagated and/or mass-produced by infection of various host insect larvae. The propagation and isolation of baculoviruses using laboratory larval populations has been previously described (e.g., Wood, H. A., et al., 1981, J. Invertebr. Pathol. 38:236–241; Ignoffo, C. M. and Garcia, C., 1979, Environ. Entomol. 8 1102–1104). Larva hosts which may be used in the propagation and production of viruses expressing a recombinant polyhedrin gene include but are not limited to those species listed in Table I, infra.

TABLE I.

INSECT LARVA SPECIES WHICH CAN BE USED FOR THE PROPAGATION AND PRODUCTION OF VIRUSES EXPRESSING A RECOMBINANT POLYHEDRIN GENE OF THE PRESENT INVENTION

*Heliothis zea* (Boddie)
*Trichoplusia ni* (Huber)
*Galleria mellonella*
*Spodoptera frugiperda*
*Estigmene acrea*
*Aedes aegypti*
*Choristoneura fumiferana*
*Heliothis virescens*
*Autographa californica*
*S. littoralis*
*Rachoplusia ou*
*Lymantria dispar*
*Bombyx mori*
*Orygia Pseudotsugata*
*Pseudohazis eglanterina*
*N. sertifer*
*T. paludosa*
*P. brassicae*
*Orygia leucostigma*
*Choristoneura vindis*
*Plodia interpunctella*
*Choristoneura murinana*
*Cirphis unipuncta*
*L. pomonella*
*Cydia pomonella*
*Mamestra oleracea*
*Pseudaletia unipuncta*
*Pygera anastomosis*
*Zeiraphera diniana*

In particular embodiments, *T. ni* or *G. mellonella* larvae can be used for the propagation and production of recombinant AcMNPV, *G. mellonella* MNPV, or *T. ni* MNPV, while *H. zea* can be used to support the growth of recombinant HzSNPV.

Any rearing conditions and diet formulations can be used which support the growth and maintenance of the larvae. One example of a diet mix which can be used to support the growth of *T. ni* or *H. zea* larvae is described in Section 9.1. infra. Examples of rearing conditions which can be used for *H. zea*, *T. ni*, or *G. melonella* are described infra in Sections 9.2.1., 9.2.2., and 9.3. It is possible that the larvae are cannibalistic (e.g., *Heliothis zea*) and, therefore, cannot be grown all together. It would therefore be preferable to separate the larvae so that only one or two insects are dispensed into each container for growth.

It is preferable, but not required, to maintain the larval cultures in a germ-free environment. The cultures thus maintained would be free from the presence of exogenous microorganisms which can potentially produce substances toxic or allergenic for humans.

In a further preferred method of the invention, insect larvae can be cultured free of both exogenous and endogenous microorganisms. Since Lepidopterans (e.g., *Heliothis zea*, *Trichoplusia ni*, etc.) contain no endogenous symbiotic microorganisms, they can be maintained in the absence of both endogenous and exogenous microorganisms, thus eliminating the danger of contamination by microorganisms pathogenic for humans. In accomplishing and maintaining these germ-free conditions, the insect eggs can be sterilized (e.g. by treatment with peracetic acid; see Section 9.3., infra). The insect diet mix can be sterilized, e.g. by the use of radiation.

In addition, as discussed in Section 5.2.2. supra, a non-melanizing strain of virus is preferred for use, in order to optimize yield and purity of the heterologous protein obtained from the infected larvae.

In another embodiment of this aspect of the invention, it is possible to produce and use giant larvae for the propagation of the recombinant baculoviruses of the invention. Selective inhibition of juvenile hormone (JH) esterase has been shown to result in the maintenance of JH titers and in the production of giant larvae (Sparks, T. C., et al., 1983, Insect Biochem. 13:529; Hammock, B. D. and Roe, R. M., 1985, Meth. Enzymol. 111B:487). The use of such larvae in the mass production of the heterologous proteins of the invention can greatly increase the obtained yields.

5.3.5. EXPRESSION IN OTHER MICROORGANISMS

The recombinant polyhedrin genes of the present invention can also be expressed in vector/host systems involving other microorganisms including but not limited to other viruses such as vaccinia viruses, adenoviruses, retroviruses, etc.; yeast; and bacteria. The appropriate cassette vectors, transfer vectors, and/or cassette-expression vectors can be used to facilitate the appropriate recombinations. For example, a bacterial plasmid cassette vector can be constructed to contain the Heliothis promoter and a polylinker region, which upon insertion of a heterologous gene at a restriction site in the polylinker and transformation of the appropriate bacterial strain, will provide for the expression of the heterologous gene under the control of the Heliothis promoter.

As one embodiment, the expression of recombinant polyhedrin genes in bacterial cells has a number of attractive advantages. It would eliminate the need to transfer gene fusions into a baculovirus and to identify and characterize the resulting recombinant virus. In addition, it is less expensive and easier to grow large quantities of bacterial cells than to culture insect cells. Many different strains of bacteria and types of plasmids known in the art can be used in this embodiment of the present invention, as long as the host allows for appropriate expression of the recombinant polyhedrin gene of the vector.

Production in bacterial expression systems can be accomplished by use of the same type of genetic manipulations as described in Section 5.2.1., supra. As an example, in a particular embodiment where recombinant OB formation is desired, by taking advantage of the degeneracy of the genetic code, a polyhedrin gene segment can be synthesized which contains new and unique restriction sites, yet encodes the same amino acids as the wild-type polyhedrin gene. Thus, a "polyhedrin polylinker" sequence is created, which can be ligated to the remainder of the parental polyhedrin gene, and which can be utilized to insert sequences encoding foreign epitopes at its unique restriction sites. Such a gene construction provides the potential to easily engineer a large number of changes into the polyhedrin gene. In addition, the gene construction can be designed with flanking restriction sites suitable for insertion into *E. coli* expression vectors. Such a construction is not restricted to use in *E. coli*; it can also be engineered for use in the baculovirus or other systems.

One example of such an Autographa polyhedrin polylinker is shown in FIG. 4. FIG. 4 depicts a gene segment encoding the amino terminus to amino acid 58 (at the BamHI site) of the *Autographa californica* polyhedrin protein, which also contains new PvuI, ScaI, BclI, and XbaI sites at positions corresponding to amino acids 9, 19, 27, and 46, respectively. Ligation of a two kilobase pair BamHI fragment containing the 3' end of the AcMNPV polyhedrin gene will reconstruct the entire gene. The unique restriction sites can facilitate the replacement of small regions in the 5' section of the gene with synthetic oligonucleotides encoding new antigenic determinants. A Heliothis polyhedrin polylinker for use in the present invention can be constructed in a similar manner. The unique EcoRI site immediately 5' to the synthetic gene permits cloning the fusion gene into an EcoRI site of an *E. coli* expression vector. For example, a vector which may be used is the *E. coli* expression vector PK223-3 (Pharmacia). This plasmid contains the tac promoter (de Boer, H. A., et al., 1983, Proc. Natl. Acad. Sci. U.S.A. 78:21) and Shine-Delgarno sequences upstream of unique cloning sites. In addition, there are strong ribosomal termination sequences downstream of the cloning sites. Thus, the PK223-3 plasmid construction would permit efficient regulated expression of genes inserted at its cloning site. Numerous other plasmids with suitable cloning sites and signals for expression may also be used.

In a particular embodiment of the invention, where a recombinant fusion polyhedrin protein is produced that is capable of forming occlusion bodies, construction and expression in a suitable vector/host system will determine whether the recombinant polyhedrin expressed in such a system will crystallize. If the protein will not crystallize in vivo, the solubilized polyhedrin protein can be purified and crystallized in vitro (Shigematsu, H. and Suzuki, S., 1971, J. Invert. Pathol. 17:375–382). Thus, by expressing the recombinant polyhedrin genes, polyhedrin crystals exposing new epitopes can be generated. As an example, using the polylinker sequence of FIG. 4, and replacing the segment between the XbaI site and either the BamHI or BclI site, enables the insertion of new determinants in a putatively modifiable region between amino acids 37–49. The SphI site can be used to add determinants to the amino terminus of the protein. The Heliothis polyhedrin gene can be manipulated in a similar fashion, to provide for the expression in bacteria of a recombinant polyhedrin protein in accordance with the present invention which can crystallize and form occlusion bodies.

The preceding discussion is intended only as an example of the types of manipulations and constructions which may be employed in the cloning and expression of recombinant polyhedrins. Other vectors, hosts, and synthetic gene sequences may be manipulated in similar fashions to express the recombinant polyhedrins of the present invention.

5.4. ISOLATION OF HETEROLOGOUS GENE PRODUCT

Isolation of the heterologous gene product expressed under control of the Heliothis promoter can be by any techniques known in the art for the purification of proteins, including but not limited to chromatography (e.g., high-pressure liquid chromatography, immunoaffinity, ion-exchange, and sizing column chromatography), centrifugation, differential solubility, isoelectric focusing, and two-dimensional gel electrophoresis.

5.4.1. UNFUSED PROTEIN PRODUCTS

Unfused heterologous proteins that are secreted can be isolated from cell culture media by standard techniques. If the heterologous protein is internal or plasma membrane-associated, host cells can be broken open by various techniques known in the art including but not limited to detergent lysis, Dounce homogenization, sonication, osmotic shock, use of a French press, etc., after which the desired subcellular fraction can be isolated (by standard techniques, e.g. centrifugation as in Feldman et al., 1983, J. Virol. 45:782-791). If a monoclonal antibody to the heterologous protein is available, immunoaffinity chromatography may be used as an effective means of purification (Goding, J. W., 1983, Monoclonal Antibodies: Principles and Practice, Ch. 6, "Affinity Chromatography Using Monoclonal Antibodies", Academic Press, Inc., London, pp. 188–207).

5.4.2. FUSION PROTEIN PRODUCTS

Recombinant polyhedrins of the present invention that are fusion proteins may be purified by any of the techniques discussed supra. However, depending on the individual molecules, fusion products may require different methods of purification to account for any unique properties such as altered solubility or cellular localization. For instance, expression of a recombinant fusion polyhedrin under control of the Heliothis promoter in bacteria may lead to the formation of cytoplasmic inclusion bodies containing the recombinant protein (Williams, D. C., et al., 1982, Science 215:687). Recovery of the protein from such refractile bodies can be accomplished by procedures known in the art (Builder et al., U.S. Pat. No. 4,511,502; Olson et al., U.S. Pat. No. 4,511,503; Jones et al., U.S. Pat. No. 4,512,922; Olson et al., U.S. Pat. No. 4,518,526; Builder et al., U.S. Pat. No. 4,620,948). The recombinant protein that is overproduced in bacteria may also form aggregates which renders it surprisingly stable and facilitates purification (Cheng, Y.-S., et al., 1981, Gene 14:121–130). In addition, bacteria overproducing recombinant protein can be separated on the basis of increased density relative to that of normal bacteria (Cheng, U.S. Pat. No. 4,480,038). In a specific embodiment, a monoclonal antibody recognizing the recombinant polyhedrin protein (directed against either a polyhedrin or heterologous epitope) can be used in immunoaffinity chromatography as an effective means of purification (Goding, J. W., 1983, Monoclonal Antibodies: Principles and Practice, Ch. 6, "Affinity Chromatography Using Monoclonal Antibodies", Academic Press, Inc., London, pp. 188–207).

5.4.3 RECOMBINANT OCCLUSION BODIES

OBs can be purified from a number of host cells by known techniques (for example, see Section 7.1.4. infra, and Tweeten, K. A., et al., 1981, Microbiol. Rev. 45:379–408). These techniques may be used to purify recombinant OBs in accordance with the invention. Host cells include, but are not limited to, cell lines and larvae in which the baculovirus can be propagated and produce OBs. For example, such cell lines include, but are not limited to, *Spodoptera frugiperda* IPLB-SF-21AE cells, *Heliothis zea* IPLB-HZ1075 cells, *Aedes aegypti* ACT-10 cells, *Estigmene acrea* BTI-EAA cells, *Trichoplusia ni* TN-368 cells, and their derivative cell lines. Infection of tissue culture cells can be accomplished by standard procedures known in the art (Smith, G., and Summers, M., 1979, J. Virol. 30:828). In a particular embodiment, *Spodoptera frugiperda* cells can be infected with *Autographa californica* MNPV at 1-2 pfu/cell. Polyhedrin protein can then be purified from OBs by techniques known in the art. For example, polyhedrin protein can be purified by incubating the purified occlusion bodies in 0.1 M $Na_2CO_3$ (pH 11), 0.17 M NaCl, 1 mM EDTA, and spinning the dissolved protein at 24,000 rpm in an SW50.1 rotor for 30 minutes at 4° C. to remove virus particles and any insoluble material. The solubilized polyhedrin can be stored at −20° C. (Huang, Y. S., et al., 1985, Virology 143:380), and the homogeneity of the preparation can be determined by SDS polyacrylamide gel electrophoresis, among other methods.

As an additional or alternative method, a monoclonal antibody directed against a recombinant polyhedrin protein can be used as an effective means of purifying the polyhedrin protein. For example, isolated preparations of recombinant OBs can be solubilized, the recombinant polyhedrin protein purified by immunoaffinity chromatography (Goding, J. W., 1983, supra) and then recrystallized to form a purified preparation of recombinant OBs. This method requires an antigen that remains capable of binding to antibody even after the stringent conditions necessary for crystal dissolution.

5 5.5. VACCINES

5.5.1. DEMONSTRATION OF IMMUNOPOTENCY OF FOREIGN EPITOPES EXPRESSED BY RECOMBINANT POLYHEDRIN GENES

Demonstration of immunopotency of the epitope of a pathogenic microorganism, expressed by a recombinant polyhedrin gene in accordance with the present invention, is a necessary step prior to vaccine formulation. Immunopotency of the foreign epitope can be determined by monitoring the immune response of test animals following immunization with the recombinant polyhedrin gene product.

Unfused heterologous proteins and recombinant polyhedrins which do not form occlusion bodies may be purified by standard techniques known in the art (see Sections 5.4., 5.4.1., and 5.4.2., supra) and formulated with an appropriate adjuvant to enhance the immunological response. Suitable adjuvants include, but are not limited to, mineral gels, e.g., aluminum hydroxide, surface active substances such as lysolecithin, pluronic polyols, polyanions, peptides, oil emulsions, and potentially useful human adjuvants such as BCG (bacille Calmette-Guerin) and corynebacterium parvum.

Recombinant occlusion bodies for immunization purposes can be obtained by purification from insects or insect cell cultures (for example, by the procedures of Section 7.1.4. infra, and Tweeten, K. A., et al., 1981, Microbiol Rev. 45:379-408), or by in vitro recrystallization of polyhedrin (Shigematsu, H. and Suzuki, S., 1971, J. Invert. Pathol. 17:375-382).

Test animals may include but are not limited to mice, rabbits, chimpanzees, and eventually human subjects. Methods of introduction of the immunogen may include oral, intradermal, intramuscular, intraperitoneal, intravenous, subcutaneous, intranasal, or any other standard route of immunization. The immune response of the test subjects can be analyzed by at least three approaches: (a) the reactivity of the resultant immune serum to the authentic pathogenic molecule or a fragment thereof containing the desired epitope, or to the isolated naturally occurring pathogenic microorganism, as assayed by known techniques, e.g. enzyme linked immunosorbant assay (ELISA), immunoblots, radioimmunoprecipitations, etc., (b) the ability of the immune serum to neutralize infectivity of the pathogen in vitro, and (c) protection from infection and/or attenuation of infectious symptoms in immunized animals.

5.5.2. RECOMBINANT POLYHEDRIN GENE PRODUCTS IN VACCINE FORMULATIONS

Any protein epitope of a pathogenic microorganism which is capable of inducing an immune response specific to the microorganism can potentially be used in a vaccine formulation. Demonstration of the production of recombinant polyhedrin gene products which express the foreign epitope in an immunopotent state, as provided for by the present invention, is necessary prior to formulation as a vaccine.

Potentially useful antigens for vaccine formulations can be identified by various criteria, such as the antigen's involvement in neutralization of the pathogen's infectivity (Norrby, E., 1985, Summary, In Vaccines85, Lerner, R. A., R. M. Chanock, and F. Brown (eds.), Cold Spring Harbor Laboratory, New York, pp. 388-389), type or group specificity, recognition by patients' antisera, and/or the demonstration of protective effects of antisera generated to the antigen. In addition, the antigen's encoded epitope should preferably display a small or no degree of antigenic variation in time. The gene sequence encoding the epitope to be expressed by a recombinant polyhedrin gene may be obtained by techniques known in the art including but not limited to purification from genomic DNA of the microorganism, by cDNA synthesis from RNA of the microorganism, by recombinant DNA techniques, or by chemical synthesis.

Recombinant polyhedrin gene products have potential uses in vaccines for diseases and disorders of viral, parasitic, and bacterial origins. Many viral-specific antigens are known and can potentially be incorporated into the vaccine formulations of the invention. For example, such antigens, and/or portions thereof which encode the epitope(s), which may be used include but are not limited to influenza A hemagglutinin; Hepatitis A virus VP1; Hepatitis B surface, core, or e antigens; retroviral envelope glycoproteins or capsid proteins; poliovirus capsid protein VP1; rabies virus glycoprotein; foot and mouth disease virus VP1; Herpes simplex virus glycoprotein D; Epstein-Barr virus glycoprotein; pseudorabies virus glycoprotein; vesicular stomatitis virus glycoprotein, etc. In a particular embodiment, the recombinant polyhedrin gene products of the invention can comprise an epitope of the AIDS virus (HTLV III/LAV/HIV) glycoprotein and/or capsid proteins. Such an embodiment may be particularly useful in vaccinating against AIDS without concomitant induction of detrimental effects caused by the presence of the active AIDS virus glycoprotein, such as the induction of T lymphocyte cell fusion and death.

Recent research has identified many potential antigens of bacteria or parasites which may be formulated in vaccines in accordance with the present invention. For example, such antigens, or fragments thereof which encode the epitope(s), which may be formulated in vaccines in accordance with the present invention include but are not limited to malaria antigens (Miller, L. H., 1985, In Vaccines85, Lerner, R. A., R. M. Chanock, and F. Brown (eds.), Cold Spring Harbor Laboratory, New York, pp. 1-5), cholera toxin, diptheria toxin, and gonococci antigens. As more specific examples, microbial genes which have been successfully cloned and may be used in recombinant polyhedrin gene product vaccine formulations include but are not limited to, enterotoxin genes of *E. coli*, the toxin and filamentous hemagglutinin genes of *Bordetella pertussis*, and the circumsporozoite (CS) antigen of the malaria parasite *Plasmodium falciparum* (Norrby, E., 1985, In Vaccines85, supra, pp. 387-394; Dame, J. B., et al., 1985, In Vaccines85, supra, pp. 7-11).

The heterologous protein expressed under control of the Heliothis polyhedrin promoter, may be used as an immunogen in subunit vaccine formulations, which may be multivalent. The recombinant polyhedrin gene product may be purified for purposes of vaccine formulation from any vector/host systems that express the heterologous protein. Such systems include any of the previously described virusinfected cultured cells or in vivo hosts, bacterial transformants, yeast transformants, etc. (see Sections 5.3. and 5.4., supra). The purified protein should be adjusted to an appropriate concentration, formulated with any suitable vaccine adjuvant and packaged for use. Suitable adjuvants include, but are not limited to: mineral gels, e.g., aluminum hydroxide; surface active substances such as lysolecithin, pluronic polyols; polyanions; peptides; oil emulsions; and potentially useful human adjuvants such as BCG (bacille Calmette-Guerin) and corynebacterium parvum. The immunogen may also be incorporated into liposomes, or conjugated to polysaccharides and/or other polymers for use in a vaccine formulation.

In instances where the recombinant polyhedrin gene product is a hapten, i.e. a molecule that is antigenic in that it can react selectively with cognate antibodies, but not immunogenic in that it cannot elicit an immune response, the hapten may be covalently bound to a carrier or immunogenic molecule; for instance, a large protein such as protein serum albumin will confer immunogenicity to the hapten coupled to it. The hapten-carrier may be formulated for use as a vaccine.

Many methods may be used to introduce the vaccine formulations described above; these include, but are not limited to, oral, intradermal, intramuscular, intraperitoneal, intravenous, subcutaneous and intranasal routes.

5.5.2.1. RECOMBINANT OCCLUSION BODIES IN VACCINE FORMULATIONS

Recombinant OBs expressing epitopes of pathogenic microorganisms are particularly useful in the formulation of vaccines. In a preferred embodiment, the foreign epitope is exposed on the surface of the crystal. Since the crystalline lattice of the occlusion body is composed predominantly of the polyhedrin molecule, foreign epitopes within this molecule are presented a large number of times on the surface of the OB. Recombinant OBs can be used in vaccine formulations even if the foreign epitope is not presented on the surface of the crystal but is internal, since alterations in crystallization properties (e.g. dissociation in vivo) can allow slow release of protein (comprising the foreign epitope) from the crystal, allowing presentation of the epitope to the host's immune system. In addition, the occlusion bodies are produced in large quantity, are stable structures, and are easy to purify. They can be generated in insect cell cultures that do not produce known human pathogens. In a particular embodiment, recombinant OBs for vaccine use can be obtained from infected insect larvae grown in a germ-free environment.

The use of recombinant OBs may be especially advantageous when the heterologous peptide or protein to be used in a vaccine formulation is a hapten (i.e., a molecule that is antigenic but not immunogenic) which ordinarily must be coupled to a carrier molecule that confers immunogenicity. The production of recombinant OBs carrying the heterologous hapten on their surface using the expression vector/host systems of the present invention would render the molecule immunogenic and eliminate coupling reactions. Furthermore, the recombinant OBs can be dissociated and recrystallized (e.g., by the procedure of Shigematsu, H., and Suzuki, S., 1971, J. Invert. Pathol. 17:375) so that (a) contaminating virions and carbohydrate are removed; and/or (b) a mixture of recombinant OBs, each of which bears a different heterologous protein, can be solubilized and recrystallized. The resulting OBs would bear each of the heterologous proteins and would be particularly useful as a multivalent vaccine.

In another specific embodiment of this aspect of the invention, the foreign peptide or protein to be expressed on or within a recombinant OB may be amphipathic, that is, having one face hydrophilic and one face hydrophobic. Such a foreign peptide may be especially useful in the induction of T cell-mediated immunity. An amphipathic epitope may provoke T cell stimulation by providing for the interaction of its hydrophobic face with the presenting cell membrane or Ia, and the interaction of its hydrophilic face with the T cell receptor (Allen, P. M., et al., 1984, Proc. Natl. Acad. Sci. U.S.A. 81:2489; Berzofsky, J. A., et al., 1985, in Immune Recognition of Protein Antigens, Laver, W. G. and G. M. Air, eds., Current Communications in Molecular Biology, Cold Spring Harbor Laboratory, New York, pp. 156-160). In a particular embodiment, a heterologous sequence encoding an amphipathic alpha-helical structure can be inserted into or replace portions of the polyhedrin gene which are variable and which encode alpha-helical regions (which may be hydrophobic), so that a recombinant protein is produced which allows both the OB and the amphipathic epitope within it to retain their structural integrity. An example of a polyhedrin gene sequence which is both variable and encodes an alpha-helical region is that encoding amino acids 37-49 of the Heliothis polyhedrin protein.

5.5.3. USES OF ANTIBODIES GENERATED BY IMMUNIZATION WITH RECOMBINANT POLYHEDRINS

The antibodies generated against pathogenic microorganisms by immunization with the recombinant polyhedrin gene products of the present invention also have potential uses in diagnostic immunoassays, passive immunotherapy, and generation of antiidiotypic antibodies.

The generated antibodies may be isolated by standard techniques known in the art (e.g. immunoaffinity chromatography, centrifugation, precipitation, etc.) and used in diagnostic immunoassays to detect the presence of viruses, bacteria, or parasites of medical or veterinary importance in human or animal tissues, blood, serum, etc. The antibodies may also be used to monitor treatment and/or disease progression. Any immunoassay system known in the art may be used for this purpose including but not limited to competitive and noncompetitive assay systems using techniques such as radioimmunoassays, ELISA (enzyme linked immunosorbent assays), "sandwich" immunoassays, precipitin reactions, gel diffusion precipitin reactions, immunodiffusion assays, agglutination assays, complement-fixation assays, immunoradiometric assays, fluorescent immunoassays, protein A immunoassays and immunoelectrophoresis assays, to name but a few.

The vaccine formulations of the present invention can also be used to produce antibodies for use in passive immunotherapy, in which short-term protection of a host is achieved by the administration of pre-formed antibody directed against a pathogenic microorganism. Passive immunization could be used on an emergency basis for immediate protection of unimmunized individuals who have been exposed to a pathogenic microorganism, for instance, in hospitals and other health-care facilities. Human immunoglobulin is preferred for use in humans since a heterologous immunoglobulin will induce an immune response directed against its foreign immunogenic components.

The antibodies generated by the vaccine formulations of the present invention can also be used in the production of antiidiotypic antibody. The antiidiotypic antibody can then in turn be used for immunization, in order to produce a subpopulation of antibodies that bind the initial antigen of the pathogenic microorganism (Jerne, N. K., 1974, Ann. Immunol. (Paris) 125c:373; Jerne, N. K., et al., 1982, EMBO 1:234).

5.6. BIOLOGICAL INSECTICIDES

Baculoviruses are major pathogens of a large number of agricultural pests (Vlak, J. M. and Rohrmann, G. F., supra). The corn earworm *Heliothis zea* in many areas routinely damages 90–100% of the ears of sweet corn (Kirk-Othmer, Encyclopedia of Chemical Technology, 1981, 3rd Ed., Vol. 13, John Wiley & Sons, New York, pp. 415). HzSNPV has been approved as a viral insecticide and is used as a pathogen for the cotton bollworm and the corn earworm. The occlusion body (OB) is the infectious particle responsible for transmission of the virus from organism to organism in the wild. In a particular embodiment of the present invention, the production of recombinant occlusion bodies provides for horizontal transmission of infection with concomitant expression of a foreign gene. Manipulation of the polyhedrin protein to incorporate enzymatic activities, toxic peptides, or any molecule with insecticidal activity can increase the lethality of the OB to host agricultural pests. Thus, the recombinant OBs of the present invention have valuable applications as biological insecticides.

In a particular embodiment of this aspect of the invention, the recombinant Heliothis polyhedrin protein is capable of forming a recombinant occlusion body which comprises a foreign peptide with insecticidal activity. In an alternative embodiment, the incorporation of the foreign insecticidal sequence into the Heliothis polyhedrin gene may initially destroy occlusion body formation, but the ability to form occlusion bodies can be restored by the insertion of another, nondefective, polyhedrin gene into a nonessential region of the viral genome. Thus, *Heliothis zea* NPVs which form occlusion bodies can express a foreign insecticidal sequence within a recombinant polyhedrin molecule that may or may not form part of the crystalline polyhedra.

Genes which may be recombined into polyhedrin genes in accordance with this embodiment of the invention include any genes which encode molecules that effectively increase the desired insecticidal activity of the baculovirus without impairing the viability or infectivity of the virus itself. Such molecules include but are not limited to those which encode enzymes, enzyme inhibitors, insect hormone antagonists, neurotoxins, metabolic inhibitors, insect chemattractants, endotoxins of other insect pathogens, etc. For example, molecules which interfere with physiological and/or developmental processes unique to arthropods that are susceptible to baculoviral infection, may be expressed in recombinant polyhedrins. Such molecules include but are not limited to insect growth regulators such as hormone antagonists (e.g. neotenin antagonists), and chitin synthesis inhibitors. Neuropeptides which are toxic or which induce detrimental behavioral modifications (e.g. loss of appetite or mating behavior) may be encoded within the polyhedrin gene. Sec pheromones which act as chemattractants may be used to increase spread of the baculovirus infection throughout the insect population. A chitinase incorporated into the OB may increase the infectivity of the virus. An endotoxin of another insect pathogen, such as the *Bacillus thuringiensis* endotoxin, may be expressed in order to increase pathogenicity. Many specific embodiments of the invention are possible, provided that the recombinant form of the insecticidal molecule is functionally active within the physiological environment of the infected insect. Metabolic precursors to insecticidal molecules may also be encoded by the recombinant polyhedrin gene, provided that the metabolic machinery to convert the peptide to a biologically active form is available and functional at the site of infection within the host insect.

Any standard method can be used to assay lethality of the recombinant baculovirus. Such methods include but are not limited to the diet-surface technique and container, to bioassay OB activity (Ignoffo, C. M., 1966. J. Invert. Pathol. 8:531–536; Ignoffo, C. M. and Boening, O. P., 1970, J. Econ. Entomol. 63:1966–1967).

5.7 EXPRESSION VECTORS

The vector/host systems which express the recombinant polyhedrin genes of the present invention can be used generally as expression vector systems for the production of foreign peptide(s). In this embodiment of the invention, the recombinant vectors which express a foreign peptide under control of the Heliothis polyhedrin promoter are propagated in an appropriate host cell in order to obtain the desired quantities of the heterologous peptide To this end, the foreign peptide may be purified from the host cell or subcellular fractions, cell culture media, occluded virions, isolated occlusion bodies, infected larvae, etc., by standard techniques known in the art for the purification of proteins, including but not limited to chromatography (e.g. ion exchange, affinity, and sizing column chromatography), centrifugation, differential solubility, isoelectric focusing, and preparative electrophoresis. (See also Section 5.5., supra.) In a specific embodiment, expression of the recombinant polyhedrin gene as a crystallizable protein (i.e., capable of forming a recombinant OB) can greatly facilitate isolation of the heterologous protein in substantially pure form.

5.8. IMMUNOASSAYS

The recombinant polyhedrin gene products of the present invention, or fragments thereof, expressing foreign epitope(s), may be used as antigens in immunoassays for the detection of antibodies to the epitope(s).

The heterologous protein, or fragments thereof, may also be used to detect the same or related epitope(s) by competition assays. The recombinant polyhedrin products, or the foreign epitope(s) expressed by them, may be used in any immunoassay system known in the art including but not limited to competitive and noncompetitive assay systems using techniques such as radioimmunoassays, ELISA (enzyme-linked immunosorbent assay), "sandwich" immunoassays, precipitin reactions, gel diffusion precipitin reactions, immunodiffusion assays, agglutination assays, complement-fixation assays, immunoradiometric assays, fluorescent immunoassays, protein A immunoassays and immunoelectrophoresis assays, to name but a few.

6. EXAMPLE

CONSTRUCTION OF TRANSFER VECTORS USED FOR INTRODUCING FOREIGN GENE SEQUENCES INTO THE HELIOTHIS POLYHEDRIN GENE TO PRODUCE Hz RECOMBINANTS

The subsections below describe the sequencing of the Heliothis polyhedrin gene and the construction of a family of plasmid transfer vectors which allow for the production of *Heliothis zea* virus recombinants which contain foreign genes within the polyhedrin gene sequence.

6.1. MATERIALS AND METHODS

6.1.1. RESTRICTION MAPPING

Plasmid DNAs were digested with restriction endonucleases HindIII, EcoRI, PstI, XbaI, BamHI, SalII XhoI, NruI, ClaI, HincII, BclI, or KpnI under conditions specified by the manufacturer (Bethesda Research Laboratories or Promega Biotec). Digested DNAs were size fractionated on 0.7% to 1.2% agarose or 8% acrylamide gels containing 90 mM Tris-borate, 90 mM boric acid, 2 mM EDTA (pH 8.0), and 0.1 ug/ml of ethidium bromide. DNA bands were visualized with an ultraviolet transilluminator and photographed. Analyses of single and multiple digestions were used to construct the restriction maps.

6.1.2. SOUTHERN BLOTTING

Gels were soaked in denaturing solution (0.5 M NaOH, 1.5 M NaCl) for 30 minutes. The gels were neutralized by soaking in 1.0 M Tris-HCl pH 8.0, 1.5 M NaCl. DNA was transferred to nitrocellulose by a modification of the method of Southern (J. Mol. Biol. 98:503–517). DNA was blotted using 1.0 M $NH_4$ acetate. Filters were baked under vacuum for two hours and soaked in prehybridization solution (0.12 M $NaPO_4$ pH 6.8, 2 X SSC, 50% formamide, 10 mM EDTA, 1% sarcosyl and 3X Denhardts) for more than three hours. Filters were rinsed with distilled water and incubated at 37° C. overnight with fresh prehybridization solution plus denatured labelled radioactive probes. Filters were rinsed in 0.2 X SSC and washed for one hour in prehybridization solution without Denhardts. Rinses and washes were repeated four times. Filters were dried and autoradiographed with Kodak X-Omat AR5 film.
SSC = 150 mM NaCl, 15 mM sodium citrate pH 7.0
Denhardt's Solution = 0.02% ficoll, 0.02% polyvinylpyrrolidone, 0.02% BSA

6.1.3. DNA SEQUENCING

DNA sequences were determined using the dideoxy chain termination method with M13 subclones (Sanger, F., Nicklen, S., and Coulson, A. R., 1977, Proc. Natl. Acad. Sci. U.S.A. 74:5463–5467; Messing, J., Crea, R., and Seeburg, P. H., 1981, Nucl. Acid Res. 9:309–321) of the Heliothis polyhedrin gene. Supernatants of M13 infected cells were centrifuged two times at 5000 rpm for 20 minutes to remove cells and cell debris. Phage were precipitated by adding 1/5 volume 20% PEG6000, 2.5 M NaCl. Pellets were resuspended in 6, 6, .2 (6 mM Tris-HCl pH 8.0, 6 mM NaCl 0.2 mM EDTA) and virus reprecipitated with 1/5 volume 20% PEG, 2.5 M NaCl. Care was taken to remove as much liquid from the pellet as possible. Pellets were resuspended in 6, 6, .2 and DNA was extracted with phenol saturated with 0.1 M Tris pH 8.0. DNA was reextracted with phenol:chloroform (1:1), then with chloroform, and finally with ether. DNA was precipitated with ethanol twice and rinsed one time.

Single stranded DNA templates were annealed to sequencing primers (Bethesda Research Laboratories or Pharmacia) in 10 ul reactions containing 5 ul of single stranded template, 2 ul of primer, 2 ul of HB buffer (70 mM Tris pH 7.5, 70 mM $MgCl_2$, 500 mM NaCl). Reactions were heated to 95° C. for 5 minutes and allowed to cool to room temperature for 45 minutes. After annealing, 2 ul of alpha 32P-dATP, 1 ul of 25 uM dATP and 2 Units of DNA Polymerase Large Fragment (Bethesda Research Laboratories, Pharmacia, or Promega Biotec) were added. Primer extensions in the presence of the dideoxy nucleotides were initiated by adding 3 ul of the annealing mix to tubes containing the appropriate mix of dideoxy (dd) and deoxy nucleotides. A reaction: 1 ul of 0.5 mM ddATP and 1 ul 125 uM dCTP, dGTP and dTTP. G reaction: 1 ul of 0.625 mM ddGTP and 1 ul 8 uM dGTP, 170 uM dCTP and 170 uM dTTP. C reaction: 1 ul 0.5 mM ddCTP and 1 ul 8 uM dCTP, 170 uM dGTP and 170 uM dTTP. T reaction: 1 ul 0.84 mM ddTTP and 1 ul of 8 uM dTTP, 170 uM dCTP and 170 uM dGTP. Reactions were incubated at 45.C for 15 minutes. 1 ul of 0.5 mM dATP, 0.5 mM dGTP, 0.5 mM dCTP and 0.5 mM dTTP were added and the reactions were incubated for an additional 15 minutes. The reactions were stopped by adding 12 ul of 95% formamide and 10 mM EDTA pH 8.0. The samples were heated to 95° C. and loaded on denaturing acrylamide gels containing 8 M urea, 90 mM Tris pH 8.3, 90 mM boric acid and 2 mM EDTA. Gels were fixed in 10% acetic acid, 10% methanol, dried and autoradiographed.

6.2. IDENTIFICATION AND SEQUENCING OF THE POLYHEDRIN GENE OF HELIOTHIS ZEA VIRUS

*Heliothis zea* DNA was obtained from virus isolated from *Heliothis zea* infected larvae. Viral HindIII and XhoI fragments were cloned into the HindIII and SalI site, respectively, of pUC12. Two plasmids were characterized: pHH5 which contains a 3.1 kb HindIII virus fragment and pHX12 which contains a 6.5 kb XhoI virus fragment. Both inserts cross-hybridized under relaxed stringency conditions to a DNA fragment encoding part of the Autographa polyhedrin gene.

Restriction maps of pHH5 and pHX12 demonstrated that the pHH5 insert is contained within pHX12. Southern blots of pHH5 using the Autographa polyhedrin gene as a probe indicated that a 1.7 kb NruI fragment cross-hybridized to the Autographa polyhedrin gene. HincII and HindIII/SalI fragments of pHH5 and the HindIII/EcoRI fragments of pHX12 were subcloned into M13mp18 (Yanisch-Perron, C., et al., 1985, Gene 33:103-119). The EcoRI/NruI fragment of pHE2.6 (described infra in Section 6.3.2.) and the EcoRI/HindIII fragment of transfer vector 1 (described infra in Section 6.3.4.) were also subcloned. The DNA sequence of selected subclones was determined using the dideoxy chain termination method (Sanger, F., et al., 1977, Proc. Natl. Acad. Sci. U.S.A. 74:5463-5467). The sequencing strategy used is diagrammed in FIG. 1B. The sequence of the Heliothis polyhedrin gene is shown in FIG. 1. A restriction enzyme map for the restriction endonucleases HindIII, NruI, HincII, and AccI was derived from the nucleotide sequence and is shown in FIG. 1A. The digest fragments and sizes are shown in Table II.

TABLE II

HindIII/NruI/HincII/AccI RESTRICTION ENZYME DIGESTION FRAGMENTS OF THE HELIOTHIS POLHEDRIN GENE[1]
List of Fragments from 5' to 3' End

| Fragment # | Fragment size | Starts at | Ends at |
| --- | --- | --- | --- |
| 1 | — | —* | +2 |
| 2 | 250 | +3 | +252 |
| 3 | 9 | +253 | +261 |
| 4 | 14 | +262 | +275 |
| 5 | 12 | +276 | +287 |
| 6 | — | +288 | —* |

[1]Fragments shown are those expected from the DNA sequence of the Heliothis polyhedrin gene shown in FIG. 1, after digestion with HindIII, NruI, HincII, and AccI.
*Not within the sequenced region.

Comparison of the DNA sequence of the subclones with that of the Autographa polyhedrin gene was used to identify the coding sequence of the Heliothis polyhedrin gene. The DNA sequence of the region shown in FIG. 1 reveals an open reading frame of 753 nucleotides. The 7th codon of the open reading frame encodes a methionine which is followed by a sequence encoding 244 amino acids which have 84% amino acid sequence homology to the autographa polyhedrin sequence. This sequence terminates with a TAA codon as found in the corresponding position of the Autographa gene. We defined the first methionine in this open reading frame as the initiating codon of the Heliothis polyhedrin gene.

If the Autographa (MNPV) and Heliothis (SNPV) polyhedrin amino acid sequences are aligned to maximize sequence homology, there is 84% sequence homology between the two proteins. This compares with 77% sequence homology between Heliothis (SNPV) and Bombyx mori (MNPV) proteins (FIG. 2). The Autographa and Bombyx proteins also share 84% sequence homology. If the tyr-ser-tyr sequence at amino acid residues 5-7 of the Heliothis sequence mark the beginning of the homology between the two proteins, the Heliothis sequence contains an insertion of an additional amino acid residue at the amino terminus as compared with the Autographa and Bombyx proteins. There are 36 amino acid substitutions between the Autographa and Heliothis proteins as well as a deletion of an amino acid between positions 226 and 227 of the Heliothis sequence.

The Heliothis and Bombyx sequences are somewhat more divergent, sharing only 77% sequence homology. In addition to the 52 amino acid substitutions, there are two single amino acid insertions as well as two deletions in the Heliothis sequence. Interestingly, of the four deletions and insertions between these two sequences, one insertion and one deletion are found in the Heliothis-Autographa comparison and the other insertion and deletion are found in the Autographa-Bombyx comparison. This suggests that the evolutionary divergence between Autographa and either Heliothis or Bombyx is approximately the same and that Heliothis and Bombyx are more highly divergent. Similar conclusions can be reached by comparing the overall sequence homology of the polyhedrin proteins of the three species. There does not appear to be a relationship between the degree of sequence divergence and whether the virus is an SNPV or MNPV. The degree of sequence divergence between Autographa (MNPV) and either the Heliothis (SNPV) or Bombyx (MNPV) is similar.

The pattern of hydrophilicity is very similar for the Autographa and Heliothis proteins (FIG. 3). Interestingly, the region of highest hydrophilicity of the polyhedrin proteins is the region of greatest sequence divergence. There is only 54% sequence homology between the Autographa and Heliothis polyhedrins in the region between amino acids 38 and 50 of the sequence. The Autographa and Bombyx sequences share only 31% sequence homology, while the Heliothis and Bombyx sequences are 39% homologous in this region. These values compare with approximately 80% sequence homology for the entire protein. Conceivably, these hydrophilic regions identify a site involved in some species specific interaction with other viral or cellular components. Small peptides generated from this region perhaps may be used to raise monoclonal antibodies that could discriminate among different baculoviruses.

6.3. CONSTRUCTION OF TRANSFER VECTORS

The plasmids pHH5 and pHX12 were used to construct a transfer vector, termed pHE2.6, which allows for the insertion of foreign genes within the polyhedrin gene sequence so that recombinant Hz viruses containing the foreign genes can be produced via in vivo recombination.

The construction of this transfer vector is outlined in FIG. 5A, which should be referred to in order to simplify the description that follows.

6.3.1. PARENT PLASMIDS: pHH5 AND pHX12

The preparation of pHH5 and pHX12 is described above in Section 6.2. The pHH5 plasmid contains a 3.1 kb HindIII fragment of the Hz virus DNA (starting from nucleotide residue number 253 of the polyhedrin gene sequence depicted in FIG. 1) in the HindIII site of pUC12 (FIG. 5A). The HindIII Hz DNA insert of pHH5 encodes approximately two-thirds of the polyhedrin gene comprising the carboxy-coding region (i.e., approximately one-third of the polyhedrin coding sequence comprising the amino-coding region is missing). The polyhedrin gene sequence is oriented so that the polylinker of the pUC12 parent plasmid is located upstream or 5' to the polyhedrin gene sequence (FIG. 5A).

The XhoI Hz DNA insert of the pHX12 plasmid contains the entire polyhedrin gene sequence inserted into the SalI site of pUC12. The Hz polyhedrin gene sequence in pHX12 is oriented in the opposite direction with respect to the pUC12 polylinker as compared with the Hz polyhedrin coding sequence contained in pHH5; that is, the EcoRI site of the polylinker of pUC12 is located 3' to the polyhedrin gene sequence in pHX12 (FIG. 5A).

6.3.2. CONSTRUCTION OF TRANSFER VECTORS

A restriction fragment of pHX12, containing portions of the amino-coding terminus of the Hz polyhedrin gene sequence, was used to reconstruct the polyhedrin gene in pHH5 so that a transfer vector containing the polyhedrin gene sequence interrupted at its amino-coding terminus by a multiple cloning site (MCS) would be produced.

The pHX12 plasmid was cleaved with EcoRI and NruI, and an approximately 1125 bp EcoRI-NruI fragment, containing the promoter and amino-terminal portion of the Heliothis polyhedrin gene, was isolated. This 1125 bp fragment was cloned into the EcoRI and SmaI sites of the pUC12 polylinker in pHH5. The BamHI to PstI sequence of the polylinker of this clone was then replaced with a synthetic oligonucleotide containing various restriction endonuclease recognition sites (a multiple cloning site, MCS). The sequences at the cloning junctions of the oligonucleotide were confirmed by DNA sequence analysis.

The resulting plasmid, termed pHE2.6, contains the polyhedrin 5' flanking region including promoter sequences, 5' polyhedrin coding sequences, an MCS, 3' polyhedrin coding sequences, 3' polyhedrin flanking region, and pUC12 sequences. Foreign gene sequences can be inserted into the polylinker and the resulting plasmid vector can be used to transfect host cells infected with *Heliothis zea* virus. Hz virus recombinants will be formed which contain the foreign gene and direct its expression using the polyhedrin promoter.

6.3.3. TRANSFER VECTORS EXPRESSING BETA-GALACTOSIDASE

Figure 5B:
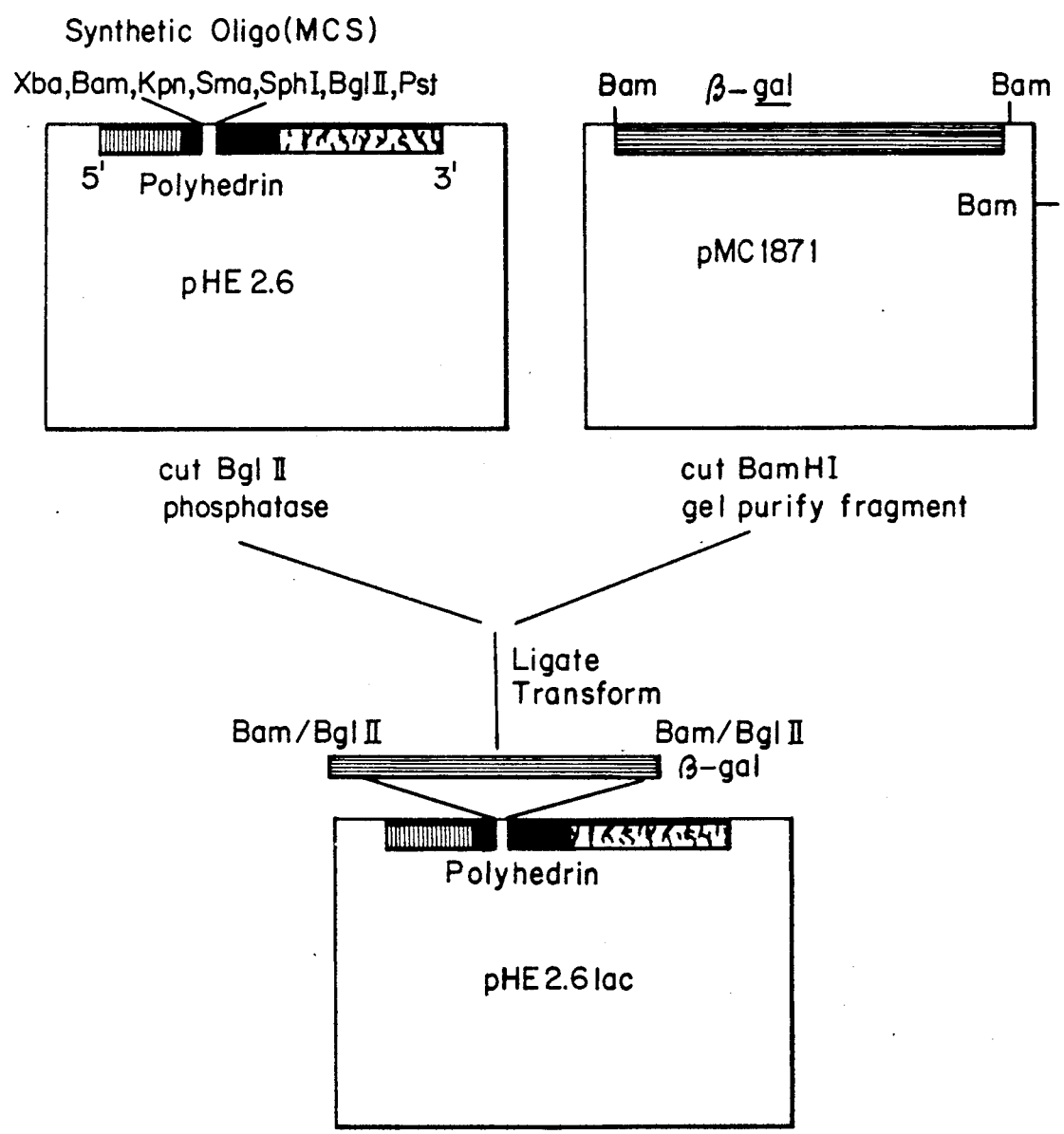

A transfer vector, termed pHE2.61ac, was constructed to contain the *E. coli* beta-galactosidase (B-gal) gene inserted within an MCS flanked by Heliothis polyhedrin sequences (FIG. 5B). A 3 kb fragment of plasmid pMC1871 (Pharmacia), containing the *E. coli* B-gal gene, was isolated by cleavage with BamHI followed by gel purification. Plasmid pHE2.6 was cleaved with BglII, treated with bacterial alkaline phosphatase, and ligated (T4 DNA ligase) to the pMC1871-derived fragment in order to insert the B-gal gene into the BglII site of pHE2.6. The resulting plasmids contained the B-gal gene in both orientations (5' to 3', and 3' to 5') with respect to the polyhedrin promoter and coding sequences. *E. coli* strain DH1 was transformed with the resulting plasmids, and the identity of transformants was confirmed by DNA fragment size determinations upon restriction digestion of their plasmid DNA. *E. coli* strain DH5 alpha (Bethesda Research Laboratories) was also transformed with the B-gal-containing plasmids, and the resulting transformants were tested according to the "blue-white" screening technique of Messing et al. (1977, Proc. Natl. Acad. Sci. U.S.A. 74:3642-3646). Briefly, the transformed bacterial cells were mixed with the chromogenic substrate "X-gal" (5-bromo-4-chloro-3-indolyl-B-D-galactopyranoside) before plating. Blue bacterial colonies arise from bacteria containing plasmids that express functional B-gal activity. Such plasmids contain a beta-galactosidase gene which encodes the enzyme responsible for hydrolysis of "X-gal" and resultant production of a blue 5-bromo-4-chloro-indigo. Bacteria harboring plasmids that do not express functional B-gal activity give rise to white colonies since there is no ability to hydrolyze the chromogenic substrate.

The plasmid construction which contained B-gal in the appropriate orientation produced blue colonies indicative of beta-galactosidase activity. This plasmid was termed pHE2.61ac. pHE2.61ac was determined by appropriate restriction digestions to contain the B-gal gene in the proper orientation (i.e. the same 5' to 3' direction) to the polyhedrin promoter. Those transformants containing the parental plasmid pHE2.6 or the B-gal gene in the wrong orientation produced only white colonies. This result suggested that there is low level expression of the B-gal fusion gene from sequences that have promoter activity in *E. coli*. This promoter activity may be originating from the polyhedrin promoter, since the polyhedrin promoter sequences may assume secondary structures which provide for cross-species promoter activity. The observed B-gal expression indicates that the B-gal sequences are in the appropriate reading frame, and that the fusion protein is enzymatically active.

Plasmid pHE2.61ac has been used in co-transfections with Heliothis virus into cells in order to transfer the B-galactosidase gene fusion into Heliothis virus. The production of blue plaques indicated the expression of a foreign gene, *E. coli* beta-galactosidase, as provided for by the present invention. The expression of B-galactosidase in the HzNPV expression system, and the characterization of the recombinant Heliothis viruses expressing B-galactosidase are described infra in Section 11. Heliothis viruses expressing beta-galactosidase can also be used as the parental virus for further manipulations involving insertions and deletions of the polyhedrin gene, through transfection of parental virus-infected cells with transfer vectors such as plasmid pHE2.6. Selection of the appropriate recombinant viruses would be greatly facilitated by detection of white plaques amidst a background of blue plaques.

Alternatively, another gene may be inserted into transfer vector pHE2.61ac downstream of the B-gal gene, in the proper reading frame. Selection of "blue" transformants would enable isolation of those bacterial colonies also containing the second heterologous gene. This transfer vector can then be used for transfer into Heliothis virus by transfection into infected cells and selection for blue plaques. In a particular embodiment, this second gene could comprise the Autographa polyhedrin promoter. A SalI-BamHI fragment can be isolated from pEcoRI-I which contains the promoter and 5' region of the Autographa polyhedrin gene. This fragment can be inserted by DNA termini modifications (such as described in Section 5.2.1., supra) into the PstI site of the MCS downstream of B-gal in pHE2.61ac. The resulting plasmid would contain the Heliothis polyhedrin promoter and 5' coding sequences, B-gal, Autographa polyhedrin promoter and 5' coding sequences, and 3' Heliothis polyhedrin coding sequences. A foreign gene can potentially be inserted and expressed under the control of one of the polyhedrin promoters. The plasmid can then be used as a transfer vector for insertion into Heliothis virus by in vivo recombination.

6.3.4. GENERATION OF DELETIONS OF HELIOTHIS POLYHEDRIN AMINO-TERMINAL SEQUENCES

Figure 5C:
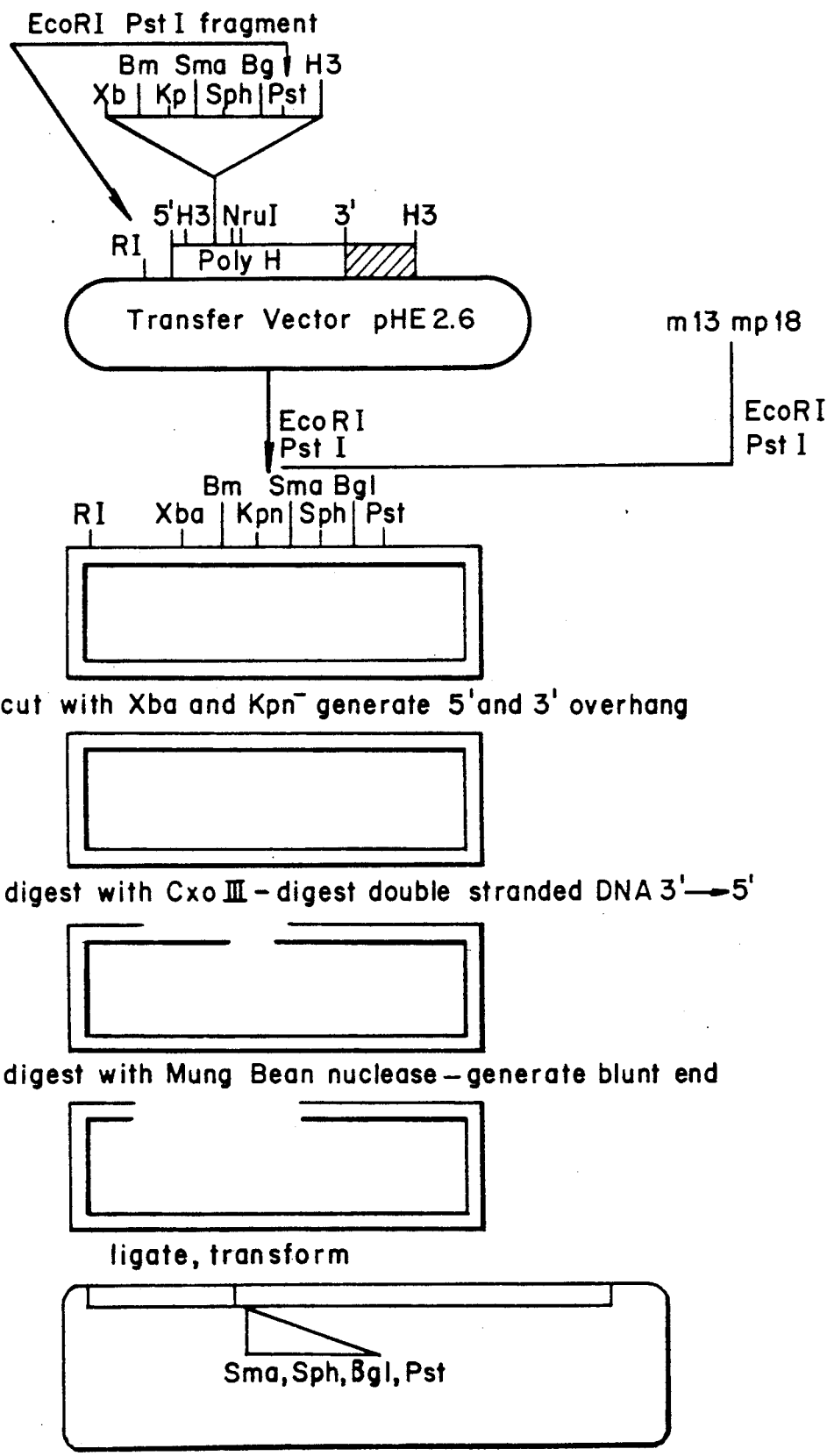

The strategy we have used to create deletions in the amino-terminus of the polyhedrin gene in Heliothis transfer vectors is diagrammed in FIG. 5C.

Plasmid pHE2.6 was digested with EcoRI and PstI. A 1.1 kb EcoRI-PstI fragment containing the Heliothis polyhedrin gene was generated, which was subcloned into M13mp18. The double-stranded replicative form of the resulting M13 derivative was digested with XbaI and KpnI, which cut within the MCS, to generate a single-stranded 5' overhang at the XbaI cleavage site and a single-stranded 3'60 overhang at the KpnI cleavage site. The resulting DNA was treated with Exonuclease III (exo III) which digested a single strand of the double-stranded DNA for a variable length in the 3' to 5' direction starting from the XbaI-cleaved end. The KpnI-cleaved end which has a 3, overhang is resistant to exo III digestion. The DNA was then digested with Mung Bean nuclease, which digests single-stranded DNA, to generate blunt ends by removing the single-stranded DNA left after exo III digestion. The blunt ends were ligated together with DNA ligase, resulting in transfer vectors that contain deletions of various length within the N-terminal portions of the Heliothis polyhedrin gene. The transfer vectors thus derived contain the Heliothis polyhedrin promoter, 5' polyhedrin regions of various length, an abbreviated MCS, and 3′ polyhedrin sequences.

Thus far, three N-terminal deletion transfer vectors have been obtained in this fashion. Transfer vector 1 has a 282 base pair (bp) deletion spanning nucleotide number 63 of FIG. 1 through the KpnI site. Transfer vector 2 has a 274 bp deletion spanning nucleotide number 71 of FIG. 1 through the KpnI site. Transfer vector 3 has a deletion which spans the initiator methionine codon, and thus provides for the production of nonfusion heterologous proteins under the control of the Heliothis polyhedrin promoter. Vector 3 has a deletion spanning nucleotide number $-36$ of FIG. 1 through the KpnI site. The deletion of the initiator methionine codon can permit manipulation of the amino-terminal portion of the heterologous protein to be produced, by allowing the expression of a variety of gene sequences which can be inserted within the region of the deletion and which contain an initiator methionine codon which will then encode the amino-terminal portion of the nonfusion heterologous protein.

7. EXAMPLE

HELIOTHIS VIRUSES FOR USE IN HELIOTHIS EXPRESSION SYSTEMS

Twenty plaque-purified strains of HzSNPV were characterized based on their restriction endonuclease digestion patterns of viral DNA, structural protein profiles, and larval melanization response. Each of the twenty strains had a unique genotype. Genomic heterogeneity between strains was localized to four regions of the HzSNPV genome. Differences in the protein profiles of occluded virus were noted for each strain relative to the wild-type isolate. The strains were separated into three groups based upon differences in relative virulence and rate of larval melanization upon death. There was no correlation between differences in pathology and specific alterations in either genotype or structural proteins. The genotype of the weakly melanizing strain, HzS-15, was extensively characterized. Physical maps were constructed for the HzS-15 strain and all of the plaque purified strains.

7.1. MATERIAL AND METHODS

7.1.1. IN VITRO PROPAGATION OF HzSNPV

Infectious hemolymph was obtained from fifth instar *H. zea* larvae five days post infection, and before melanization. Hemolymph was collected by clipping a proleg and bleeding 10 larvae into 5 ml of TNM-FH medium (Hink, W. F. and Strauss, E., 1976, J. Invert, Path. 27:49–55) containing $5\times10^{-3}$ M 1-cysteine-HCl and $5\times10^{-3}$ M dithiothreitol. The diluted hemolymph was filter-sterilized and used as inoculum for IPLB-HZ1075 cells (Goodwin, R. H., et al., 1982, In Vitro 18:843-850) adapted for growth in TNM-FH medium. Inoculation of cell cultures was accomplished by adding 5 ml of filtered inoculum to a 24 hour old monolayer of $1.0\times10^6$ IPLB-HZ1075 cells in a tissue culture flask (25 $cm^2$). After one hour at 29° C., the inoculum was removed and the monolayer washed once with fresh media. Five ml of TNM-FH was added and the cultures were incubated at 29° C. and monitored at 24 hour intervals for the presence of occlusion bodies.

7.1.2. PLAQUE PURIFICATION OF HzSNPV ISOLATES

Plaque assays were performed on supernatants of cell cultures infected with the larval-isolated HzSNPV as previously described (Fraser, 1982, J. Tis. Cult. Meth. 7:43–46). Twenty-four wild-type (MP type) plaques were picked and used as inoculum for $1\times10^5$ cells in each well of a 24 well plate. These once-plaque-purified isolates were re-assayed and individual plaques from the second assay were amplified first in 24-well plate cultures, and then in 25 $cm^2$ flask cultures of IPLB-HZ1075 cells.

7.1.3. MAINTENANCE OF H. ZEA AND LARVAL PROPAGATION OF VIRUS

*H. zea* larvae were maintained on a pinto-bean, agar-based diet (Ignoffo, C. M., 1963, Ann. Ent. Soc. Am. 56:178–182) at 29° C, 75% relative humidity, and 12 hour photoperiod.

Individual strains were amplified by direct oral inoculation of one to two inch long Heliothis zea larvae (third to fourth instar) with occlusion bodies isolated from the second cell culture passage of each plaque-purified strain. Infections were allowed to progress for 4 to 7 days before collecting the larvae. Larvae infected with each isolate were separated into either melanized or non-melanized pools upon collection, and both pools were frozen at $-20°$ C. until use.

7.1.4. ISOLATION OF VIRIONS FROM OCCLUSION BODIES

Infectious occlusion bodies (OBs) were harvested from pools of infected, non-melanized larvae by homogenization in TE buffer (10 mM Tris-HCl, 1mM EDTA, pH 7.6) containing 0.1% SDS. The larval homogenate was filtered through two layers of cheesecloth and centrifuged at $1,800\times g$ for 15 minutes. The supernatants were discarded and the OB pellet washed twice by resuspension in 20 ml of TE buffer and centrifugation at $1,800\times g$. The washed OBs were resuspended in a final volume of 10 ml TE buffer.

Virions were isolated from the washed, partially purified OBs according to the procedure of Smith and Summers (1978, Virology 84:390–402) with slight modifications. Five ml of dissolution buffer (0.3 M $Na_2C0_3$, 0.03

M EDTA, 0.51 M NaCl, pH 10.9) was added to 10 ml of washed OBs (approximately 15 mg/ml), and the OBs were dissolved by incubation for 10 minutes at room temperature. The mixture was layered on 20–60% (w/w) sucrose gradients (in TE buffer) and centrifuged at 75,000×g for 60 minutes at 4° C. The single visible virion band was collected, diluted with an equal volume of TE buffer, and the virions pelleted at 55,000×g for 30 minutes (4° C.). The pelleted virions were resuspended in distilled water and stored at −20° C. until use.

7.1.5. BIOASSAYS AND $LT_{50}$ ANALYSIS

Surface treatment bioassays (Ignoffo, C. M., 1966, J. Invert. Path. 8:531–536) were performed on selected virus strains and the wild-type Elcar TM isolate. Aliquots (100 ul) of each OB dilution were spread evenly upon the surface of an agar based diet that had been solidified in one-ounce plastic portion cups (Fabri-Kal Corp., Kalamazoo, MI). The total surface treated was approximately 679 mm$^2$ in each cup, and the OB dilutions increased in ½ log increments from $1 \times 10^7$ OB/ml (1473 OB/mm$^2$) to $1 \times 10^5$ OB/ml (14.73 OB/mm$^2$). A total of thirty neonate larvae (24 hours old, one per cup) were inoculated with each dilution and monitored daily for mortality (as measured by unresponsiveness to probing). The $LT_{50}$ values and 95% fiducial limits for each bioassay were calculated using a SAS probit (Finney, D. J., 1971, Probit Analysis, Cambridge University Press, London, U. K.) analysis (SAS Institute Inc., Cary, NC).

7.1.6. ISOLATION OF VIRAL DNA

Gradient-purified virions were incubated in TE buffer containing 0.1% KCl, 0.1% SDS, and 0.1 mg/ml proteinase K (Sigma) for 3 hours at 65 C. Following two extractions with phenol and two extractions with chloroform:isoamyl alcohol (24:1), the DNA was precipitated by the addition of 1/10 volume of 2 M sodium acetate, and 2 volumes of 95% ethanol. The precipitated DNA was pelleted at 1,800×g for 15 minutes and resuspended in sterile distilled water at 65° C. for 30 minutes, and stored at 4° C. until use.

7.1.7. RESTRICTION ENDONUCLEASE ANALYSIS

Viral DNAs were digested with BamHI, EcoRI, EcoRV, HindIII, KpnI, PstI, and SstI restriction endonucleases (Bethesda Research Laboratories) under conditions specified by the supplier. Restriction enzyme fragments were separated by electrophoresis in 0.75% agarose gels (20×20 cm) in Tris-acetate buffer (0.04 M Tris-acetate, 0.1 mM EDTA, pH 8.0) containing 0.25 ug/ml ethidium bromide. Gels were electrophoresed for 17 hours at 70 volts and DNA fragments detected with UV light (306 nm). Gels were photographed using a Kodak Wratten 23A filter and Polaroid type 55 positive/negative film.

7.1.8. SDS-POLYACRYLAMIDE GEL ELECTROPHORESIS

Structural proteins of virions released from occlusion bodies by alkali treatment were compared by electrophoresis in discontinuous polyacrylamide slab gels according to the method of Laemmli (1970, Nature 227:680). Virion proteins were solubilized by boiling for 3 minutes in denaturation buffer (62.2 mM Tris-HCl, 2.0% SDS, 20% glycerol, 2.5% dithiothreitol, pH 6.8) at a concentration of 1 mg protein/ml. Electrophoresis was carried out at 30 milliamps for 4.5 hours in a 12% separating gel (10 cm long ×12 cm wide×1.5 cm thick). Gels were stained with 0.125% Coomassie brilliant blue R-250 following standard protocols (Summers, M. D. and Smith, G. E., 1978, Virology 84:390–402; Monroe, J. E. and McCarthy, W. J., 1984, J. Invert. Path. 43:32–40).

7.1.9 RESTRICTION FRAGMENT CLONING AND HYBRIDIZATION ANALYSIS

Viral DNA was bidirectionally transferred to nylon membranes (Micro Separation Inc.) following the methods of Smith and Summers (1980, Anal. Biochem. 109:123–129). A total of 10 ug of HzS-15 viral DNA was digested with BamHI, HindIII or PstI, and electrophoresed in preparative 0.75% agarose gels as described above. Gels were prepared for transfer to nylon as previously described for nitrocellulose (Smith, G. E. and Summers, M. D., 1980, Anal. Biochem. 109:123–129) and blotted for 1.5 to 3 hours. The membranes were rinsed in 0.1X SSC (SSC = 150 mM NaCl, 15 mM sodium citrate, pH 7.5) following transfer, dried for one hour at 45° C., and then baked for one hour under vacuum at 80° C. Baked membranes were stored at room temperature until needed. Strips (3 mm) were cut from these preparative gel blots for hybridization to individual probes.

DNA probes for hybridization analyses were prepared from BamHI, HindIII and PstI fragments of the HzS-15 genome cloned in the pUC8 plasmid vector (Vieria, J. and Messing, J., Gene 19:259–286). Cloned fragments were labeled with photoactivatable biotin (PAB; Clonetech Laboratories, Inc., Palo Alto, Calif.). One microgram of plasmid DNA (1 mg/ml) was mixed with an equal volume of PAB (1 mg/ml) and irradiated in an ice bath for 10 minutes with a sunlamp (275 watts, General Electric Co., Cleveland, Ohio). The volume was adjusted to 100 ul with dilution buffer (10 mM Tris-HCl (pH 7.9), 0.1 mM EDTA) and the unincorporated PAB was removed by centrifuging the mixture through a G-50 Sephadex column at 225×g for 5 minutes. Labeled probes were stored at −20° C. until use.

Nylon membrane-bound restriction enzyme-digested DNA fragments were prehybridized in hybridization buffer (5X Denhardts, 0.1X PBS, 5X SSC, 0.15 mg/ml calf thymus DNA, and 45% formamide) for 8 hours at 45° C. Heat denatured, biotinylated DNA probes were added to the hybridization buffer at a concentration of 100 ng/ml, and hybridized for 12 to 24 hours at 45° C with occasional rocking.

Regions of homology were identified using the detection system provided by the supplier (Clonetech Laboratories Inc.) with slight modifications. Hybridized membranes were washed twice in both 2X SSC, 0.1% SDS and 0.2X SSC, 0.1% SDS for 3 minutes at room temperature and then in 0.15X SSC, 0.1% SDS for 15 minutes at 45° C. The membranes were briefly rinsed in 2X SSC and soaked in Buffer A containing 1% gelatin (Buffer A = 1 M NaCl, 0.1 M Tris-HCl (pH 7.5), 2 mM MgCl$_2$, 0.05% Triton X-100) for 30 minutes. A total of 5 to 10 ug of streptavidin-conjugated alkaline phosphatase (SAP) was added to fresh Buffer A +1% gelatin, and the membranes were soaked for an additional one hour at room temperature. The membranes were washed three times in Buffer A and once in Buffer C (0.1 M NaCl, 0.1 mM Tris-HCl (pH 9.5), 10 mM MgCl$_2$). The hybridized, biotin-labeled bands developed color in Buffer C containing 1.6 mg/ml of Nitro Blue Tetrazolium (Sigma Chemical Co., St. Louis, Mo.) and 5-bromo-4-chloro-3-indolyl phosphate (Sigma). The reaction was stopped by rinsing the membranes in deionized water and air drying.

7.2. CHARACTERIZATION OF HzSNPV

7.2.1. IN VITRO PROPAGATION AND PLAQUE PURIFICATION

The IPLB-HZ1075 insect cell line grew well in TNM-FH medium supplemented with 8% fetal calf serum. Cells remained susceptible to infection by HzSNPV, but infectivity was not 100% under these conditions. The highest levels observed were between 50 and 70% infected cells with maximal titers of $5 \times 10^6$ plaque forming units per ml. The best infections were achieved when cells were allowed to grow at least 24 hours before inoculation with virus. We have since discovered that the addition of 1% bovine serum albumin (BSA) and 2 g/l L-glutamine to the growth medium improves infectivity to about 100%.

Plaques were produced on monolayers of IPLB-HZ1075 cells using the procedures described previously (Fraser, 1982, J. Tis. Cult. Meth. 7:43–46; Fraser and McCarthy, 1984, J. Invert. Path. 43:427–429). No FP-like plaques (few polyhedra) were observed in this study. All plaques picked for isolation exhibited the wild-type morphology and produced many occlusion bodies per infected cell.

7.2.2. LARVAL INFECTIONS WITH OCCLUSION BODIES

The plaque-purified strains were amplified in third to fourth instar H. zea larvae. Larval propagation was necessary to rapidly expand the virus and reduce the probability of selecting in vitro passage mutants.

Mutant selection is a phenomenon which occurs readily during in vitro propagation of baculoviruses (Potter, K. N., et al., 1976, J. Virol. 18:1040–1050; Hink and Strauss, 1976, J. Invert. Path. 27:49–55; Fraser and Hink, 1982, Virology 117:366–378; Fraser and McCarthy, 1984, J. Invert. Path. 43:427–429), but is not observed during short term in vivo propagations of HzSNPV (McIntosh, A. H. and Ignoffo, C. M., 1986, Intervirol. 25:172–176).

To amplify the virus in larvae, the inoculations were performed by placing a drop of a $1 \times 10^6$ OB/ml suspension directly on the head capsule of each larvae. Larval derived OBs were used for subsequent inoculations to characterize the relative virulence and degree of pathogenicity of each strain and the wild-type isolate.

During these in vivo amplifications, we noted differences in the gross pathology of several plaque-purified strains relative to the pathology of the wild-type isolate. Many of the plaque-purified strains caused rapid melanization and instability of the cuticle upon death of the larvae, a pathology normally seen following infection with HzSNPV. In contrast, several strains caused mortality without the usual attendant rapid melanization and cuticular breakdown.

The plaque-purified virus strains could be separated into three groups based on their relative ability to cause melanization in infected third instar larvae (Table III).

TABLE III

| Separation of HzSNPV Elcar ™ Strains on the Basis of Ability to Cause Melanization | |
|---|---|
| Melanization Ability | Isolate |
| Rapid Melanization and Death | W+, 1, 2, 4, 11, 12, 13, 14, 17, 18, 20, 23 |
| Slow Melanization and Death | 5, 7, 8, 9, 21, 22, 24, 25 |
| No Melanization[a] | 15 |

[a]"No Melanization" is defined as less than 30% melanization by nine days after larval death.

The wild-type virus isolate (W+) and several of the plaque-purified strains (1, 2, 4, 11, 12, 13, 14, 17, 18, 20, 23) caused larval death within four to five days post inoculation. The dead larvae rapidly melanized over a period of 1 to 3 hours, turning a dark brown overall, and the cuticle was easily disrupted.

Larvae infected with several other strains (5, 7, 8, 9, 15, 21, 22, 24, 25) also reached apparently complete infection by 4–5 days post inoculation as evidenced by the abundance of occlusion bodies in infected tissues, but the larvae did not die or melanize rapidly. The larvae became soft and incapable of motion in the posterior two-thirds of the body after 4–5 days, but actual death (i.e., unresponsiveness to probing) and subsequent melanization required several more days, and in some cases even weeks, e.g. HzS-15.

Strain HzS-15 caused a similar pathology to the other slow-melanizing strains. However, HzS-15 was remarkable in that most larvae infected with this strain did not begin melanizing until greater than 7 days post inoculation, with many taking several weeks to completely melanize. Furthermore, HzS-15 is highly virulent.

To further characterize these apparent differences in pathology between plaque-purified strains, we standardized the inoculations for all strains using a surface treatment bioassay Two neonate (24 hour old) H. zea larvae were added to each of 10 plastic portion cups (1 ounce) containing an agar based diet (Ignoffo, C. M., 1963, Ann. Entom. Assoc. Am. 56:178–182) that had been surface treated with 100 ul of a $1 \times 10^7$ OB/ml (1473 OB/mm2) dilution. Larvae were monitored daily for mortality (as measured by unresponsiveness to probing) and melanization (as measured by coloration and cuticular disruption upon prodding). All infected larvae died within 4 days post infection at this dosage.

Three groupings of the virus strains were generated, based upon relative percentages of larvae melanizing within a given time period (Table IV), essentially confirming the earlier observations (Table III).

TABLE IV

| PERCENTAGE OF LARVAE MELANIZING OVER TIME | | | | | |
|---|---|---|---|---|---|
| Melanization | | Days After Larval Death | | | |
| Rate | Strain | 0–1 | 2–3 | 4–9 | 9 |
| rapid melanization[a] | W+ | 75 | 25 | — | — |
| | 1 | 80 | 20 | — | — |
| | 2 | 81 | 19 | — | — |
| | 4 | 95 | 5 | — | — |
| | 11 | 80 | 20 | — | — |
| | 12 | 78 | 17 | 5 | — |
| | 13 | 94 | 6 | — | — |
| | 14 | 94 | 6 | — | — |
| | 17 | 88 | 12 | — | — |
| | 18 | 93 | 7 | — | — |
| | 20 | 100 | — | — | — |
| | 23 | 85 | 8 | 5 | 5 |
| slow | 5 | 6 | 0 | 26 | 67 |

TABLE IV-continued

PERCENTAGE OF LARVAE MELANIZING OVER TIME

| Melanization Rate | Strain | Days After Larval Death | | | |
|---|---|---|---|---|---|
| | | 0-1 | 2-3 | 4-9 | 9 |
| melanization[b] | 7 | 10 | 20 | 20 | 50 |
| | 8 | 5 | 5 | 37 | 53 |
| | 9 | 19 | 6 | 31 | 56 |
| | 21 | 69 | 12 | 13 | 6 |
| | 22 | 44 | 19 | 19 | 18 |
| | 24 | 0 | 7 | 27 | 67 |
| | 25 | 5 | 10 | 35 | 50 |
| non-melanizing[c] | 15 | 5 | 11 | 11 | 73 |

[a]Greater than 90% mortality within 3 days, and at least 75% of the larvae melanized within one day of death.
[b]Greater than 30% of the larvae melanized within 9 days of death.
[c]Less than 30% of the larvae melanized by 9 days after death.

At least 75% of the larvae infected with the rapidly melanizing strains completely melanized within 24 hours of death. The slow melanizing strains produced greater than 30% melanization response within nine days following larval death. Once again, HzS-15 was remarkable, causing less than 30% melanization by nine days post mortality.

The dose response effects of several strains representative of each group from the data of Table IV was tested by calculating $LT_{50}$ values for five OB dilutions of each strain (Table V).

TABLE V

COMPARATIVE $LT_{50}$ ANALYSIS OF SELECTED HzSNPV STRAINS*

| Virus | OB/mm² of diet | | | | |
|---|---|---|---|---|---|
| | 14.73 | 73.66 | 147.3 | 736.6 | 1473.2 |
| HzSNPV W+ | 3.96[a] | 4.37[a] | 4.16[a] | 4.20[a] | 4.44[b] |
| HzS-14 | 6.64[c] | 6.48[b] | 6.68[c] | 5.94[b] | 4.28[b] |
| HzS-15 | 5.80[b] | 6.35[b] | 5.64[b] | 4.19[a] | 3.56[a] |
| HzS-18 | 5.38[b] | 6.14[b] | 5.51[b] | 4.45[a] | 4.44[a,b] |

*Numbers with the same superscript letters are not significantly different at 9% fiducial limits.

Significant differences were indicated by non-overlapping 95% fiducial limits between some of the plaque-purified strains. The wild-type Elcar ™ isolate was the most virulent for all but the highest concentration tested (Table V). HzS-14 was the least virulent strain in all concentrations tested. In general, the $LT_{50}$ values rose with decreasing concentration in each strain. The noteable exception was the wild-type isolate, for which no significant increase in $LT_{50}$ values occurred with decreasing OB concentrations.

7.2.3. RESTRICTION ENZYME DIGESTION PATTERNS OF VIRAL DNAs

Figure 6:
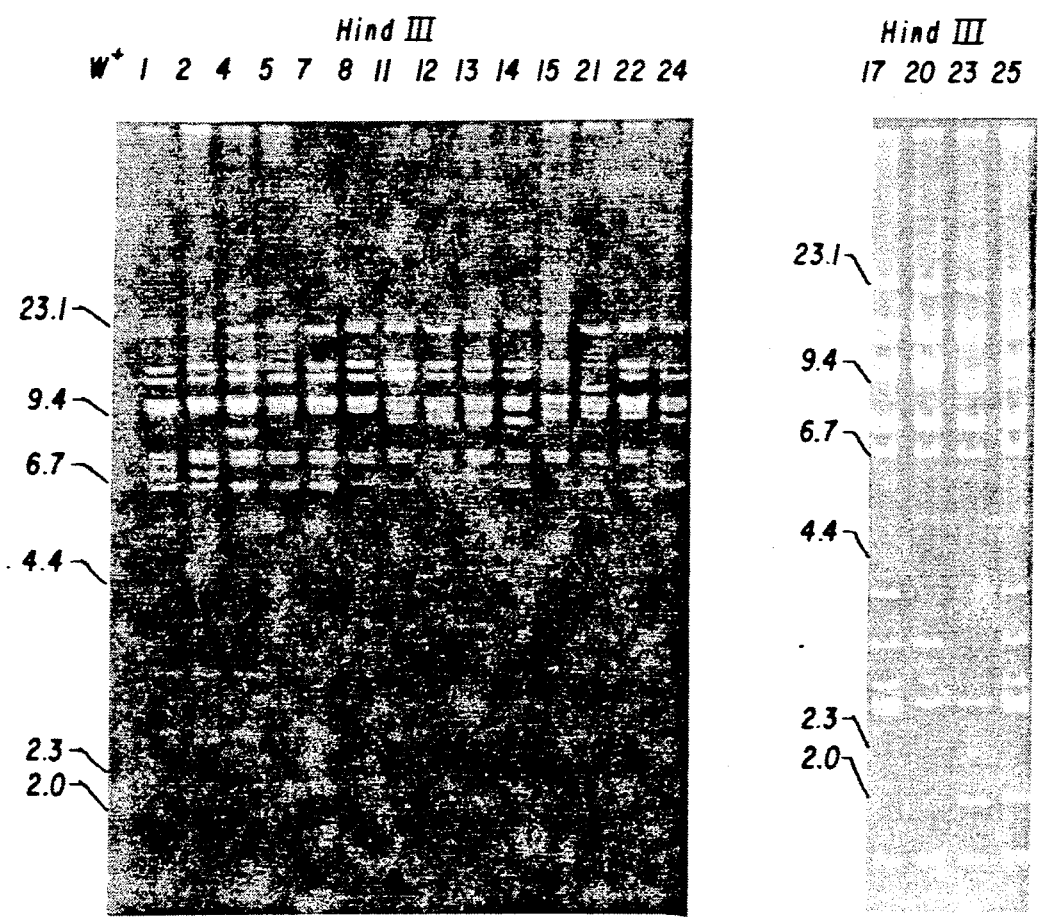

The genomes of all twenty strains were compared following digestions with BamHI, EcoRI, HindIII, and PstI. Each strain could be distinguished from all others on the basis of the combined restriction digestion patterns. No single genotype was predominant. For example, in the HindIII digests there were only five strains with identical fragment patterns (FIG. 6). These five strains could be distinguished from the others upon digestion with BamHI or PstI. Comparisons of viral genomes with several restriction enzymes identified a limited number of variable regions in the HzSNPV genome.

Strain HzS-15 was singled out as unique due to its remarkably long melanization period and complex occluded virion structural protein profile. We compared this strain with the wild-type isolate using several additional enzymes (FIG. 7). The wild-type virus and HzS-15 exhibited similar restriction patterns with enzymes BamHI, KpnI, and PstI, but were distinct upon digestion with the enzymes EcoRI, EcoRV, HindIII, and SstI (FIG. 7). The sizes of the HzS-15 restriction fragments for several enzymes were estimated using the method of Southern (1979, Anal. Biochem. 100:319-323) (Table VI).

TABLE VI

SIZES OF HzS-15 RESTRICTION FRAGMENTS[a]

| Fragment | Enzymes | | | | | | |
|---|---|---|---|---|---|---|---|
| | BamHI | EcoRI | EcoRV | HindIII | PstI | SstI | BamHI + PstI |
| A | 36.46 | 13.39 | 13.94 | 20.81 | 33.62 | 29.92 | 26.07 |
| B | 29.59 | 10.28 | 12.77 | 14.01 | 33.62 | 25.42 | 23.47 |
| C | 14.54 | 9.21 | 10.94 | 13.20 | 33.62 | 23.63 | 14.54 |
| D | 13.87 | 8.31 | 9.24 | 12.47 | 11.39 | 20.07 | 8.15 |
| E | 12.89 | 6.53 | 8.50 | 10.55 | 6.15 | 11.49 | 7.91 |
| F | 7.91 | 6.38 | 8.07 | 10.55 | 3.46 | 9.88 | 6.45 |
| G | 4.02 | 6.11 | 8.07 | 9.97 | 0.56 | 4.31 | 6.15 |
| H | 3.90 | 6.05 | 7.41 | 9.58 | | | 5.12 |
| I | 1.87 | 5.92 | 7.41 | 7.80 | | | 4.75 |
| J | 1.83 | 5.92 | 6.43 | 7.56 | | | 4.33 |
| K | 1.27 | 5.80 | 5.58 | 3.83 | | | 4.02 |
| L | | 4.81 | 3.71 | 2.76 | | | 3.90 |
| M | | 4.59 | 3.23 | 2.58 | | | 3.46 |
| N | | 4.46 | 2.91 | 1.47 | | | 3.08 |
| O | | 4.46 | 2.88 | | | | 1.87 |
| P | | 3.34 | 2.73 | | | | 1.83 |
| Q | | 3.17 | 2.56 | | | | 1.27 |
| R | | 3.09 | 1.67 | | | | 0.56 |
| S | | 2.95 | 1.58 | | | | |
| T | | 2.65 | 1.58 | | | | |
| U | | 1.72 | 1.43 | | | | |
| V | | 0.98 | 0.96 | | | | |
| W | | 0.76 | 0.89 | | | | |
| X | | 0.47 | 0.65 | | | | |
| Y | | | 0.53 | | | | |
| Z | | | 0.43 | | | | |
| AA | | | 0.28 | | | | |

TABLE VI-continued

SIZES OF HzS-15 RESTRICTION FRAGMENTS[a]

| Fragment | BamHI | EcoRI | EcoRV | HindIII | PstI | SstI | BamHI + PstI |
|---|---|---|---|---|---|---|---|
| Total | 125.14 | 121.35 | 126.42 | 127.14 | 122.42 | 124.72 | 126.93 |

[a]Sizes are given in kbp.

The HzS-15 and the wild-type isolate produced similar BamHI restriction patterns, and we began our mapping analysis using the restriction enzyme map of Knell and Summers (1984, J. Gen. Virol. 65:445–450) as a reference. However, our independent hybridization analyses using cloned BamHI, HindIII and PstI fragments as probes forced a reinterpretation of the basic HzSNPV map. A corrected map for HzS-15, and HzSNPV in general is presented in FIG. 8.

Hybridization analysis of other plaque-purified isolates identified four separate regions of variability in the HindIII digests (FIG. 8A). Regions II, III, and IV encompassed conservative alterations in each of the viral isolates. The HzS-23 genotype contained a small insertion in HindIII band F of region III of undetermined origin. All other strains exhibited no significant deletions or insertions in these regions.

Alterations in Region I were more significant. Most of the plaque purified genotypes that had changes in Region I exhibited small deletions or insertions, while only one strain had no significant alterations in fragment size. An insertion in HindIII-D uniquely identified HzS-21 since it was the only isolate which had an alteration outside Regions I-IV.

7.2.4. COMPARISON OF VIRION STRUCTURAL PROTEINS

The varied larval pathology prompted an investigation of potential similarities in structural proteins between strains exhibiting similar pathology.

Virions were liberated from larval-derived occlusion bodies by alkali treatment and purified by banding in linear sucrose gradients. Electrophoresis of occluded virion structural proteins of the wild-type isolate revealed 13 major polypeptide bands following staining with Coomassie blue R-250. These proteins ranged in size from 62.9 to 17.8 kilodaltons (FIG. 9). Five of these polypeptides (VP 32.1, VP 37.2, VP 41.1, VP 49.2, and VP 62.9) were evident in the occluded virion protein profiles of all the plaque-purified strains. The remaining eight wild-type polypeptides varied in occurrence among the plaque-purified strains.

The total number of major polypeptides in each plaque-purified strain varied from a low of 13 to a high of 19, and ranged in size from 17.8 to 84.1 kilodaltons. VP 46.6 was easily visible in profiles of all the plaque-purified strains, but was not apparent in the profile of the wild-type isolate. Other unusual polypeptides were VP 62.0, found only in HzS-21, and several proteins between 21.1 and 25.7 kilodaltons which were evident only in strains 18 through 25.

The HzS-15 strain exhibited most of the wild-type polypeptides except VP 33.8 and VP 66.1, and also exhibited many of the additional polypeptides found individually in several of the other strains. Several protein bands were apparently unique to HzS-15 including VP 51.0, and three bands above VP 69.0.

There was no apparent correlation between the presence or absence of any occluded virion structural proteins and the observed differences in rate of melanization of infected larvae.

8. EXAMPLE
CELL LINE HOSTS FOR USE IN HELIOTHIS EXPRESSION SYSTEMS

A total of twenty-four cloned *Heliothis zea*-derived cell lines (HZ1075/UND-A through X) were initially isolated by dilution plating from the established *Heliothis zea*-derived cell line IPLB-HZ1075. Many of the isolates with highly vacuolated cytoplasms eventually died during subculturing. Surviving cloned cell strains differed in their predominant morphology, cell doubling times, and relative ability to support replication of HzSNPV. The origin of the cloned cell strains was confirmed by comparing their isozyme profiles with those of the parental IPLB-HZ-1075 cell line and *H. zea* larvae using stains for the enzymes FUM, LDH and MDH. One dipteran and several lepidopteran cell lines maintained in our laboratory were also distinguishable using stains for LDH and MDH.

8.1. MATERIALS AND METHODS

8.1.1. CLONING OF CELL STRAINS

The IPLB-HZ1075 cell line was adapted to growth in TNM-FH medium over several passages. Cloning of cell strains was accomplished by diluting the cells to an average density of 1 cell per 100 ul, and plating 100 ul in each well of a 96 well culture plate. The wells were examined after 12 hours and those containing only one cell each were marked. The growth medium for cell clones was composed of an equal mixture of filter- sterilized, conditioned TNM-FH medium and fresh TNM-FH medium (50% conditioned medium). The conditioned medium was obtained from 24 hour old, actively growing cultures of IPLB-HZ1075 cells, and was filter-sterilized to insure no carryover of cells. The strains were maintained in the 96 well plates by replenishing the 50% conditioned medium every 5 days until crowding forced subculturing into 24 well plates.

The cell strains were designated HZ1075/UND-A through X. A total of 24 strains were originally isolated but many eventually died during amplification and subculturing. Of those that survived, one was lost to contamination after only partial characterization.

8.1.2. CELL GROWTH CURVES

Individual tissue culture flasks (25 cm$^2$) were seeded with $1 \times 10^6$ cells of each strain in 3 ml of TNM-FH. The cells were allowed to attach and enter log phase growth for 24 hours after which an initial cell count was made. Three defined regions on the flask were counted at 48 hour intervals for up to 8 days following the initial count. Cell clumping was not a problem for most cell strains, and when it did occur, counts were taken on several focal planes.

8.1.3. QUANTITATION OF OCCLUSION BODIES AND INFECTIOUS EXTRACELLULAR VIRUS PRODUCTION

Each cell strain was evaluated for its relative productivity upon inoculation with a plaque-purified isolate of HzSNPV (HzS-15). Three replicate cultures of each cell strain were seeded at a density of $4.25 \times 10^4$ cells per well in 96 well cluster plates. The cultures were inoculated following a 24 hour attachment period with 50 plaque forming units (PFU)/cell in inoculation medium (IM=TNM-FH supplemented with 1% bovine serum albumin, 14 mM fresh L-glutamine, and 10% fetal bovine serum). Virus absorbed at 29° C. for one hour, and the inoculum was replaced with IM. The cells were monitored for 7 days and the culture medium and cells were each collected for quantitation of ECV and OBs, respectively.

Cells and OBs were pelleted by centrifugation at $15,000 \times g$ for 2 minutes. The ECV-containing supernatants were titered using the 50% tissue culture infectious dose ($TCID_{50}$) method (Yamada et al., 1982, J. Invert. Path. 39:185–191). Tenfold serial dilutions were prepared from the cell culture supernatants harvested from each well. Twenty microliters of each dilution were combined with 180 ul of a HZ1075/UND-K cell suspension ($2.5 \times 10^5$ cells per ml) in IM, and 10 ul of the inoculated cell mix was aliquoted to each of ten wells in a Tarasaki microtiter plate (Lux TM). Wells were scored at seven days post infection for the presence of OBs in cell nuclei, and the $TCID_{50}$ value for each sample was calculated according to Reed and Meunch (1938, Amer. J. Hyg. 27:493–497).

The relative productivity of OBs was estimated for each cell strain in several ways. Infected cells from each well were resuspended in 200 ul TNM-FH media after removal of the infectious supernatants. The percentage of infected versus uninfected cells (based upon the presence of OBs in nuclei) was determined for each well by averaging two separate hemocytometer counts. The percentages for each replicate well were pooled to obtain an overall mean percentage for each strain.

An estimate of the mean number of OBs per cell was calculated for each strain using average OB counts of 15 infected cells from each replicate well. Our estimate of the overall number of OBs produced by each cell strain was calculated by first multiplying the mean number of OBs per cell by the mean number of infected cells for each replicate well, and then averaging these values among the three replicates for each strain.

8.1.4. ISOZYME ANALYSIS OF CELL ISOLATES

Monolayers of cells (25 cm$^2$) were collected and pelleted at $1800 \times g$ for 10 minutes. The media was decanted and the cells resuspended in lysis buffer (lysis buffer=0.0152 M Tris, 0.046 M citric acid, 10% sucrose, 1% Triton X-100, 0.02 mM bromophenol blue). The cells were broken by freezing (at −70° C) and thawing (at 37° C.) three times, and the cell lysates were cleared by centrifugation at $15,000 \times g$ for 3 minutes. Cleared supernatants could be stored at −70° C. for prolonged periods without noticeable alteration of enzymatic activity.

Isozymes were detected following electrophoresis of the cleared cell lysates in 5% polyacrylamide gels in either TBE buffer (81.2 mM Tris, 20 mM boric acid, 1.5 mM EDTA, pH 8.9) for enzymes esterase (EST) and fumarate dehydratase (FUM), or 2X TC buffer (19.4 mM Tris, 4.25 mM citric acid, pH 7.1) for enzymes lactate dehydrogenase (LDH) and malate dehydrogenase (MDH). Vertical slab gels (20 x 20 cm) were run at 350 volts for 2 hours in either TBE buffer or TC buffer, and stained for the respective enzymes following the protocols of Harris and Hopkinson (1977, in Handbook of Enzyme Electrophoresis in Human Genetics, North Holland Publishing Co., Amsterdam, p. 297).

8.2. CHARACTERIZATION OF THE CELL LINES

8.2.1. CELL MORPHOLOGY

Twenty-four cell strains labeled HZ1075/UND-A through X were originally isolated by limited dilution plating in 96-well plates. Many of the strains were composed of cells with extensive vacuolation. Most of these highly vacuolated strains eventually died, leaving a total of 13 strains, one of which was eventually lost to contamination.

The twelve surviving strains were fibroblastic in character, and each could be distinguished based upon a predominant cell morphology. Overall morphologies were characterized as predominantly ellipsoidal with 2 or more extensions (UND-B,C,F,H,M,O,R,U) or irregular with several protoplasmic extensions (UND-G,H,L,K,V). (Note that the UND-H cell population consisted largely of cells of both morphologies.) All cell strains exhibited mixed morphologies even though each had arisen from a single cell. Strain UND-B had the most uniform morphology with predominantly ellipsoid-shaped cells. Strain UND-G was characterized by extensive cytoplasmic vacuolation.

8.2.2. CELL GROWTH CURVES

Cell doubling times for the 12 surviving strains and the parental IPLB-HZ1075 cell line were determined by counting three defined areas of each cell monolayer in 25 cm$^2$ tissue culture flasks at 48 hour intervals for a total of 8 days. All but two of the cell strains reached stationary growth phase by 96 hours. Strain UND-C entered stationary growth phase by 144 hours, while UND-K exhibited a biphasic growth curve with an apparent primary stationary phase from 96 to 144 hours, and a second growth period between 144 and 196 hours (FIG. 10). The population doubling times were calculated for each strain (Table VII) and ranged from 37.33 hours to 65.48 hours. The majority of cell strains had calculated doubling times between 45 and 60 hours.

TABLE VII

| | CELL DOUBLING TIMES AND ESTIMATES OF RELATIVE VIRAL PRODUCTIVITY | | | | |
|---|---|---|---|---|---|
| | DOUBLING TIME (HRS.)[a] | MEAN OB COUNTS[b] | | AVERAGE PERCENTAGE INFECTED CELLS[b] | MEAN $TCID_{50}$ ($\times 10^6$)[b] |
| | | (/CELL) | ($\times 10^5$/CULTURE) | | |
| B | 50.90 | 13.58[c,f] | 18.1[b,c] | 26.4[a,b] | 3.26[a,b] |
| C | 48.30 | 16.09[d,e,f] | 23.2[b,c] | 31.8[a] | 2.10[a,b] |
| F | 59.19 | 15.78[d,e,f] | 19.4[b,c] | 26.2[a,b] | 4.72[a,b] |

TABLE VII-continued

CELL DOUBLING TIMES AND ESTIMATES OF RELATIVE VIRAL PRODUCTIVITY

| | DOUBLING TIME (HRS.)[a] | MEAN OB COUNTS[b] | | AVERAGE PERCENTAGE INFECTED CELLS[b] | MEAN TCID$_{50}$ ($\times 10^6$)[b] |
|---|---|---|---|---|---|
| | | (/CELL) | ($\times 10_5$/CULTURE) | | |
| G | 52.16 | 12.24[f] | 31.2[b] | 18.9[a,b,c,d] | 1.26[a,b] |
| H | 37.33 | 30.88[a] | 6.2[c] | 4.3[d] | 0.22[b] |
| I | >50[c] | 11.93[f] | 3.6[c] | 6.3[d] | 0.48[b] |
| K | 46.65 | 26.60[a,b] | 54.9[a] | 25.2[a,b,c] | 0.16[b] |
| L | 65.48 | 23.27[b,c,d] | 16.5[b,c] | 20.6[a,b,c,d] | 0.41[b] |
| M[d] | 39.02 | | | | |
| O | 64.57 | 17.16[c,d,e,f] | 14.3[b,c] | 23.9[a,b,c] | 4.59[a,b] |
| R | 41.08 | 21.79[b,c,d] | 30.5[b] | 33.9[a] | 4.49[a,b] |
| U | 51.94 | 20.49[b,c,d,e] | 13.2[b,c] | 12.8[b,c,d] | 5.54[a,b] |
| V | 59.82 | 17.51[c,d,e,f] | 13.7[b,c] | 18.5[a,b,c,d] | 5.54[a,b] |
| 1075 | 63.15 | 23.99[b,c] | 30.5[b] | 19.2[a,b,c,d] | 6.67[a,b] |

[a] Doubling times for each cell strain were calculated using the cell growth curves of FIG. 10.
[b] Duncan's multiple range analysis was used to determine significant differences. Cell strains with the same superscript letter are not significantly different.
[c] This represents an estimate of the doubling time. Actual calculations were not made.
[d] The cell line was lost before data was collected.

8.2.3 VIRAL PRODUCTIVITY OF CELL STRAINS FOR HzSNPV

The relative productivity of each cell strain for the HzS-1 5 plaque-purified isolate of HzSNPV was examined by estimating the percentage of infected cells, the average number of OBs per cell, the total infectious ECV released, and the total number of OBs per culture by 7 days post infection (Table VII). Statistical analysis of both OBs per culture and OBs per cell revealed 3 and 6 significant groupings, respectively, using Duncan's Multiple Range (DMR) analysis. The overall average counts of OBs/cell ranged from 30.88 (UND-H) to 11.93 (UND-F), and overall average counts of OBs/culture ranged from $54.9 \times 10^5$ (UND-K) to $3.6 \times 10^5$ (UND-I) DMR analysis of the percentage infected cells per culture revealed 4 statistical groupings with means ranging from 33.9% (UND-R) to 4.3% (UND-H). The ECV productivity data was separable into 2 significant groupings and ranged from $5.4 \times 10^6$ (HZ1075) to $1.6 \times 10^5$ (UND-K) TCID$_{50}$ per ml.

There was no apparent correlation between any of the parameters used to estimate the viral productivity of the cloned cell strains. The population doubling times were also unrelated to these productivity estimates. For example, UND-C and UND-K had similar population doubling times (48.3 vs. 46.65 hours). The strains were significantly different in OBs per cell (16.09 vs. 26.0) and OBs per culture ($23.2 \times 10^5$ vs. $54.9 \times 10$ ), but were statistically similar in percentage of infected cells per culture and levels of ECV produced (Table VII). On the other hand, strain UND-L with a long population doubling time (65.48 hours) and strain UND-R with a much shorter doubling time (41.8 hours) were not significantly different in any of the productivity parameters tested. Strain UND-L and the parental cell line HZ1075 had similar population doubling times (65.48 hours vs. 63.15 hours) and were significantly different only for ECV production.

8.2.4. ISOZYME ANALYSIS OF CELL STRAINS AND CELL LINES

To confirm the origin of the cloned cell strains, we compared their staining patterns for the isozymes fumarate hydratase (FUM), lactate dehydrogenase (LDH), esterase (EST) (FIG. 11), and malate dehydrogenase (MDH, not shown) with those of both the IPLB-HZ1075 parental cell line and larval tissues from the host of origin, H. zea. The FUM, LDH, and MDH patterns of all the cloned cell strains were identical to those of H. zea larval tissues and the parental IPLB-HZ1075 cell line.

The pattern obtained with esterase staining was particularly complex. While all the cloned strain patterns were similar to the larval and parental cell line patterns, individual differences were apparent between cloned cell strains. This further substantiates the clonal character of these cell strains.

The IPLB-HZ1075 cell line was compared to other lepidopteran and one dipteran cell lines maintained in our laboratory. Cell homogenates were prepared and electrophoresed as described above, and stained for either LDH or MDH (FIG. 12). The Rf values for each of the cell line isozyme bands were calculated using the IPLB-HZ1075 bands as reference (Rf=1.0) and are presented in Table VIII.

TABLE VIII

Rf VALUES OF SEVERAL INSECT CELL LINES FOR LDH MDH[a]

| CELL LINE | LDH[b] | MDH[c] | INSECT OF ORIGIN |
|---|---|---|---|
| ACT-10 | 1.03 | 10.0 | AEDES AEGYPTI |
| BTI-EAA | 0.77 | 4.0 | ESTIGMENE ACREA |
| IPLB-HZ1075 | 1.00 | 1.0 | HELIOTHIS ZEA |
| IPLB-SF-21AE | 0.77 | 1.0 | SPODOPTERA FURGIPERDA |
| TN-368 | 0.58 | 1.9 | TRICHOPLUSIA NI |

[a] Cell extracts were electrophoresed in a 5% polyacrylamide gel (95% acrylamide, 5% bis-acrylamide) in TC buffer and stained for LDH or MDH. Rf values were calculated relative to the migration of the IPLB-HZ1075 enzyme.
[b] Lactate Dehydrogenase
[c] Malate Dehydrogenase The pattern obtained for MDH distinguished the IPLB-HZ1075 cell line from all but one (IPLB-SF21AE) of the lepidopteran cell lines, and from the single dipteran cell line originated from Aedes aegypti. Although the Spodoptera frugiperda IPLB-SF21AE cell line was indistinguishable from IPLB-HZ1075 by staining for MDH, it was distinguishable by staining for LDH.

9. EXAMPLE

LARVAL HOSTS FOR USE IN HELIOTHIS EXPRESSION SYSTEMS

The subsections below describe a method for growing *Heliothis zea* larvae in order to mass-culture recombinant viruses made in accordance with the invention. The non-melanizing strains of HzSNPV, such as those described in Section 6, supra, are preferred for use in the larval expression systems of the present invention.

9.1. INSECT DIET PREPARATION

This procedure describes the preparation of diet for *Trichoplusia ni* and *Heliothis zea.* The diet for *Estigmene acrea* requires twice the amount of vitamin mix.

| FORMULA | Per Liter | Per 500 ml |
|---|---|---|
| Pinto beans in 90 ml water | 18 g | 9 g |
| Agar (Sigma) | 25 g | 12.5 g |
| Vitamin diet fortification mixture (ICN) | 3.3 g | 1.66 g |
| Casein (Sigma) | 42 g | 21 g |
| Sucrose (ICN) | 42 g | 21 g |
| Wheat Germ (NIC) | 36 g | 18 g |
| Wesson's Salt Mix (ICN) | 12 g | 6 g |
| Alfacel (non-nutritive bulk) | 6 g | 3 g |
| Methyl Paraben in 18 ml 95% ethanol | 1.66 g | 0.83 g |
| Sorbic Acid (Sigma) | 1.66 g | 0.83 g |
| Ascorbic Acid (Sigma) | 5 g | 2.5 g |
| Streptomycin Sulfate (Sigma) | 0.16 g | 0.08 g |

The diet mix is prepared as follows:
1. The methyl paraben is dissolved in alcohol before the procedure is started.
2. Bring 100 ml of water to a boil. While rapidly stirring, slowly add the agar. Rapid stirring is necessary to prevent the agar from clumping. If the agar clumps, it must be broken up with a spatula.

The diet mix is prepared as follows:

1. The methyl paraben is dissolved in alcohol before the procedure is started.

2. Bring 100 ml of water to a boil. While rapidly stirring, slowly add the agar. Rapid stirring is necessary to prevent the agar from clumping. If the agar clumps, it must be broken up with a spatula.

3. Reheat the mix until small bubbles appear on the side of the beaker.

4. Mix the melted agar and the pinto beans using a blender.

5. Mix on high for 1.5 minutes.

6. Add the rest of the components and mix on high for another 1.5 minutes.

7. Dispense the media into the appropriate containers. Allow to cool at room temperature (15-30 minutes).

8. Store the media in the refrigerator in a sealed container until needed.

9.2. COLONY MAINTENANCE

The diet prepared as described is dispensed so that each larva receives a minimum of approximately 10 ml.

9.2.1 REARING OF T. NI OR H. ZEA

The rearing conditions for *T. ni* or *H. zea* are: 28°-30° C., relative humidity of 65-70%, and photoperiod of 12 hours (each 24 hours).

Upon pupation, the pupae are combined into a flight cage of one cubic foot size, at 40 pupae/cage. The adult moths are allowed to emerge and feed on a mixture of 250 g sucrose, 25 ml honey, 5 g ascorbic acid, 5 g methyl paraben (dissolved initially in 5 ml 95% ethanol before addition), plus 500 ml distilled $H_2O$ (components are dissolved with moderate heat). The feeding mix is presented to the adult moths in a 15 ml conical centrifuge tube equipped with a cap through which a two inch long dental wick extends, so that the adults can feed on the dental wick. The walls of the flight cage are lined with sterilized paper towels, on which the adult moths lay their eggs. The paper towels containing the eggs are removed from the cage with aseptic precautions and transferred to a plastic box, termed a crisper, in which some of the agar-based diet mixture is present. The larvae emerge from the eggs in the crisper. Since the larvae are positively phototropic, a light is shone at the end of the crisper where the diet mix is located, so that the larvae move toward the diet mix and feed upon it. The feeding of the larvae on the diet mix increases yield of larvae, since the larvae are cannibalistic and would otherwise eat other larvae and unhatched eggs. Because the larvae are cannibalistic, they are segregated within a day after they emerge. This segregation is accomplished by hand, using an artist's brush which has been sterilized in 0.25% Clorox TM, and rinsed with double distilled $H_2O$. The brush is used to gently lift the larvae and place each individual larva alone into a cup. The larvae are allowed to grow in the cups until pupation, at which time the pupae are placed into the flight cages.

Since *T. ni* are not as cannabalistic as *H. zea,* a slightly different protocol is alternatively used. After *T. ni* eggs are laid upon the paper towels, a one inch square piece of the paper towel is placed on the lid of a quart cup (J. Cup, Dart Container Corp., Mason, Michigan, Cat. No. 8SJ20) containing 20-30 ml of liquid agar-based diet mixture that has solidified. The cup is inverted on top of the paper. The larvae hatch and migrate up toward the diet surface. The paper is then removed from the bottom and the cups are turned right-side up. The larvae are allowed to grow in the cups until pupation, at which time the pupae are placed into the flight cages.

9.2.2. REARING OF G. MELONELLA

The rearing of *G. melonella* largely follows the same protocol as described in Section 9.2.1. supra for *T. ni* or *H. zea,* with the following differences:

No photoperiod is necessary for *G. melonella* growth. The temperature can range from 25° to 30° C. The relative humidity of ambient room conditions is suitable.

The larva diet for *G. melonella* is composed of a mixture of 200 ml honey, 100 ml glycerine, and 1 box Gerber TM's mixed cereal. The diet mixture is put into a quart Mason jar fitted with a wire-mesh screen at the top, into which the *G. melonella* eggs are placed. After the larvae emerge, more diet mix is added as necessary until the larvae form cocoons. Since *G. melonella* larvae are not as cannibalistic as *H. zea* larvae, it is not necessary to segregate the larvae. When the larvae are in the last instar stage and start forming cocoons, they are taken out of the jar by hand (with gloves) and placed together in a crisper. The insects pupate and the adults emerge within the crisper. The adult moths lay eggs in the cracks or crevices of the crisper without feeding. Eggs are thus laid at the interface of the lid and the box, so that when the lid is removed, the eggs adhere to the lid. The eggs are then stripped off the lid by using a razor blade, and placed in a Mason jar containing the diet mixture.

9.3. GERM-FREE COLONIES

We are engaged in the establishment of insect colonies which are totally germ-free. We have been able to sterilize *H. zea* and *T. ni.* eggs, with egg survival of the sterilization process. The eggs are placed on toweling paper and exposed to peracetic acid for 30 minutes. The eggs are then placed in a sterile environment (an isolater) and rinsed off with sterile water while within the isolater. The eggs thus sterilized give rise to germ-free larvae.

10. EXAMPLE: HELIOTHIS POLYHEDRIN GENE AND PROMOTER IN AUTOGRAPHA SHUTTLE VECTOR

Plasmid pEcoRI-I (Vlak, J. M., et al., 1981, J. Virol. 40: 762-771; Rohel, D. Z., et al., 1983, Virology 124:357-365; Smith, G. E., et al., 1982, J. Virol. 44:199-208), containing the polyhedrin gene of AcNPV, was used as starting material for the construction of an Autographa shuttle vector containing the Heliothis polyhedrin gene and promoter (FIGS. 13, 14). A 2 kb XhoI to BamHI fragment was isolated and subcloned into the SalI and BamHI sites of M13mp19, generating clone mp19pEcoIXB. A DNA fragment was synthesized, corresponding to the Autographa polyhedrin sequence extending from the EcoRV site in the promoter region to the transcription initiation site, followed by a multiple cloning site (MCS) containing BamHI, EcoRI, SalI, and KpnI restriction enzyme recognition sites. Synthesis of the oligonucleotide was by use of an Applied Biosystems Model 380A DNA synthesizer (automated phosphoramidite chemistry). The synthetic fragment was cloned between the EcoRV and KpnI sites of mp19pEcoIXB, resulting in clone mp19A1d.

The HindIII to KpnI fragment of mp19A1d was isolated. (The XhoI site was lost in the cloning into the SalI site of mp19, and the HindIII site of the mp19 MCS is a convenient nearby site). The KpnI to BamHI fragment of pEcoRI-I was also isolated. These two fragments were cloned into the HindIII and SstI sites of the MCS of pUC12 (FIG. 13). The ligation included a synthetic oligonucleotide, 5'-GATCAGCT-3', in order to permit the ligation of the BamHI end of the pEcoRI-I fragment into an SstI end of pUC12, and to remove the BamHI site probably by the mechanism shown below:

```
---G        + 5'-GATCAGCT-3' +      c---
---CCTAG-5'      oligo         3-tcgag---

BamHI end                      SstI end

---GGATCAGCTc---
            ---CCTAGtcgag---
```

The resulting clone, pAV1.5, included Autographa sequences extending from the XhoI site 5' of the polyhedrin gene to the transcription initiation site, a MCS, and Autographa sequences extending from the KpnI site in the carboxy-coding end of the polyhedrin gene to a BamHI site 3' of the gene. The XhoI and BamHI sites were lost.

Plasmid pAV1.5 and plasmid pHX12 were used as the parental plasmids for the construction shown in FIG. 14. A 2 kb PstI-EcoRI fragment of pAV1.5 (containing the Autographa polyhedrin promoter) and a 4.2 kb SalI-PstI fragment of pAV1.5 (containing pUC12 sequences) were isolated. A 2.2 kb EcoRISalI fragment of pHX12 (containing the Heliothis polyhedrin promoter and coding sequences) was isolated, and ligated to the PstI-EcoRI and SalI-PstI pAV1.5-derived fragments. The resulting plasmid, termed pAVHp6, contains the Heliothis polyhedrin promoter and coding sequences, flanked by Autographa polyhedrin sequences including the Autographa polyhedrin promoter. pAVHp6 can thus be used to transfer the Heliothis polyhedrin gene into AcNPV through in vivo recombination, resulting in a recombinant virus that can comprise an expression system in accordance with the present invention. pAVHp6 can also be used to create a recombinant AcNPV with two polyhedrin promoters. One thus has the potential to express two different heterologous genes within the same virus. In addition, if foreign DNA is inserted and expressed under the control of the Autographa promoter in such a recombinant virus, the parental Heliothis polyhedrin promoter and gene can presumably ensure the retention of occlusion body formation.

10.1. AUTOGRAPHA SHUTTLE VECTORS ENCODING AN EPITOPE OF THE INFLUENZA HEMAGGLUTININ WITHIN THE POLYHEDRIN GENE

The strategy being used to construct an Autographa shuttle vector containing sequences which encode an epitope of influenza hemagglutinin within a portion of the polyhedrin coding sequences is diagrammed in FIG. 15.

FIG. 15 depicts a strategy for cloning amino acids 98-106 of the influenza hemagglutinin into the amino-terminal coding sequence of the Autographa polyhedrin gene. This strategy can be used to attempt to insert the influenza sequence into the Autographa polyhedrin sequence contained in the M13 derivative mp19EcoIXB (described in Section 10., supra) within the sequence encoding the second amino acid of the polyhedrin protein. An oligonucleotide (termed Rol-1) can be synthesized (Applied Biosystems Model 380A), which is homologous to the region containing the HpaII cleavage site within the codon for amino acid 2. Rol-1 is annealed to mp19EcoIXB single-stranded DNA, which is then cut with HpaII. Annealing of the oligonucleotide creates the requisite double stranded region for restriction endonuclease cleavage. The linear single-stranded DNA with HpaII-derived ends is isolated by heat denaturation and gel purification. An oligonucleotide corresponding to amino acids 98-106 of influenza hemagglutinin (termed Rol-2) is synthesized. Rol-2 is then annealed to a third synthetic oligonucleotide (Rol-3) which is complementary to Rol-2. In addition, Rol-3 has 5' and 3' termini which extend beyond Rol-2 which are complementary to the HpaII-derived ends of the isolated single-stranded phage DNA. Thus the annealed Rol-2/Rol-3 DNA can be ligated to the isolated single-stranded phage DNA, forming a circular DNA molecule.

After transformation of bacterial cells with the ligated complex, the desired transformant can be selected by hydridization to radiolabeled Rol-3 according to the procedure of Benton and Davis (1977, Science 196:180-182). In addition, Rol-3 encodes two restriction sites, MluI and NsiI, which are not found in the parental mp19EcoIXB DNA. Thus, the identity of selected transformants can be confirmed by the presence of MluI and NsiI restriction sites in the phage DNA isolated from transformants.

As an alternative, a similar strategy to that described supra may be used in order to cut the polyhedrin sequence contained within mp19EcoIXB as the BamHI site within the sequence encoding amino acid 58.

11. EXAMPLE

EXPRESSION OF B-GALACTOSIDASE IN HELIOTHIS ZEA NUCLEAR POLYHEDROSIS VIRUS EXPRESSION SYSTEM

We describe the production of a heterologous protein in *Heliothis zea* (Boddie), using an expression system based on HzSNPV. Plasmid pHE2.6lac was constructed (see Section 6.3.3, supra) by fusing the lacZ gene of *Escherichia coli* to 5' sequences of the polyhedrin gene of HzSNPV. By in vivo recombination, this plasmid was used to construct a recombinant HzSNPV that produced B-galactosidase in larvae and cultured cells. Expression of B-galactosidase showed temporal regulation. Levels of B-galactosidase in cultured cells and larvae were at least 200 ug/$10^6$ cells in culture and greater than 0.1% total wet weight in larvae.

11.1. MATERIALS AND METHODS

11.1.1. CELLS AND VIRUSES

HzS-15, a plaque-purified clone of HzSNPV Elcar TM strain, was used as the parental virus. Monolayer cultures of IPLBHZ1075 UND-K, a cloned line of *Heliothis zea* IPLB-HZ1075 (Goodwin, R. H., 1975, In vitro 11:369–378), were grown at 28° C. in TNM-FH medium (Hink, W. F., 1970, Nature 22:466–467) supplemented with 10 g/l BSA (Miles Scientific, Naperville, Ill.), 2 g/l L-glutamine and 10% fetal calf (Gibco, Grand Island, N.Y.), TNM-FH-10. Virus stocks were made by infecting monolayers of cells at a multiplicity of infection of 0.1, harvesting the culture medium after 10 days, filtering the medium through a 0.45 um filter, and storing at 4° C. with 0.1% agarose. Stocks were titered by the plaque assay method (Fraser, M. J., 1982, J. Tis. Cult. Meth. 7:43–46).

11.1.2. RECOMBINANT PLASMID CONSTRUCTS

Recombinant plasmids were constructed using the protocols of Maniatis et al. (1982, Molecular Cloning, A Laboratory Manual, Cold Spring Harbor, N.Y.). Restriction enzymes were purchased from Promega (Madison, Wis.). Bacterial alkaline phosphatase and T4 DNA ligase were obtained from BRL (Gaithersburg, Maryland). Oligonucleotides were synthesized by using an Applied Biosystems, Inc. Model 380A DNA Synthesizer (CA).

11.1.3 TRANSFECTION AND PLAQUE ASSAYS $1.5 \times 10^6$ cells (grown for two passages in TNM-FH medium supplemented with 5.55 g/l BSA and 20% fetal calf serum, TNM-FH-20) were allowed to attach overnight in 60 mm plates and were transfected using the CaCl$_2$ precipitation method of Graham and Van der Eb (1973, Virology 52:456–460). Eighty ng of viral DNA and 10 ug of plasmid DNA were used in co-transfection experiments for construction of recombinant viruses by in vivo recombination. The precipitate plus medium was replaced after 16 hours with 3 ml TNM-FH-20 medium. Cells were allowed to recover for 7 days. Fresh monolayers in 60 mm plates were incubated 18 hours at 28.C with 3 ml TNM-FH-10 medium containing 100 ul of supernate from transfected cells. Cells were overlaid with 3 ml of 0.4% SeaPlaque agarose (FMC Bioproducts, Rockland, Me.) in TMN-FH-10 medium. After 7 days, cell lawns were examined for plaques (Fraser, M. J., 1982, J. Tis. Cult. Meth. 7:43–46). Six ul/plate of a 20 mg/ml solution of 5-bromo-4-chloro-3-indolyl-B-D-qalactopyranoside (X-gal) in dimethyl-formamide was added to agarose overlays for selection of recombinant viruses expressing B-galactosidase.

11.1.4. PURIFICATION AND PROPAGATION OF RECOMBINANT VIRUS

Blue plaques were removed from plates using a disposable pipet tip, and were placed in 1 ml of complete medium. Tubes were vortexed briefly to release virus from the agarose, and 100 ul were used to inoculate fresh monolayers on 60 mm plates for agarose overlays. Recombinant viruses were plaque purified in this manner three times or until two successive rounds of platings gave all blue plaques that were occlusion body negative. A virus stock was made by picking and adding the whole plaque to one well of a 24-well plate seeded with $5 \times 10^4$ cells in TNM-FH-10. After two weeks, the supernate from the well was added to a 60 mm plate seeded with $1.5 \times 10^6$ cells. After 10 days, the supernate from the 60 mm plate was filtered through a 0.45 um filter and used to infect a T25 flask of cells After another 10 days, the supernate from the T25 flask was filtered and used to infect a T75 flask. After 10 days, the supernate from the T75 flask was removed and filtered. Two ml of the filtered supernate from the T75 flask was used to infect a T150 flask. After 10 days, the supernate from the T150 flask was removed, filtered, stabilized with 0.1% agarose, and stored at 4° C. A most probable number or dilution assay was used to titer the recombinant stock. A 96-well plate was seeded with $1 \times 10^4$ cells/well. Six wells were inoculated with 1 ul of a $10^3$, $10^4$, $10^5$, or $10^6$ dilution. Duplicate dilutions were done so that a total of 12 wells were inoculated with each dilution. After seven days, 1 ul of a 20 mg/ml X-gal solution was added to each well. The plate was examined every day for another 10 days for development of blue color in the wells. The number of blue wells for each set of dilutions was counted and the probable titer figured from a most probable number table.

11.1.5. ISOLATION OF VIRAL DNA FROM INFECTED LARVAE 50 ml of infected *H. zea* larvae were ground with a mortar and pestle in 100 ml of ice-cold TE buffer (10 mM Tris, 1 mM EDTA, pH 7.5) with 0.1% dithiothreitol. The homogenate was passed through several layers of cheesecloth. The homogenate was then centrifuged for 20 minutes at 10,000 X g. The pellet was resuspended in 30 ml ice-cold TE buffer. Polyhedra were banded twice by loading 5 ml on 15 ml continuous sucrose gradients from 40–63% w/w in TE buffer, and spinning 30 minutes at 100,000×g in an SW30 rotor. After each spin, the band of polyhedra was removed with a plastic transfer pipet (Fisher), diluted with distilled, deionized water to 20 ml, and pelleted by spinning for 30 minutes at 10,000 X g. Polyhedra were resuspended in 20 ml of TE buffer. The polyhedral suspension was diluted 1:4 with alkaline buffer (0.1 M Na$_2$CO$_3$, 0.17 M NaCl, pH 10.8) at room temperature to liberate virus. After 5 minutes, 5 ml of virus was loaded on a 15 ml continuous sucrose gradient from 25 to 53% w/w in TE buffer and spun 30 minutes at 100,000×g in an SW30 rotor. The virus band was removed with a transfer pipet. Virus was diluted to 20 ml with distilled, deionized water and pelleted by spinning 30 minutes at 100,000×g in an SW30 rotor. Each virus pellet was resuspended in 1 ml of TE buffer with 0.15 M KCl. The virus suspension was incubated for 15 minutes at 65.C. To lyse virus, 150 ul of 20% sarcosyl and 150 ul of a 20 mg/ml Proteinase K solution were added to 3 ml of virus and incubated 2 hours at 42° C. Next, 3.3 g of CsCl and 0.25 ml of a 10 mg/ml ethidium bromide stock solution were added, mixed gently, and spun for 24 hours in an SW50.1 rotor at 40,000 rpm. The upper and lower bands were removed using a plastic transfer pipet, extracted with NaCl-saturated isopropanol until all of the ethidium bromide was removed, and dialyzed overnight in 4 liters of 0.1 X SSC. DNA was stored at 4° C.

11.1.6. ISOLATION OF TOTAL DNA FROM INFECTED CELLS

Medium was removed from cells in 60 mm petri dishes at 10 days post-infection Total DNA was isolated from infect cells by adding three ml of a 4 M guanidinium solution and extracting three times with equal volumes of phenol:chloroform:isoamyl alcohol (25:24:1) and precipitating twice with ethanol. After restriction digests with appropriate enzymes and electrophoresis in a 60 ml 0.7% agarose gel, DNA was transferred to a nylon membrane by capillary action (Maniatis et al., 1982, Molecular Cloning, A Laboratory Manual, Cold Spring Harbor, N.Y.). Hybridizations were done using 50% formamide.

11.1.7. INFECTION OF CELLS AND B-GALACTOSIDASE ASSAYS

Two 24-well plates were seeded with $5 \times 10^4$ cells/well in TNM-FH-10. Cells were allowed to attach overnight. Sixteen wells were infected with HzS15Bgal-D3, HzS-15, or left uninfected, by replacing the medium with 0.5 ml viral stock of $3 \times 10^5$ pfu (plaque-forming units)/ml or TNM-FH-10. This was considered time $t_0$. At 18 hours post-infection., the inoculum was removed and 0.5 ml TNM-FH-10 medium was added. At 24 hours post-infection, the medium on the cells was replaced with TNM-FH medium with 10% fetal calf serum and no added BSA. At 40 hours post-infection, the medium was replaced with Grace's medium. Duplicate wells of cells for each inoculum were harvested at approximately 12 hour intervals. Cells and supernate were removed from a well by using a 1 ml pipet. Cells were pelleted by spinning for 10 minutes at 3000 rpm in a Sorvall 2B centrifuge. The supernate was transferred to another sterile tube and both tubes were quickly frozen in a liquid nitrogen bath and stored at $-70°$ C. until analysis. B-galactosidase activity was assayed by using a modification of the Pharmacia procedure (1986, B-galactosidase assay protocols: preparation of extracts and assay conditions in prokaryotic and eukaryotic cells, Analects, Pharmacia 4–5). Cell pellets were resuspended by adding 25 ul of FT buffer. Cells were lysed in 1.5 ml tubes by adding 10 ul of 10% NP-40 and 2 ul of chloroform. Cells were vigorously vortexed for 5 seconds. Aliquots of extract and Z buffer were mixed to give 200 ul total. Then, 40 ul ONPG Reaction Buffer was added and tubes incubated at 30° C. The reaction was stopped with 100 ul of 1 M $Na_2CO_3$ when a faint yellow color appeared. The absorbance at 420 nm ($A_{420}$) was measured. B-galactosidase (Bgal) activity was calculated according to the following:

$$Bgal\ units/ml = (A_{420}/0.0045)/(minutes\ reaction\ time \times ml\ of\ extract).$$

Protein concentration was determined using the assay of Bio-Rad Laboratories, Richmond, Calif., based on the Bradford method. An aliquot was also boiled for three minutes with sample buffer for separation on 9% polyacrylamide gels followed by staining with Coomassie blue and Western blotting. These boiled samples were stored at $-20°$ C. until needed. Rabbit anti-B-galactosidase antibody from Cappel was used for Western blots. Mouse anti-rabbit IgG conjugated to alkaline phosphatase was used as the second antibody.

11.1.8. INFECTION OF LARVAE AND B-GALACTOSIDASE ASSAYS

Larvae were reared in cups with the pinto-bean agar-based diet of Ignoffo (1963, Ann. Ent. Soc. Am. 56:178-182). Larvae were infected by direct oral inoculation of infected cells on neonate (first instar) or one to two inch larvae (third to fourth instar). Control animals were given distilled water. Larger infected larvae were smashed individually in 450 ul of FT buffer with 50 ul 10% NP-40 and 20 ul chloroform. Homogenate was spun for 10 minutes in a microcentrifuge. The larval extract was assayed as described above for the cell extract. Neonate larvae were smashed in 45 ul of FT buffer, 5 ul of 10% NP-40, and 2 ul of chloroform.

11.2. RESULTS

11.2.1. CONSTRUCTION OF HzS15Bgal-D3

Plasmid pHE2.61ac was constructed as described supra in Section 6.3.3. Transfections were performed as described supra in Section 11.1.3. Transfection supernates produced a mean of 576 pfu/$10^6$ cells with 5% of the plaques turning blue in the presence of X-gal. One of the blue plaques, HzS15Bgal-D, was plaque-purified through three rounds of purification. A blue plaque from the third round, HzS15Bgal-D3, was used to make a virus stock for further study. Plaques picked and resuspended in 1 ml of medium produced a mean of 49 pfu/ml. The titer of the final stock of HzS15Bgal-D3 was $5 \times 10^4$ pfu/ml using a dilution assay on 96-well titer plates of cells.

11.2.2. CHARACTERIZATION OF RECOMBINANT VIRUS EXPRESSING B-GALACTOSIDASE

Time course analysis of production of B-galactosidase by cell infected with HzS15Bgal-D3 showed that B-galactosidase is resulted temporally. Table IX demonstrates the expression of B-galactosidase activity (Units/mg) in cell pellets from HzS15Bgal-D3 infected cells, compared to HzS-15 infected cells and uninfected cells.

TABLE IX

UNITS OF B-GALACTOSIDASE PER MILLOGRAM OF PROTEIN vs. TIME POST-INFECTION FOR HzS15Bgal-D3, HzS15, AND UNINFECTED CELLS

| Hours, post-infection | Units of B-galactosidase per Milligram Protein* | | |
|---|---|---|---|
| | HzS15Bgal-D3 | HzS-15 | Uninfected |
| 17.5 | 4.4 | 3.2 | 4.0 |
| | 3.8 | 9.5 | 0.0 |
| 24.0 | 1.3 | 0.4 | 0.4 |

TABLE IX-continued
UNITS OF B-GALACTOSIDASE PER MILLOGRAM OF PROTEIN vs. TIME POST-INFECTION FOR HzS15Bgal-D3, HzS15, AND UNINFECTED CELLS

| Hours, post-infection | Units of B-galactosidase per Millogram Protein* | | |
|---|---|---|---|
| | HzS15Bgal-D3 | HzS-15 | Uninfected |
| | 0.4 | 1.1 | 0.6 |
| 40.5 | 0.2 | 2.7 | 1.7 |
| | 2.9 | 1.1 | 1.7 |
| 48.0 | 0.0 | 0.0 | 0.0 |
| | 0.0 | 0.0 | 20.0 |
| 65.5 | 73.7 | 3.4 | 3.4 |
| | 97.9 | 1.5 | 13.4 |
| | 27.7 | | |
| | 29.2 | | |
| 72.0 | 187.1 | 2.9 | 13.7 |
| | 39.3 | 12.4 | 14.5 |
| | 118.2 | | |
| | 23.9 | | |
| 88.5 | 366.9 | 7.8 | 6.9 |
| | 214.6 | 2.9 | 19.1 |
| | 217.1 | | |
| | 122.3 | | |
| 97.0 | 276.0 | 4.4 | 17.4 |
| | 510.1 | 8.0 | 1.3 |
| | 177.6 | | |
| | 219.5 | | |

*From determinations of protein levels in cell pellets.

11.2.3. EXPRESSION OF B-GALACTOSIDASE IN CELLS INFECTED WITH RECOMBINANT VIRUS

FIG. 16 shows a Western blot of a 7.5% polyacrylamide gel of cell proteins from cells in a 24-well plate infected with a low multiplicity of infection of virus HzS15Bgal-D4 and harvested after 14 days. The recombinant B-galactosidase protein migrates more slowly than the marker (wild-type) B-galactosidase, because the recombinant is a fusion protein with approximately 10,000 daltons molecular weight of polyhedrin fused to B-galactosidase. Based on the relative staining of the control B-galactosidase protein (lane M, 10 ug of B-galactosidase loaded) and the infected cell protein (Lane 1: $1.6 \times 10^4$ lysed cells loaded from well 1; lane 2: $3.2 \times 10^4$ lysed cells loaded from well 2) on the Western blot, we can conclude that at least 1 ug of recombinant protein is present in the lysate of infected cells that was loaded on the gel, or about 100 ug in $1 \times 10^6$ cells.

FIG. 17 shows a Western blot of a 9% polyacrylamide gel of cell proteins from cells, in well 5 of a 24-well plate, infected with a low multiplicity of infection of virus HzS15Bgal-D4 and harvested after 14 days. The recombinant B-galactosidase protein migrates more slowly than the marker B-galactosidase, because the recombinant is a fusion protein with approximately 10,000 daltons molecular weight of polyhedrin fused to B-galactosidase. Based on the relative staining of the control B-galactosidase protein (lane M: 10 ug of B-galactosidase loaded) and the infected cell protein (lane C: $0.5 \times 10^4$ lysed cells loaded) on the Western blot, we can conclude that at least 1 ug of recombinant protein is present in the lysate of infected cells that was loaded on the gel, or about 200 ug in $1 \times 10^6$ cells.

11.2.4. EXPRESSION OF B-GALACTOSIDASE IN H. ZEA LARVAE INFECTED WITH RECOMBINANT VIRUS

FIG. 18 shows a Coomassie blue-stained 9% polyacrylamide gel of proteins from neonate H. zea larvae (1-3 mg total weight) infected with HzS15Bgal-D3. The only visible bands are those that migrate where the recombinant protein is expected. The units of B-galactosidase activity in the infected neonates was determined to be 518.4 Units/mg protein (lane L1) and 540.0 Units/mg protein (lane L2).

FIG. 19 shows a Western blot of a 9% polyacrylamide gel of proteins from a neonate larva (2 mg total weight) infected with HzS15Bgal-D3 (lane L). The Units of B-galactosidase activity in the infected neonate was determined to be 1563.8 Units/mg protein. The major protein band seen among the Coomassie stained larval proteins co-migrates with the band on the Western blot (FIG. 19) visualized by treatment with anti-B-galactosidase antibody. This result suggests that the recombinant B-galactosidase protein constitutes a significant portion of the dry weight of the infected larvae. About 20% of the larval extract was loaded onto the polyacrylamide gel. Based on the relative staining of the B-galactosidase marker and the larval extract protein, we can conclude that greater than 0.1% of the larval wet weight is recombinant B-galactosidase protein. Table X shows estimates of polyhedrin yield in larvae infected with HzS-15, of 1.8% of total wet weight.

TABLE X
POLYHEDRIN PRODUCTION IN *HELIOTHIS ZEA* LARVAE

| | Wet Larva Weight (gm) | Weight Crude Polyhedra (gm) | %ᵃ | Partially Purified Polyhedra* (mg) | %ᵃ |
|---|---|---|---|---|---|
| 1 | .299 | .061 | 20 | 8.8 | 2.9 |
| 2 | .329 | .052 | 16 | 8.0 | 2.4 |
| 3 | .164 | .104 | 63 | 3.7 | 2.3 |
| 4 | .412 | .060 | 15 | 3.7 | 0.9 |
| 5 | .440 | .041 | 9 | 2.2 | 0.5 |
| 6 | .469 | .108 | 23 | 7.1 | 1.5 |
| | | | | | 1.8 ± 0.9 |

*Solubilized for protein determinations
ᵃPercentage of larva weight represented by polyhedra.

12. DEPOSIT OF MICROORGANISMS

The following *E. coli* strains carrying the listed plasmids have been deposited with the Agricultural Research Culture Collection (NRRL), Peoria, IL, and have been assigned the following accession numbers:

| E. coli Strain | Plasmid | Accession Number |
|---|---|---|
| K12 (DH5) | pHX12 | NRRL B-18172 |
| K12 (DH5) | pHH5 | NRRL B-18173 |
| K12 (DH5) | pHE2.6 | NRRL B-18174 |
| K12 (DH5) | pHE2.61ac | NRRL B-18175 |
| K12 (DH5) | pAVHp6 | NRRL B-18176 |

The following *Heliothis zea* cell line and *Heliothis zea* NPV isolate have been deposited with the American Type Culture Collection, Rockville, Md., and have been assigned the listed accession numbers:

| | | Accession Number |
|---|---|---|
| Heliothis zea cell line: | IPLB-HZ1075/UND-K | ATCC CRL 9281 |
| Heliothis zea NPV isolate: | HzS-15 | ATCC VR 2156 |

The present invention is not to be limited in scope by the microorganisms and cell line deposited since the deposited embodiment is intended as a single illustration of one aspect of the invention and any microorganisms or viruses which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

It is also to be understood that all base pair sizes given for nucleotides are approximate and are used for purposes of description, and figures which diagrammatically depict DNA sequences are not necessarily drawn to scale.

What is claimed is:

1. A recombinant *Heliothis Zea* nuclear polyhedrosis virus selected from the group consisting of HzS5, HzS8, HzS9, HzS15, HzS21, HzS22, HzS24, and HzS25, capable of causing sloe melanization in a larval host, the genome of which comprises Heliothis polyhedrin promoter and a nucleotide sequence encoding a heterologous peptide or protein expressed under the control of the Heliothis polyhedrin promoter so that the heterologous peptide or protein is expressed in an insect host cell infected with the recombinant virus.

2. The recombinant virus according to claim 1 in which the *Heliothis zea* nuclear polyhedrosis virus comprises virus strain HzS-15, as deposited with the ATCC and assigned Accession Number VR 2156.

3. The recombinant virus according to claim 1 in which the host comprises an infected insect.

4. The recombinant virus according to claim 1 in which the host comprises a Heliothis cell line.

5. The recombinant virus according to claim 4 in which the Heliothis cell line comprises Heliothis zea cell line IPLB-HZ1075.

6. The recombinant virus according to claim 4 in which the Heliothis cell line comprises *Heliothis zea* cell line IPLB-HZ1075/UND-K, as deposited with the ATCC and assigned Accession Number CRL 9281.

7. The recombinant virus according to claim 1 in which the heterologous peptide or protein comprises an unfused peptide or protein.

8. The recombinant virus according to claim 1 in which the heterologous peptide or protein comprises a fusion protein.

9. The recombinant virus according to claim 8 in which the heterologous peptide or protein comprises a recombinant occlusion body.

10. The recombinant virus according to claim 7, 8, or 9 in which the heterologous peptide or protein comprises an epitope of a pathogenic microorganism.

11. The recombinant virus according to claim 10 in which the pathogenic microorganism comprises a virus.

12. The recombinant virus according to claim 11 in which the virus comprises Hepatitis A virus.

13. The recombinant virus according to claim 11 in which the epitope comprises amino acids 98–106 of influenza hemagglutinin.

14. The recombinant virus according to claim 1 in which the heterologous peptide or protein comprises *E. coli* beta-galactosidase.

15. The recombinant virus according to claim 1 in which the heterologous peptide or protein has insecticidal activity.

* * * * *